US009861629B1

(12) United States Patent
Hughey et al.

(10) Patent No.: US 9,861,629 B1
(45) Date of Patent: Jan. 9, 2018

(54) OPIOID ABUSE DETERRENT DOSAGE FORMS

(71) Applicant: BANNER LIFE SCIENCES LLC, High Point, NC (US)

(72) Inventors: Justin Hughey, Asheboro, NC (US); Saujanya Gosangari, Jamestown, NC (US); Chue Hue Yang, Greensboro, NC (US)

(73) Assignee: Banner Life Sciences LLC, High Point, NC (US)

( * ) Notice: Subject to any disclaimer, the term of this patent is extended or adjusted under 35 U.S.C. 154(b) by 0 days.

(21) Appl. No.: 15/285,814

(22) Filed: Oct. 5, 2016

Related U.S. Application Data

(60) Provisional application No. 62/238,385, filed on Oct. 7, 2015, provisional application No. 62/310,383, filed on Mar. 18, 2016.

(51) Int. Cl.
| | | |
|---|---|---|
| *A61K 31/485* | (2006.01) | |
| *A61K 47/10* | (2017.01) | |
| *A61K 47/14* | (2017.01) | |
| *A61K 9/48* | (2006.01) | |
| *A61K 9/00* | (2006.01) | |

(52) U.S. Cl.
CPC .......... *A61K 31/485* (2013.01); *A61K 9/0053* (2013.01); *A61K 9/4833* (2013.01); *A61K 9/4858* (2013.01); *A61K 9/4866* (2013.01); *A61K 9/4891* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | |
|---|---|---|
| 4,828,836 A | 5/1989 | Miller |
| 4,861,598 A | 8/1989 | Oshlack |
| 4,970,075 A | 11/1990 | Oshlack |
| 5,266,331 A | 11/1993 | Oshlack |
| 5,273,760 A | 12/1993 | Oshlack |
| 5,286,493 A | 2/1994 | Oshlack |
| 5,472,943 A | 12/1995 | Crain |
| 5,478,577 A | 12/1995 | Kaiko |
| 5,529,787 A | 6/1996 | Ayer |
| 5,549,912 A | 8/1996 | Kaiko |
| 5,656,295 A | 8/1997 | Oshlack |
| 5,672,360 A | 9/1997 | Kaiko |
| 5,702,725 A | 12/1997 | Chadha |
| 5,914,131 A | 6/1999 | Ayer |
| 5,958,452 A | 9/1999 | Oshlack |
| 5,965,161 A | 10/1999 | Oshlack |
| 6,228,863 B1 | 5/2001 | Kaiko |
| 6,261,599 B1 | 7/2001 | Huang |
| 6,277,384 B1 | 8/2001 | Kaiko |
| 6,335,033 B2 | 1/2002 | Oshlack |

(Continued)

*Primary Examiner* — Bethany Barham
*Assistant Examiner* — Barbara Frazier
(74) *Attorney, Agent, or Firm* — Brinks Gilson & Lione

(57) ABSTRACT

Described herein are oral abuse deterrent pharmaceutical compositions, methods for making the same, and methods for treating pain by administering the pharmaceutical composition to a subject in need thereof. In particular, an oral abuse deterrent pharmaceutical composition comprising a soft capsule and a controlled release matrix comprising oxycodone are described.

26 Claims, 30 Drawing Sheets

(56) References Cited

U.S. PATENT DOCUMENTS

| | | | |
|---|---|---|---|
| 6,375,957 | B1 | 4/2002 | Kaiko |
| 6,475,494 | B2 | 11/2002 | Kaiko |
| 6,488,963 | B1 | 12/2002 | McGinity |
| 6,627,635 | B2 | 9/2003 | Kaiko |
| 6,685,964 | B1 | 2/2004 | Bartholomaeus |
| 6,696,066 | B2 | 2/2004 | Kaiko |
| 6,696,088 | B2 | 2/2004 | Wright |
| 6,706,281 | B2 | 3/2004 | Oshlack |
| 6,713,488 | B2 | 3/2004 | Wang |
| 6,733,783 | B2 | 5/2004 | Oshlack |
| 6,734,188 | B1 | 5/2004 | Rhodes |
| 6,743,442 | B2 | 6/2004 | Huang |
| 6,893,661 | B1 | 5/2005 | Odidi |
| 7,129,248 | B2 | 10/2006 | Hong |
| 7,144,587 | B2 | 12/2006 | Wright |
| 7,172,767 | B2 | 2/2007 | Kaiko |
| 7,201,920 | B2 | 4/2007 | Wadgaonkar |
| 7,276,250 | B2 | 10/2007 | McCall |
| 7,332,182 | B2 | 2/2008 | Sackler |
| 7,384,653 | B2 | 6/2008 | Carpanzano |
| 7,399,488 | B2 | 7/2008 | Swager |
| 7,419,686 | B2 | 9/2008 | Kaiko |
| 7,476,402 | B2 | 1/2009 | Wadgaonkar |
| 7,510,726 | B2 | 3/2009 | Wadgaonkar |
| 7,510,727 | B2 | 3/2009 | Oshlack |
| 7,514,100 | B2 | 4/2009 | Oshlack |
| 7,674,798 | B2 | 3/2010 | Hong |
| 7,674,799 | B2 | 3/2010 | Hong |
| 7,674,800 | B2 | 3/2010 | Hong |
| 7,682,633 | B2 | 3/2010 | Boehm |
| 7,682,634 | B2 | 3/2010 | Boehm |
| 7,683,072 | B2 | 3/2010 | Hong |
| 7,691,877 | B2 | 4/2010 | Tran |
| 7,696,208 | B2 | 4/2010 | Kyle |
| 7,740,881 | B1 | 6/2010 | Kaiko |
| 7,749,542 | B2 | 7/2010 | Kaiko |
| 7,771,707 | B2 | 8/2010 | Hirsh |
| 7,776,314 | B2 | 8/2010 | Kugelmann |
| 7,776,861 | B2 | 8/2010 | Sun |
| 7,790,201 | B2 | 9/2010 | Raman |
| 7,790,215 | B2 | 9/2010 | Oshlack |
| 7,815,934 | B2 | 10/2010 | Boehm |
| 7,842,307 | B2 | 11/2010 | Wright |
| 7,842,311 | B2 | 11/2010 | Wright |
| 7,846,476 | B2 | 12/2010 | Oshlack |
| 7,858,119 | B1 | 12/2010 | Midi |
| 7,862,833 | B2 | 1/2011 | Moe |
| 7,906,141 | B2 | 3/2011 | Ziegler |
| 7,914,818 | B2 | 3/2011 | Wright |
| 7,943,173 | B2 | 5/2011 | Wright |
| 7,943,174 | B2 | 5/2011 | Oshlack |
| 7,981,439 | B2 | 7/2011 | Wadgaonkar |
| 8,017,148 | B2 | 9/2011 | Sackler |
| 8,030,310 | B2 | 10/2011 | Kyle |
| 8,075,872 | B2 | 12/2011 | Kugelmann |
| 8,101,630 | B2 | 1/2012 | Wadgaonkar |
| 8,105,631 | B2 | 1/2012 | Kaiko |
| 8,114,383 | B2 | 2/2012 | Kugelmann |
| 8,114,384 | B2 | 2/2012 | Bartholomaus |
| 8,142,811 | B2 | 3/2012 | Oshlack |
| 8,158,156 | B2 | 4/2012 | Boehm |
| 8,178,560 | B2 | 5/2012 | Sun |
| 8,182,836 | B2 | 5/2012 | Mehta |
| 8,192,722 | B2 | 6/2012 | Kugelmann |
| 8,231,898 | B2 | 7/2012 | Oshlack |
| 8,231,901 | B2 | 7/2012 | Wright |
| 8,236,328 | B2 | 8/2012 | Curatolo |
| 8,236,351 | B2 | 8/2012 | Wright |
| 8,298,577 | B2 | 10/2012 | Moe |
| 8,298,579 | B2 | 10/2012 | Abreu |
| 8,309,060 | B2 | 11/2012 | Arkenau |
| 8,309,122 | B2 | 11/2012 | Baichwal |
| 8,323,889 | B2 | 12/2012 | Kugelmann |
| 8,329,216 | B2 | 12/2012 | Baichwal |
| 8,337,888 | B2 | 12/2012 | Wright |
| 8,357,399 | B2 | 1/2013 | Wright |
| 8,361,499 | B2 | 1/2013 | Oshlack |
| 8,377,480 | B2 | 2/2013 | Raman |
| 8,383,152 | B2 | 2/2013 | Galia |
| 8,409,616 | B2 | 4/2013 | Wadgaonkar |
| 8,420,056 | B2 | 4/2013 | Kugelmann |
| 8,425,933 | B2 | 4/2013 | Mehta |
| 8,445,018 | B2 | 5/2013 | Habib |
| 8,445,023 | B2 | 5/2013 | Dargelas |
| 8,449,909 | B2 | 5/2013 | Kilbanov |
| 8,465,774 | B2 | 6/2013 | Wright |
| 8,518,443 | B2 | 8/2013 | Wright |
| 8,524,275 | B2 | 9/2013 | Oshlack |
| 8,551,520 | B2 | 10/2013 | Oshlack |
| 8,557,291 | B2 | 10/2013 | Hirsh |
| 8,586,088 | B2 | 11/2013 | Wright |
| 8,597,681 | B2 | 12/2013 | Park |
| 8,623,418 | B2 | 1/2014 | Tang |
| 8,637,540 | B2 | 1/2014 | Wadgaonkar |
| 8,637,548 | B2 | 1/2014 | Sun |
| 8,647,667 | B2 | 2/2014 | Oshlack |
| 8,652,515 | B2 | 2/2014 | Sackler |
| 8,652,529 | B2 | 2/2014 | Dargelas |
| 8,658,631 | B1 | 2/2014 | Devarakonda |
| 8,673,355 | B2 | 3/2014 | Kaiko |
| 8,685,443 | B2 | 4/2014 | Boehm |
| 8,685,444 | B2 | 4/2014 | Boehm |
| 8,703,186 | B2 | 4/2014 | Mehta |
| 8,703,196 | B2 | 4/2014 | Curatolo |
| 8,715,721 | B2 | 5/2014 | Oshlack |
| 8,741,885 | B1 | 6/2014 | Devarakonda |
| 8,758,813 | B2 | 6/2014 | Rariy |
| 8,758,825 | B2 | 6/2014 | Wright |
| 8,790,694 | B2 | 7/2014 | Shelby |
| 8,808,737 | B2 | 8/2014 | Ahdieh |
| 8,808,740 | B2 | 8/2014 | Huang |
| 8,808,741 | B2 | 8/2014 | Huang |
| 8,815,287 | B2 | 8/2014 | Wright |
| 8,815,289 | B2 | 8/2014 | Huang |
| 8,821,929 | B2 | 9/2014 | Huang |
| 8,822,487 | B2 | 9/2014 | Kaiko |
| 8,822,489 | B2 | 9/2014 | Wadgaonkar |
| 8,822,687 | B2 | 9/2014 | Hong |
| 8,834,925 | B2 | 9/2014 | Huang |
| 8,840,928 | B2 | 9/2014 | Varanasi |
| 8,846,086 | B2 | 9/2014 | Huang |
| 8,846,090 | B2 | 9/2014 | Broegmann |
| 8,846,091 | B2 | 9/2014 | Broegmann |
| 8,846,104 | B2 | 9/2014 | Boehm |
| 8,858,963 | B1 | 10/2014 | Devarakonda |
| 8,877,247 | B2 | 11/2014 | Boehm |
| 8,883,204 | B2 | 11/2014 | Masselink |
| 8,894,987 | B2 | 11/2014 | Huang |
| 8,894,988 | B2 | 11/2014 | McKenna |
| 8,901,113 | B2 | 12/2014 | Hall Yung |
| 8,911,719 | B2 | 12/2014 | Huang |
| 8,920,836 | B2 | 12/2014 | Whitelock |
| 8,932,630 | B1 | 1/2015 | Kaiko |
| 8,936,808 | B1 | 1/2015 | Kaiko |
| 8,936,812 | B2 | 1/2015 | Wright |
| 8,951,555 | B1 | 2/2015 | Oshlack |
| 8,969,369 | B2 | 3/2015 | Kao |
| 8,975,273 | B2 | 3/2015 | Oshlack |
| 8,980,291 | B2 | 3/2015 | Oshlack |
| 8,980,319 | B2 | 3/2015 | Park |
| 8,992,975 | B2 | 3/2015 | Shelby |
| 9,023,401 | B1 | 5/2015 | Oshlack |
| 9,034,377 | B2 | 5/2015 | Wright |
| 9,044,398 | B2 | 6/2015 | Rariy |
| 9,044,402 | B2 | 6/2015 | Overgard |
| 9,050,335 | B1 | 6/2015 | Devarakonda |
| 9,056,051 | B2 | 6/2015 | Kao |
| 9,056,052 | B1 | 6/2015 | Oshlack |
| 9,056,107 | B1 | 6/2015 | Oshlack |
| 9,060,940 | B2 | 6/2015 | Oshlack |
| 9,060,976 | B2 | 6/2015 | Wright |
| 9,073,933 | B2 | 7/2015 | Hong |
| 9,084,729 | B2 | 7/2015 | Kao |
| 9,084,816 | B2 | 7/2015 | McKenna |

(56) References Cited

U.S. PATENT DOCUMENTS

| | | |
|---|---|---|
| 9,095,614 B2 | 8/2015 | McKenna |
| 9,095,615 B2 | 8/2015 | McKenna |
| 9,101,661 B2 | 8/2015 | McKenna |
| 9,101,668 B2 | 8/2015 | Oshlack |
| 9,149,436 B2 | 10/2015 | Vashi |
| 9,149,533 B2 | 10/2015 | Guido |
| 9,161,937 B2 | 10/2015 | Kao |
| 9,168,252 B2 | 10/2015 | Kao |
| 9,198,861 B2 | 12/2015 | Dhanarajan |
| 9,198,863 B2 | 12/2015 | Oshlack |
| 9,205,055 B2 | 12/2015 | Oshlack |
| 9,205,056 B2 | 12/2015 | Oshlack |
| 9,205,082 B2 | 12/2015 | Kaiko |
| 9,216,176 B2 | 12/2015 | Habib |
| 9,301,918 B2 | 4/2016 | Raman |
| 9,433,582 B2 | 9/2016 | Shelby |
| 2001/0033865 A1 | 10/2001 | Oshlack |
| 2001/0036476 A1 | 11/2001 | Huang |
| 2001/0038856 A1 | 11/2001 | Ayer |
| 2002/0004509 A1 | 1/2002 | Kaiko |
| 2002/0006438 A1 | 1/2002 | Oshlack |
| 2002/0013301 A1 | 1/2002 | Kaiko |
| 2002/0058050 A1 | 5/2002 | Kaiko |
| 2002/0058673 A1 | 5/2002 | Kaiko |
| 2002/0192277 A1 | 12/2002 | Oshlack |
| 2003/0026839 A1 | 2/2003 | Oshlack |
| 2003/0031712 A1 | 2/2003 | Kaiko |
| 2003/0035837 A1 | 2/2003 | Kaiko |
| 2003/0044458 A1 | 3/2003 | Carpanzano |
| 2003/0044464 A1 | 3/2003 | Ziegler |
| 2003/0065002 A1 | 4/2003 | Kao |
| 2003/0068371 A1 | 4/2003 | Wright |
| 2003/0068392 A1 | 4/2003 | Sackler |
| 2003/0069263 A1 | 4/2003 | Wright |
| 2003/0073714 A1 | 4/2003 | Wright |
| 2003/0104063 A1 | 6/2003 | Curatolo |
| 2003/0124185 A1 | 7/2003 | Wright |
| 2003/0157167 A1 | 8/2003 | Baichwal |
| 2003/0157168 A1 | 8/2003 | Wright |
| 2003/0190358 A1 | 10/2003 | Oshlack |
| 2003/0190362 A1 | 10/2003 | Oshlack |
| 2004/0047907 A1 | 3/2004 | Oshlack |
| 2004/0052731 A1 | 3/2004 | Lo |
| 2004/0058946 A1 | 3/2004 | Rariy |
| 2004/0081694 A1 | 4/2004 | Oshlack |
| 2004/0086561 A1 | 5/2004 | Kaiko |
| 2004/0170680 A1 | 9/2004 | Oshlack |
| 2004/0185096 A1 | 9/2004 | Oshlack |
| 2004/0202717 A1 | 10/2004 | Mehta |
| 2004/0234600 A1 | 11/2004 | Ayer |
| 2004/0266807 A1 | 12/2004 | Oshlack |
| 2005/0031546 A1 | 2/2005 | Bartholomaus |
| 2005/0063909 A1 | 3/2005 | Carpanzano |
| 2005/0089568 A1 | 4/2005 | Oshlack |
| 2005/0112067 A1 | 5/2005 | Wadgaonkar |
| 2005/0192309 A1 | 9/2005 | Kaiko |
| 2005/0214368 A1 | 9/2005 | Odidi |
| 2005/0222188 A1 | 10/2005 | Hong |
| 2005/0236741 A1 | 10/2005 | Bartholomaeus |
| 2005/0245483 A1 | 11/2005 | Spitzley |
| 2005/0245556 A1 | 11/2005 | Spitzley |
| 2005/0281748 A1 | 12/2005 | Hirsh |
| 2006/0002859 A1 | 1/2006 | Bartholomaus |
| 2006/0128717 A1 | 6/2006 | Sun |
| 2006/0173029 A1 | 8/2006 | Hong |
| 2006/0182801 A1 | 8/2006 | Wright |
| 2006/0193782 A1 | 8/2006 | Arkenau |
| 2006/0193914 A1 | 8/2006 | Ashworth |
| 2006/0258669 A1 | 11/2006 | Kyle |
| 2006/0269604 A1 | 11/2006 | Kaiko |
| 2007/0003616 A1 | 1/2007 | Bartholomaus |
| 2007/0014732 A1 | 1/2007 | Sackler |
| 2007/0048228 A1 | 3/2007 | Kugelmann |
| 2007/0117829 A1 | 5/2007 | Hong |
| 2007/0117830 A1 | 5/2007 | Hong |
| 2007/0117831 A1 | 5/2007 | Hong |
| 2007/0122348 A1 | 5/2007 | Kaiko |
| 2007/0166234 A1 | 7/2007 | Wadgaonkar |
| 2007/0179169 A1 | 8/2007 | Hong |
| 2007/0183979 A1 | 8/2007 | Arkenau Maric |
| 2007/0183980 A1 | 8/2007 | Kugelmann |
| 2007/0197478 A1 | 8/2007 | Tran |
| 2007/0207089 A1 | 9/2007 | Abreu |
| 2007/0237832 A1 | 10/2007 | Kaiko |
| 2007/0237833 A1 | 10/2007 | Kaiko |
| 2007/0259045 A1 | 11/2007 | McKenna |
| 2007/0264327 A1 | 11/2007 | Wadgaonkar |
| 2007/0298103 A1 | 12/2007 | Hayes |
| 2008/0031963 A1 | 2/2008 | Kaiko |
| 2008/0069881 A1 | 3/2008 | Kao |
| 2008/0132532 A1 | 6/2008 | Wright |
| 2008/0166405 A1 | 7/2008 | Mehta |
| 2008/0199530 A1 | 8/2008 | Hirsh |
| 2008/0247959 A1 | 10/2008 | Arkenau Maric |
| 2008/0260819 A1 | 10/2008 | Hirsh |
| 2008/0292694 A1 | 11/2008 | Kaiko |
| 2008/0292700 A1 | 11/2008 | Nghiem |
| 2008/0311049 A1 | 12/2008 | Kugelmann |
| 2008/0311187 A1 | 12/2008 | Ashworth |
| 2008/0312264 A1 | 12/2008 | Bartholomaus |
| 2008/0317854 A1 | 12/2008 | Bartholomaeus |
| 2009/0004292 A1 | 1/2009 | Wadgaonkar |
| 2009/0005408 A1 | 1/2009 | Bartholomaus |
| 2009/0011024 A1 | 1/2009 | Curatolo |
| 2009/0022790 A1 | 1/2009 | Flath |
| 2009/0081290 A1 | 3/2009 | Huang |
| 2009/0148517 A1 | 6/2009 | Chasin |
| 2009/0202629 A1 | 8/2009 | Oshlack |
| 2009/0202634 A1 | 8/2009 | Galia |
| 2009/0227615 A1 | 9/2009 | Hong |
| 2009/0238868 A1 | 9/2009 | Mehta |
| 2009/0253730 A1 | 10/2009 | Wadgaonkar |
| 2009/0297617 A1 | 12/2009 | Hirsh |
| 2010/0028389 A1 | 2/2010 | Merrill |
| 2010/0098771 A1 | 4/2010 | Mehta |
| 2010/0151028 A1 | 6/2010 | Kugelmann |
| 2010/0152449 A1 | 6/2010 | Hong |
| 2010/0172974 A1 | 7/2010 | Chasin |
| 2010/0209351 A1 | 8/2010 | Sackler |
| 2010/0209514 A1 | 8/2010 | Sackler |
| 2010/0216829 A2 | 8/2010 | Tewari |
| 2010/0240675 A1 | 9/2010 | Kyle |
| 2010/0260834 A1 | 10/2010 | Hirsh |
| 2010/0273730 A1* | 10/2010 | Hsu ................ A61K 9/1075 514/49 |
| 2010/0291203 A1 | 11/2010 | Kaiko |
| 2010/0331369 A1 | 12/2010 | Sun |
| 2011/0038927 A1 | 2/2011 | Oshlack |
| 2011/0071192 A1 | 3/2011 | Sun |
| 2011/0077238 A1 | 3/2011 | Hall Yung |
| 2011/0104214 A1 | 5/2011 | Wright |
| 2011/0142943 A1 | 6/2011 | Saim |
| 2011/0150989 A1 | 6/2011 | Dhanarajan |
| 2011/0207762 A1 | 8/2011 | Hong |
| 2011/0230510 A1 | 9/2011 | Wright |
| 2011/0256226 A1 | 10/2011 | Wright |
| 2011/0262532 A1 | 10/2011 | Oshlack |
| 2011/0287095 A1 | 11/2011 | Park |
| 2011/0300217 A1 | 12/2011 | Ayer |
| 2012/0034171 A1 | 2/2012 | Kugelmann |
| 2012/0087982 A1 | 4/2012 | Wadgaonkar |
| 2012/0088786 A1 | 4/2012 | Hayes |
| 2012/0107250 A1 | 5/2012 | Kugelmann |
| 2012/0108621 A1 | 5/2012 | Broegmann |
| 2012/0141583 A1 | 6/2012 | Hahn |
| 2012/0164220 A1 | 6/2012 | Huang |
| 2012/0165359 A1 | 6/2012 | Kaiko |
| 2012/0183612 A1 | 7/2012 | Broegmann |
| 2012/0201761 A1 | 8/2012 | Sackler |
| 2012/0225901 A1 | 9/2012 | Smith |
| 2012/0251637 A1 | 10/2012 | Kugelmann |
| 2012/0252832 A1 | 10/2012 | Kao |
| 2012/0263788 A1 | 10/2012 | Oshlack |
| 2012/0288567 A1 | 11/2012 | Wright |

(56) References Cited

U.S. PATENT DOCUMENTS

| | | |
|---|---|---|
| 2012/0295988 A1 | 11/2012 | Curatolo |
| 2013/0004575 A1 | 1/2013 | Jackson |
| 2013/0005977 A1 | 1/2013 | Hong |
| 2013/0017255 A1 | 1/2013 | Osvaldo |
| 2013/0045960 A1 | 2/2013 | Lo |
| 2013/0090349 A1 | 4/2013 | Geisler |
| 2013/0122087 A1 | 5/2013 | Hillman |
| 2013/0122101 A1 | 5/2013 | Habib |
| 2013/0158061 A1 | 6/2013 | Oshlack |
| 2013/0165418 A1 | 6/2013 | Colucci |
| 2013/0171075 A1 | 7/2013 | Kugelmann |
| 2013/0171257 A1 | 7/2013 | Tewari |
| 2013/0172382 A1 | 7/2013 | Kao |
| 2013/0209560 A1 | 8/2013 | Hamed |
| 2013/0230596 A1 | 9/2013 | Mehta |
| 2013/0251759 A1 | 9/2013 | Bartholomuaes |
| 2013/0251796 A1 | 9/2013 | Huang |
| 2013/0251797 A1 | 9/2013 | Huang |
| 2013/0251798 A1 | 9/2013 | Huang |
| 2013/0251799 A1 | 9/2013 | Huang |
| 2013/0251800 A1 | 9/2013 | Huang |
| 2013/0251801 A1 | 9/2013 | Huang |
| 2013/0251802 A1 | 9/2013 | Huang |
| 2013/0251812 A1 | 9/2013 | Wright |
| 2013/0259938 A1 | 10/2013 | Huang |
| 2013/0259939 A1 | 10/2013 | Huang |
| 2013/0259940 A1 | 10/2013 | Huang |
| 2013/0260015 A1 | 10/2013 | Huang |
| 2013/0273153 A1 | 10/2013 | Dhanarajan |
| 2013/0280176 A1 | 10/2013 | Diezi |
| 2013/0280177 A1 | 10/2013 | Raman |
| 2013/0289062 A1 | 10/2013 | Wadgaonkar |
| 2013/0295177 A1 | 11/2013 | Oshlack |
| 2013/0302418 A1 | 11/2013 | Oshlack |
| 2013/0309303 A1 | 11/2013 | Wright |
| 2013/0310413 A1 | 11/2013 | Kilbanov |
| 2013/0317051 A1 | 11/2013 | Oshlack |
| 2013/0320592 A1 | 12/2013 | Bartholomaus |
| 2014/0010873 A1 | 1/2014 | Overgard |
| 2014/0010875 A1 | 1/2014 | Huang |
| 2014/0011832 A1 | 1/2014 | Huang |
| 2014/0017310 A1 | 1/2014 | Castaneda |
| 2014/0024669 A1 | 1/2014 | Huang |
| 2014/0030327 A1 | 1/2014 | Huang |
| 2014/0031381 A1 | 1/2014 | Huang |
| 2014/0031382 A1 | 1/2014 | Smith |
| 2014/0045877 A1 | 2/2014 | Broegmann |
| 2014/0045878 A1 | 2/2014 | Broegmann |
| 2014/0079780 A1 | 3/2014 | Kugelmann |
| 2014/0080858 A1 | 3/2014 | Kugelmann |
| 2014/0080915 A1 | 3/2014 | Kugelmann |
| 2014/0086847 A1 | 3/2014 | Kugelmann |
| 2014/0086987 A1 | 3/2014 | Park |
| 2014/0099376 A2 | 4/2014 | Wright |
| 2014/0105830 A1 | 4/2014 | Kugelmann |
| 2014/0105977 A1 | 4/2014 | Shelby |
| 2014/0105987 A1 | 4/2014 | Hirsh |
| 2014/0107146 A1 | 4/2014 | Kao |
| 2014/0112981 A1 | 4/2014 | Oshlack |
| 2014/0112984 A1 | 4/2014 | Kugelmann |
| 2014/0113926 A1 | 4/2014 | Bartholomaeus |
| 2014/0121232 A1 | 5/2014 | Rariy |
| 2014/0135355 A1 | 5/2014 | Kao |
| 2014/0155425 A1 | 6/2014 | Sackler |
| 2014/0155489 A1 | 6/2014 | Kugelmann |
| 2014/0170079 A1 | 6/2014 | Kugelmann |
| 2014/0170217 A1 | 6/2014 | Shelby |
| 2014/0187572 A1 | 7/2014 | Wright |
| 2014/0194456 A1 | 7/2014 | Kao |
| 2014/0199394 A1 | 7/2014 | Oshlack |
| 2014/0200236 A1 | 7/2014 | Kaiko |
| 2014/0220126 A1 | 8/2014 | Overgard |
| 2014/0221416 A1 | 8/2014 | Guido |
| 2014/0249185 A1 | 9/2014 | Sun |
| 2014/0256764 A1 | 9/2014 | Abreu |
| 2014/0271840 A1 | 9/2014 | Huang |
| 2014/0275143 A1 | 9/2014 | Gupta |
| 2014/0288113 A1 | 9/2014 | Gupta |
| 2014/0294953 A1 | 10/2014 | Vega Zepeda |
| 2014/0294956 A1 | 10/2014 | Shelby |
| 2014/0296276 A1 | 10/2014 | Wright |
| 2014/0296277 A1 | 10/2014 | Broegmann |
| 2014/0322311 A1 | 10/2014 | Kugelmann |
| 2014/0322323 A1 | 10/2014 | Galia |
| 2014/0329847 A1 | 11/2014 | Ahdieh |
| 2014/0336213 A1 | 11/2014 | Wadgaonkar |
| 2014/0356294 A1 | 12/2014 | Kugelmann |
| 2014/0357658 A1 | 12/2014 | Kaiko |
| 2014/0377348 A1 | 12/2014 | Oshlack |
| 2014/0378498 A1 | 12/2014 | Devarakonda |
| 2015/0004244 A1 | 1/2015 | Varanasi |
| 2015/0005332 A1 | 1/2015 | Varanasi |
| 2015/0005335 A1 | 1/2015 | Broegmann |
| 2015/0005336 A1 | 1/2015 | Kaiko |
| 2015/0025101 A1 | 1/2015 | Kaiko |
| 2015/0028512 A1 | 1/2015 | Huang |
| 2015/0031718 A1 | 1/2015 | Wright |
| 2015/0037409 A1 | 2/2015 | Oshlack |
| 2015/0037411 A1 | 2/2015 | Huang |
| 2015/0037412 A1 | 2/2015 | Huang |
| 2015/0037413 A1 | 2/2015 | Huang |
| 2015/0080384 A1 | 3/2015 | Hall Yung |
| 2015/0110870 A1 | 4/2015 | Oshlack |
| 2015/0110879 A1 | 4/2015 | Wright |
| 2015/0118302 A1 | 4/2015 | Haswani |
| 2015/0118303 A1 | 4/2015 | Haswani |
| 2015/0140086 A1 | 5/2015 | Masselink |
| 2015/0140095 A1 | 5/2015 | Wright |
| 2015/0148366 A1 | 5/2015 | Whitelock |
| 2015/0148367 A1 | 5/2015 | Oshlack |
| 2015/0150978 A1 | 6/2015 | Kugelmann |
| 2015/0164808 A1 | 6/2015 | Shelby |
| 2015/0164811 A1 | 6/2015 | Bartholomaeus |
| 2015/0174121 A1 | 6/2015 | Oshlack |
| 2015/0182464 A1 | 7/2015 | Kugelmann |
| 2015/0182465 A1 | 7/2015 | Kugelmann |
| 2015/0182467 A1 | 7/2015 | Wright |
| 2015/0196555 A1 | 7/2015 | Guido |
| 2015/0196556 A1 | 7/2015 | Guido |
| 2015/0196557 A1 | 7/2015 | Guido |
| 2015/0202300 A1 | 7/2015 | Guido |
| 2015/0216809 A1 | 8/2015 | Oshlack |
| 2015/0216810 A1 | 8/2015 | Oshlack |
| 2015/0231086 A1 | 8/2015 | Wright |
| 2015/0231131 A1 | 8/2015 | Wright |
| 2015/0238418 A1 | 8/2015 | Oshlack |
| 2015/0246034 A1 | 9/2015 | Devarakonda |
| 2015/0250781 A1 | 9/2015 | Habib |
| 2015/0258086 A1 | 9/2015 | Hong |
| 2015/0258087 A1 | 9/2015 | Kao |
| 2015/0258088 A1 | 9/2015 | Kao |
| 2015/0258089 A1 | 9/2015 | Oshlack |
| 2015/0258090 A1 | 9/2015 | Oshlack |
| 2015/0265537 A1 | 9/2015 | Oshlack |
| 2015/0265596 A1 | 9/2015 | Lo |
| 2015/0265597 A1 | 9/2015 | Hong |
| 2015/0265598 A1 | 9/2015 | Hong |
| 2015/0265599 A1 | 9/2015 | McKenna |
| 2015/0265600 A1 | 9/2015 | McKenna |
| 2015/0265601 A1 | 9/2015 | McKenna |
| 2015/0290138 A1 | 10/2015 | Kugelmann |
| 2015/0297527 A1 | 10/2015 | Qi |
| 2015/0335580 A1 | 11/2015 | McKenna |
| 2015/0335582 A1 | 11/2015 | McKenna |
| 2015/0335583 A1 | 11/2015 | Huang |
| 2015/0335584 A1 | 11/2015 | Huang |
| 2015/0335585 A1 | 11/2015 | McKenna |
| 2016/0000703 A1 | 1/2016 | Micka |
| 2016/0008350 A1 | 1/2016 | Oshlack |
| 2016/0045449 A1 | 2/2016 | Lamson |
| 2016/0136152 A1 | 5/2016 | Baichwal |
| 2016/0184299 A1 | 6/2016 | Shelby |

(56) References Cited

U.S. PATENT DOCUMENTS

2016/0243041 A1 8/2016 Shelby
2016/0250203 A1 9/2016 Haswani
2016/0256392 A1 9/2016 Haswani

* cited by examiner

A

B

A

B

A

B

A

B

OPIOID ABUSE DETERRENT DOSAGE FORMS

CROSS REFERENCE TO RELATED APPLICATIONS

This application claims priority to U.S. Provisional Patent Application No. 62/238,385, filed on Oct. 7, 2015, and U.S. Provisional Patent Application No. 62/310,383, filed on Mar. 18, 2016, each of which are incorporated herein in its entirety by express reference thereto. This application is related to U.S. patent application Ser. No. 15/285,837 having the same title and contemporaneously filed on Oct. 5, 2016.

TECHNICAL FIELD

Described herein are oral abuse deterrent controlled release pharmaceutical compositions and methods for making the same. In particular, an oral abuse deterrent controlled release pharmaceutical composition comprising a soft capsule and an abuse deterrent controlled release matrix comprising an active pharmaceutical ingredient are described.

BACKGROUND

Increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse deterrent pharmaceutical compositions has become a high public health priority for the U.S. Food and Drug Administration (FDA). Prescription pharmaceutical compositions that are typically misused or abused fall, primarily, into three groups: (1) opioids prescribed for pain; (2) Central Nervous System (CNS) depressants prescribed for anxiety or sleep problems; and (3) stimulants, prescribed, for example, for attention deficit hyperactivity, narcolepsy, or obesity.

Methods for abusing prescription pharmaceutical compositions are varied and can include, for example, extraction, boiling, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, or administration as an anal or vaginal suppository. Alcohol-induced "dose dumping," i.e., the rapid release of active pharmaceutical ingredients in the presence of a solvent such as ethanol, is also an abuse concern and safety issue. Other methods include rapid extraction under aqueous boiling conditions.

There are a number of strategies for preventing the abuse of pharmaceuticals. Physical and chemical barriers can prevent the extraction of the drug or change the form of the drug making it less likely to be abused. Combinations of agonists and antagonists can be used, wherein the antagonist is only released upon product manipulation or tampering. Another strategy is to use aversive compounds that produce an unpleasant effect when the dosage form is tampered with. In addition, prodrugs can be used, which are only changed into the active form of the drug in the gastrointestinal tract. The pharmaceutical industry is utilizing these strategies to develop abuse-deterrent pharmaceutical compositions in order to reduce the potential for misuse of prescription pharmaceutical compositions.

Accordingly, there is a need for abuse deterrent pharmaceutical compositions that have controlled release properties.

SUMMARY

Described herein are pharmaceutical compositions comprising abuse deterrent controlled release matrices comprising active pharmaceutical ingredients. The matrix is structured to prevent extraction of the active pharmaceutical ingredients. Specifically, the matrix formulations described herein minimize the likelihood of tampering, "dose dumping," or the extraction of active pharmaceutical ingredients from the composition. In particular, there is a need for formulations that are resistant to active pharmaceutical ingredient extraction under boiling conditions.

One embodiment described herein is an oral abuse deterrent pharmaceutical composition comprising a tamper resistant controlled release matrix, wherein the tamper resistant controlled release matrix comprises a means for preventing the crushing, grating, grinding, cutting, solvating, or dissolving of the tamper resistant controlled release matrix comprising one or more active pharmaceutical ingredients.

Another embodiment described herein is an abuse deterrent oral pharmaceutical composition comprising a tamper resistant controlled release composition comprising: (a) one or more flowability enhancers; (b) one or more release modifiers; and (c) one or more active pharmaceutical ingredients; wherein the matrix is resistant to tampering.

One embodiment described herein is a pharmaceutical composition comprising: (a) one or more flowability enhancers; (b) one or more release modifiers; and (c) one or more active pharmaceutical ingredients. In one aspect, the composition further comprises one or more antioxidants. In another aspect, the composition further comprises one or more viscosity modifiers. In another aspect, the flowability enhancer comprises about 35% to about 70% of the composition by mass. In another aspect, the release modifier comprises about 20% to about 50% of the composition by mass. In another aspect, the active pharmaceutical ingredient comprises about 0.5% to about 35% of the composition by mass. In another aspect, the antioxidant comprises about 0.05% to about 0.5% of the composition by mass. In another aspect, the viscosity modifier comprises about 0.5% to about 10% of the composition by mass. In another aspect, the ratio of the active pharmaceutical ingredient mass to the composition mass comprises a range of about 1:1000 to about 1:3. In another aspect, a ratio of release modifier to flowability enhancer is about 1:2. In another aspect, a ratio of active pharmaceutical ingredient to release modifier comprises a range of about 1:1 to about 1:20. In another aspect, the flowability enhancer comprises a non-ionic surfactant, an anionic surfactant, a zwitterionic surfactant, a cationic surfactant, or a combination thereof. In another aspect, the flowability enhancer comprises a non-ionic surfactant. In another aspect, the flowability enhancer comprises a hydrophilic lipophilic balance of less than about 5. In another aspect, the flowability enhancer comprises a medium chain mono-, di-, or tri-glyceride; or a liquid lipophilic vehicle. In another aspect, the flowability enhancer comprises glyceryl monocaprylate, glyceryl monocaprylcaprate, glyceryl monolinoleate, oleic acid, or a combination thereof. In another aspect, the release modifier comprises polyethylene oxide, a carboxyvinyl polymer, or a combination thereof. In another aspect, the release modifier comprises a polyethylene oxide having a molecular weight ($M_v$) of about 1,000,000; about 2,000,000; about 3,000,000; about 4,000,000; about 5,000,000; about 6,000,000; about 7,000,000; about 8,000,000; about 9,000,000; or about 10,000,000. In another aspect, the release modifier comprises a polyethylene oxide having a molecular weight ($M_v$) of about 4,000,000. In another aspect, the viscosity modifier comprises polyvinyl pyrrolidone, ethylcellulose, or a combination thereof. In another aspect, the antioxidant comprises alpha-tocopherol, beta-tocopherol, gamma-tocopherol, delta-tocopherol, butylated hydroxyanisole (BHA), butylated hydroxytoluene (BHT), citric acid, ascorbic acid, carnosic acid, carnosol, rosmanol, epirosmanol, isorosmanol, methyl carnosate, rosmarinic acid, eugenol, eugenyl acetate, clove bud extract, methanolic extract, epigallocatechin gallate, epicatechin gallate, epigallocatechin, epicatechin, or a combination thereof. In another aspect, the composition forms an elastic, semi-solid composition after being heated at a temperature of about 50° C. to about 80° C. for a time period of about 10 min to about 180 min and then cooling the composition to room temperature. In another aspect, the active pharmaceutical ingredient comprises an opioid agonist. In another aspect, the active pharmaceutical ingredient comprises oxycodone, hydrocodone, oxymorphone, hydromorphone, morphine, codeine, methadone, fentanyl, tapentadol, tramadol, meperidine, propoxyphene, flunitrazepam, barbiturates, amytal, nembutal, seconal, phenobarbital; benzodiazepines, zolpidem, zaleplon, eszopiclone, amphetamines, methylphenidate, a salt thereof, or a combination thereof. In another aspect, the active pharmaceutical ingredient comprises oxycodone or a pharmaceutically acceptable salt thereof. In another aspect, the active pharmaceutical ingredient comprises oxycodone hydrochloride or oxycodone myristate. In another aspect, the active pharmaceutical ingredient comprises oxycodone hydrochloride comprising >25 ppm of 14-hydroxycodeinone. In another aspect, the active pharmaceutical ingredient comprises about 5 mg to about 120 mg of oxycodone hydrochloride. In another aspect, the active pharmaceutical ingredient comprises about 5 mg, about 10 mg, about 15 mg, about 20 mg, about 30 mg, or about 40 mg of oxycodone hydrochloride.

In one embodiment described herein, the composition comprises: (a) about 35% to about 70% by mass of one or more flowability enhancers; (b) about 20% to about 50% by mass of one or more release modifiers; and (c) about 1% to about 30% by mass of one or more active pharmaceutical ingredients. In one aspect, the composition further comprises: (d) about 0.05% to about 0.5% of one or more antioxidants. In another aspect, the composition comprises: (a) glyceryl monolinoleate; (b) polyethylene oxide; and (c) oxycodone hydrocloride. In another aspect, the composition further comprises: (d) butylated hydroxytoluene (BHT); and (e) butylated hydroxyanisole (BHA). In another aspect, the composition comprises: (a) about 50% to about 70% by mass of glyceryl monolinoleate; (b) about 25% to about 40% by mass of polyethylene oxide; and (c) about 1% to about 20% by mass of oxycodone hydrochloride. In another aspect, the composition further comprises: (d) about 0.05% to about 0.4% by mass of BHA; and (e) about 0.05% to about 0.2% by mass of BHT. In another aspect, the composition comprises: (a) about 55% to about 65% by mass of glyceryl monolinoleate; (b) about 30% to about 35% by mass of polyethylene oxide; and (c) about 1% to about 15% by mass of oxycodone hydrocloride. In another aspect, the composition further comprises: (d) about 0.1% to about 0.4% by mass of BHA; and (e) about 0.05% to about 0.1% by mass of BHT. In another aspect, the composition comprises: (a) about 50% to about 70% by mass of glyceryl monolinoleate; (b) about 25% to about 40% by mass of polyethylene oxide; (c) about 0.1% to about 0.4% by mass of BHA; (d) about 0.05% to about 0.1% by mass of BHT; and (e) about 1% to about 20% of by mass of oxycodone hydrocloride.

Another embodiment described herein is an oral abuse deterrent pharmaceutical composition comprising: (a) about 50% to about 70% by mass glyceryl monolinoleate; (b) about 25% to about 40% by mass polyethylene oxide comprising a molecular weight of about 4,000,000; and (c) about 1% to about 20% by mass of oxycodone hydrochloride; and wherein the composition forms an abuse deterrent elastic semi-solid composition after being heated at a temperature of about 50° C. to about 80° C. for a time period of about 10 min to about 180 min and then cooling the composition to room temperature. In one aspect, the active pharmaceutical ingredient comprises about 5 mg, about 10 mg, about 15 mg, about 20 mg, about 30 mg, or about 40 mg of oxycodone hydrochloride. In another aspect, the composition is encapsulated in a capsule. In another aspect, the composition is encapsulated in a soft capsule. In another aspect, the soft capsule comprises one or more film forming polymers, one or more plasticizers, one or more solvents, and optionally: one or more opacifying agents, one or more coloring agents, one or more pharmaceutical excipients, or combination thereof. In another aspect, the soft capsule comprises: (a) about 25% to about 50% of one or more film-forming polymers; (b) about 15% to about 25% of one or more plasticizers; (c) about 20% to about 40% of one or more solvents; and (d) optionally, one or more opacifying agents, one or more coloring agents, one or more pharmaceutical excipients, or combination thereof. In another aspect, the soft capsule comprises gelatin, glycerol, water, and optionally, titanium oxide, and/or a coloring agent. In another aspect, the soft capsule is coated with one or more coatings. In another aspect, the coating comprises polyvinyl alcohol. In another aspect, the coating comprises about 5% to about 15% of weight gain to the dosage form. In another aspect, the coating thickness is about 150 μm to about 200 μm.

Another embodiment described herein is a method for manufacturing a tamper resistant, abuse deterrent dosage form comprising: (a) combining one or more flowability enhancers, one or more viscosity modifiers, and one or more active pharmaceutical ingredients; (b) encapsulating the composition into capsules; (c) incubating the capsules at an elevated temperature for a period of time; and (d) cooling the capsules to room temperature. In one aspect, the capsules produced in step (b) are coated with a coating prior to the annealing of step (c). In another aspect, the capsules are incubated in step (c) at about 50° C. to about 80° C. for about 10 min to about 180 min. In another aspect, the capsules are cooled in step (d) by reducing the temperature at a rate of about 2° C. to about 10° C. per about 5 to about 15 min (e.g., a decrease of about 5° C. every 10 min).

Another embodiment described herein is an oral tamper resistant dosage form produced by any of the methods described herein comprising oxycodone hydrochloride.

Another embodiment described herein is an oral abuse deterrent controlled release dosage form comprising a capsule encapsulating: (a) about 50% to about 70% by mass glyceryl monolinoleate; (b) about 25% to about 40% by mass polyethylene oxide comprising a molecular weight of about 4,000,000; and (c) about 1% to about 20% by mass of oxycodone hydrochloride; and the dosage form having been heated to about 50° C. to about 80° C. for about 10 min to about 180 min, and cooled to room temperature by reducing the temperature at a rate of about 2° C. to about 10° C. per about 5 to about 15 min. In another aspect, the dosage form exhibits an in vitro dissolution rate at pH 1.2 of about 50% after about 90 min. In another aspect, the pharmaceutical dosage form exhibits an in vitro dissolution rate in water under boiling conditions of less than about 35% to about 60% after about 10 minutes to about 45 minutes. In another aspect, the pharmaceutical composition exhibits an in vitro dissolution rate in an aqueous alcohol solution or distilled water of less than about 20% to about 50% after about 30 minutes to about 360 minutes.

Another embodiment described herein is a method for treating, reducing the symptoms of, or retarding the onset of pain comprising administering to a subject in need thereof of an oral pharmaceutical composition comprising glyceryl monolinoleate, polyethylene oxide, and oxycodone. In one aspect, in the pharmaceutical composition comprises: (a) about 50% to about 70% by mass glyceryl monolinoleate; (b) about 25% to about 40% by mass polyethylene oxide; and (c) about 1% to about 20% by mass of oxycodone hydrochloride. In another aspect, the pain arises from one or more of diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, granuloma annulare, trauma, cancer, or a combination thereof.

Another embodiment described herein is a method for delivering about 10 mg to about 120 mg of oxycodone comprising administering to a subject one or more doses of a pharmaceutical composition comprising glyceryl monolinoleate, polyethylene oxide, and oxycodone, the method capable of achieving one or more of the following pharmacokinetic parameters: (a) a mean plasma oxycodone $T_{max}$ of about 1 hours to about 8 hours; (b) a mean plasma oxycodone $C_{max}$ of about 10 ng/mL to about 150 ng/mL; or (c) a mean plasma oxycodone $AUC_{0\to\infty}$ of about 100 h·ng/mL to about 1000 h·ng/mL.

Another embodiment described herein is a method for delivering about 40 mg of oxycodone comprising administering to a subject one or more dosage forms comprising glyceryl monolinoleate, polyethylene oxide, and oxycodone, the method capable of achieving one or more of the following pharmacokinetic parameters: (a) a mean plasma oxycodone $T_{max}$ of about 4.5 hours to about 5.0 hours; (b) a mean plasma oxycodone $C_{max}$ of about 40 ng/mL to about 65 ng/mL; (c) a mean plasma oxycodone $AUC_{0\to\tau}$ of about 400 h·ng/mL to about 500 h·ng/mL; (d) a mean plasma oxycodone $AUC_{0\to\infty}$ of about 400·h·ng/mL to about 500 h·ng/mL; (e) a mean oxycodone half-life (t½) of about 4.4 hours to about 4.6 hours; or (f) a mean oxycodone overall elimination rate constant ($\lambda_z$) of about 0.14 $h^{-1}$ to about 0.17 $h^{-1}$. In one aspect, the pharmaceutical dosage form exhibits an in vitro dissolution rate at pH 1.2 of about 50% after about 90 minutes.

Another embodiment described herein is a method for inhibiting extraction of oxycodone from a pharmaceutical composition, the method comprising: providing a dosage form as described herein, wherein the dosage form is resistant to crushing, grating, grinding, cutting, solvation, or dissolution in water or alcohol. In one aspect, the pharmaceutical composition comprises a coated soft capsule.

Another embodiment described herein is an oral abuse deterrent controlled release pharmaceutical composition comprising glyceryl monolinoleate, polyethylene oxide, and oxycodone, the composition having been heated to about 50° C. to about 80° C. for about 10 min to about 180 min, and cooled to room temperature, wherein the abuse deterrent controlled release pharmaceutical composition comprises a means for inhibiting the crushing, grating, grinding, cutting, solvating, or dissolving of the composition.

Another embodiment described herein is a kit for dispensing an abuse deterrent dosage form comprising: (a) one or more dosage forms as described herein; (b) one or more receptacles comprising a tamper evident, moisture proof packaging that reduces the ability of removing the dosage form comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and (c) optionally, an insert comprising instructions or prescribing information for the dosage form.

One embodiment described herein is an oral pharmaceutical composition comprising: (a) glyceryl monolinoleate; (b) polyethylene oxide; and (c) oxycodone or a salt thereof. In one aspect, the composition forms an abuse deterrent elastic semi-solid composition after being heated at a temperature of about 50° C. to about 80° C. for a time period of about 10 min to about 180 min and then cooling the composition to room temperature. In another aspect, a ratio of polyethylene oxide to glyceryl monolinoleate is about 1:2. In another aspect, a ratio of oxycodone to polyethylene oxide comprises a range of about 1:1 to about 1:15. In another aspect, the glyceryl monolinoleate comprises about 35% to about 70% of the composition by mass. In another aspect, the polyethylene oxide comprises about 20% to about 50% of the composition by mass. In another aspect, the oxycodone comprises about 1% to about 30% of the composition by mass. In another aspect, the composition further comprises one or more antioxidants. In another aspect, the antioxidant comprises about 0.05% to about 0.5% of the composition by mass. In another aspect, the antioxidant comprises butylated hydroxyanisole (BHA), butylated hydroxytoluene (BHT), or a combination thereof. In another aspect, the polyethylene oxide comprises a polyethylene oxide having a molecular weight $M_v$ of about 1,000,000 to about 7,000,000. In another aspect, the polyethylene oxide comprises a polyethylene oxide having an average molecular weight ($M_v$) of about 4,000,000. In another aspect, the oxycodone comprises oxycodone hydrochloride or oxycodone myristate. In another aspect, the oxycodone comprises about 5 mg to about 120 mg of oxycodone hydrochloride. In another aspect, the oxycodone comprises about 5 mg, about 10 mg, about 15 mg, about 20 mg, about 30 mg, or about 40 mg of oxycodone hydrochloride.

In another embodiment, the composition comprises: (a) about 35% to about 70% by mass of glyceryl monolinoleate; (b) about 20% to about 50% by mass of polyethylene oxide; and (c) about 1% to about 30% by mass of oxycodone hydrochloride. In one aspect, the composition further comprises: (d) about 0.1% to about 0.4% by mass of BHA; and (e) about 0.05% to about 0.1% by mass of BHT. In another aspect, the composition comprises: (a) about 50% to about 70% by mass of glyceryl monolinoleate; (b) about 25% to about 40% by mass of polyethylene oxide; (c) about 0.1% to about 0.4% by mass of BHA; (d) about 0.05% to about 0.1% by mass of BHT; and (e) about 1% to about 20% of by mass of oxycodone hydrochloride.

Another embodiment described herein is an oral abuse deterrent controlled release dosage form comprising a capsule encapsulating: (a) about 50% to about 70% by mass glyceryl monolinoleate; (b) about 25% to about 40% by mass polyethylene oxide comprising an average molecular weight ($M_v$) of about 4,000,000; and (c) about 1% to about 20% by mass of oxycodone hydrochloride; and the dosage form having been heated to about 50° C. to about 80° C. for about 10 min to about 180 min, and cooled to room temperature by reducing the temperature at a rate of about 2° C. to about 10° C. over about 5 to about 15 min (e.g., a decrease of about 5° C. every 10 min). In one aspect, the oxycodone hydrochloride comprises about 5 mg, about 10 mg, about 15 mg, about 20 mg, about 30 mg, or about 40 mg of oxycodone hydrochloride. In another aspect, the capsule is coated with a polyvinyl alcohol coating. In another aspect, the dosage form exhibits an in vitro dissolution rate at pH 1.2 of about 50% after about 90 minutes. A method for treating, reducing the symptoms of, or retarding onset of pain comprising administering to a subject in need thereof a dosage form as described herein.

Another embodiment described herein is a method for inhibiting extraction of oxycodone from a pharmaceutical composition, the method comprising: providing a dosage form as described herein, wherein the dosage form is resistant to crushing, grating, grinding, cutting, solvation, or dissolution in water or alcohol.

Another embodiment described herein is a kit for dispensing an abuse deterrent dosage form comprising: (a) one or more dosage forms as described herein; (b) one or more receptacles comprising a tamper evident, moisture proof packaging that reduces the ability of removing the dosage form comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and (c) optionally, an insert comprising instructions or prescribing information for the dosage form.

Another embodiment described herein is a method for manufacturing an abuse deterrent dosage form comprising: (a) combining glyceryl monolinoleate, polyethylene oxide, and oxycodone; (b) encapsulating the combination into capsules; (c) incubating the capsules at an elevated temperature for a period of time; and (d) cooling the capsules to room temperature. In one aspect, the capsules produced in step (b) are coated with a coating prior to the incubating of step (c). In another aspect, the capsules are incubated in step (c) at about 50° C. to about 80° C. for about 10 min to about 180 min. In another aspect, the capsules are cooled in step (d) by reducing the temperature at a rate of about 2° C. to about 10° C. over about 5 to about 15 min (e.g., a decrease of about 5° C. every 10 min).

Another embodiment described herein is a method for treating pain comprising administering to a subject a pharmaceutical dosage form comprising glyceryl monolinoleate, polyethylene oxide, and about 40 mg oxycodone, the method capable of achieving one or more of the following pharmacokinetic parameters: (a) a mean plasma oxycodone $T_{max}$ of about 4.5 hours to about 5.0 hours; (b) a mean plasma oxycodone $C_{max}$ of about 40 ng/mL to about 65 ng/mL; (c) a mean plasma oxycodone $AUC_{0 \to \tau}$ of about 400 h·ng/mL to about 500 h·ng/mL; (d) a mean plasma oxycodone $AUC_{0 \to \infty}$ of about 400·h·ng/mL to about 500 h·ng/mL; (e) a mean oxycodone half-life (t½) of about 4.4 hours to about 4.6 hours; or (f) a mean oxycodone overall elimination rate constant ($\lambda_z$) of about 0.14 h$^{-1}$ to about 0.17 h$^{-1}$. In one aspect, the pharmaceutical dosage form exhibits an in vitro dissolution rate at pH 1.2 of about 50% after about 90 minutes.

Another embodiment described herein is an abuse deterrent oral pharmaceutical composition comprising a tamper resistant controlled release composition comprising: (a) one or more flowability enhancers; (b) one or more release modifiers; and (c) one or more active pharmaceutical ingredients; wherein the matrix is resistant to tampering. In one aspect described herein, the tamper resistant controlled release matrix further comprises at least one antioxidant. In another aspect described herein, the tamper resistant controlled release matrix further comprises at least one or more viscosity modifiers. In another aspect described herein, the one or more flowability enhancers comprise about 35% to about 70% of the total matrix mass. In another aspect described herein, the at least one or more release modifiers comprise from about 20% to about 50% of the total matrix mass. In another aspect described herein, the at least one active pharmaceutical ingredient comprise about 0.1% to about 35% of the total matrix mass. In another aspect described herein, the at least one antioxidant comprises about 0.05% to about 0.5% of the total matrix mass. In another aspect described herein, the at least one or more viscosity modifiers comprise about 0.5% to about 8% of the total matrix mass. In another aspect described herein, the ratio of the active pharmaceutical ingredient percent mass to the matrix percent mass is about 1:1000 to about 1:3. In another aspect described herein, the one or more flowability enhancers comprises a non-ionic surfactant, an anionic surfactant, a zwitterionic surfactant, or a cationic surfactant or a combination thereof. In another aspect described herein, the one or more flowability enhancers comprises a non-ionic surfactant. In another aspect described herein, the one or more flowability enhancers have a hydrophilic lipophilic balance of less than about 5. In another aspect described herein, the one or more flowability enhancers comprise a medium chain mono-, di-, or tri-glyceride; or a liquid lipophilic vehicle. In another aspect described herein, the one or more flowability enhancers comprise glyceryl monocaprylate, glyceryl monocaprylcaprate, glyceryl monolinoleate, or oleic acid. In another aspect described herein, the one or more release modifiers comprise a high molecular weight polyethylene oxide. In another aspect described herein, the one or more release modifiers comprises a polyethylene oxide having, a carboxyvinyl polymer or a mixture thereof. In another aspect described herein, the molecular weight of the polyethylene oxide is about 5,000,000; about 6,000,000, about 7,000,000, about 8,000,000, about 9,000,000, or about 10,000,000. In another aspect described herein, the one or more viscosity modifiers comprises polyvinyl pyrrolidone or ethylcellulose, or a mixture thereof. In another aspect described herein, the antioxidant comprises alpha-tocopherol, beta-tocopherol, gamma-tocopherol, delta-tocopherol, butylated hydroxytoluene (BHT), butylated hydroxyanisole (BHA), citric acid, ascorbic acid, carnosic acid, carnosol, rosmanol, epirosmanol, isorosmanol, methyl carnosate, rosmarinic acid, eugenol, eugenyl acetate, clove bud extract, methanolic extract, epigallocatechin gallate, epicatechin gallate, epigallocatechin, epicatechin, or a combination thereof. In another aspect described herein, the tamper resistant controlled release matrix forms a semi-solid elastic composition after being heated at a temperature of about 50° C. to about 90° C. for a period of time of about 0.1 hours to about 3 hours. In another aspect described herein, the active pharmaceutical ingredient comprises at least one of: hydrocodone, morphine, morphine analogues, or morphine antagonists, tapentadol, codeine, morphine, methadone, fentanyl and analogs: hydrocodone hydrochloride, hydrocodone bitartrate, hydromorphone, oxymorphone, oxycodone, meperidine, propoxyphene, flunitrazepam, barbiturates, amytal, nembutal, seconal, phenobarbital; benzodiazepines, zolpidem, zaleplon, eszopiclone, amphetamines, methylphenidate, or a combination thereof. In another aspect described herein, the active pharmaceutical ingredient comprises oxycodone or any pharmaceutically acceptable salt thereof.

In another embodiment described herein, the active pharmaceutical ingredient comprises oxycodone and a second active pharmaceutical ingredient that reduces the symptoms of, or onset of, or prophylaxis, of a bowel dysfunction due to acute or chronic opioid use. In another aspect described herein, the second active pharmaceutical ingredient comprises a peripherally acting mu-opioid receptor antagonist comprising methylnaltrexone, naltrexone, naloxone, naloxegol, alvimopan or a combination thereof. In another aspect described herein, the peripherally acting mu-opioid receptor antagonist comprises methylnaltrexone, naltrexone, naloxone or a combination thereof. In another aspect described herein, the peripherally acting mu-opioid receptor antagonist comprises naloxone. In another aspect described herein, the active pharmaceutical ingredient comprises naloxone and oxycodone. In another aspect described herein, the at least one active pharmaceutical ingredient comprises naltrexone and oxycodone.

In another embodiment described herein, the tamper resistant controlled release matrix comprises: (a) glyceryl monocaprylate, oleic acid, or glyceryl monolinoleate; (b) polyethylene oxide; and (c) oxycodone; and optionally one or more of (d) a carboxyvinyl polymer; (e) BHT; and (f) BHA. In one aspect, the tamper resistant controlled release matrix further comprises polyvinylpyrrolidone or ethylcellulose. In another aspect described herein, the tamper resistant controlled release matrix comprises: (a) about 50% to about 65% mono- and di-glycerides (e.g., Capmul® MCM), oleic acid, or glyceryl monolinoleate; (b) about 25% to about 35% polyethylene oxide having a molecular weight of about 4,000,000 or about 7,000,000; and (c) about 2% to about 10% of oxycodone; and optionally (d) about 1% of carboxyvinyl polymer (e.g., Carbopol® 974P); (e) about 0.25% BHT; and (f) about 0.1% BHA. In another aspect, the tamper resistant controlled release matrix further comprises about 1% to about 5% of polyvinylpyrrolidone K90 or about 1% to about 5% ethylcellulose 20 cP (e.g., Ethocel™ 20 cP). In another aspect described herein, the tamper resistant controlled release matrix further comprises a peripherally acting mu-opioid receptor antagonist comprising naloxone, methyl naltrexone, or naltrexone. In another aspect described herein, the weight percentage ratio of naloxone methyl naltrexone or naltrexone to oxycodone is about 15:1 to about 1:18. In another aspect described herein, the weight percentage ratio of naloxone to oxycodone is about 1:2.

In another embodiment described herein, the capsule shell comprises a soft capsule shell. In another embodiment described herein, the capsule shell comprises a hard capsule shell.

In another embodiment described herein the soft capsule shell comprises a film forming polymer, a plasticizer, a solvent, and optionally, an opacifying agent, a coloring agent, or a pharmaceutical excipient.

In one aspect described herein, the soft capsule shell comprises: (a) about 25% to about 50% of at least one film-forming polymer; (b) about 15% to about 25% of at least one plasticizer; (c) about 20% to about 40% of a solvent; (d) optionally, an opacifying agent, a coloring agent, a pharmaceutical excipient, or combination thereof. In another aspect described herein, the soft capsule shell comprises: (a) about 42% of at least one film-forming polymer; (b) about 20% of at least one plasticizer; (c) about 38% of a solvent; (d) optionally, about 0.7% of an opacifying agent; and (e) optionally, about 0.1% at least one coloring agent. In another aspect described herein, the soft capsule shell comprises gelatin, glycerol, water, and optionally, titanium oxide, and a coloring agent.

Another embodiment described herein is a method of making the tamper resistant controlled release matrix dosage form as described herein comprising the steps of (a) suspending one or more release modifiers in one or more flowability enhancers to form a first mixture and (b) adding one or more active pharmaceutical ingredients to the first mixture to form a matrix mixture that may be encapsulated in a soft capsule shell or a hard capsule shell. In one aspect, step (a) further comprises dissolving one or more viscosity modifiers in the one or more flowability enhancers.

Another embodiment described herein is a method for manufacturing a soft capsule shell and a tamper resistant controlled release matrix comprising: (a) providing a matrix comprising the composition as described herein made by the methods of manufacturing described herein; (b) providing a soft capsule gel mass described herein; (c) casting the soft capsule gel mass into films using heat-controlled drums or surfaces; (d) forming a soft capsule comprising the matrix composition using rotary die encapsulation technology; and (e) heating the formed capsules for about 1 hour at about 70° C. to form an annealed soft capsule shell, wherein following heating, the matrix has tamper resistant controlled release properties.

Another embodiment described herein is a soft or hard capsule comprising a tamper resistant controlled release matrix produced by the methods described herein.

Another embodiment described herein is an enteric soft capsule comprising a tamper resistant controlled release matrix produced by the method described herein.

Another embodiment described herein is a tamper resistant oral pharmaceutical composition comprising a tamper resistant controlled release matrix comprising: (a) about 50% to about 65% mono- and di-glycerides (e.g., Capmul® MCM); (b) about 25% to about 35% polyethylene oxide having a molecular weight of about 4,000,000 or about 7,000,000; and (c) about 2% to about 10% of oxycodone; and optionally (d) about 1% of carboxyvinyl polymer (e.g., Carbopol® 974P); (e) about 0.25% BHT; and (f) about 0.1% BHA; wherein the matrix is resistant to tampering and has controlled release properties; the matrix being encapsulated in a soft capsule shell comprising: (g) about 25% to about 50% gelatin; (h) about 15% to about 25% glycerol; (i) about 20% to about 40% water; and (j) optionally, an opacifying agent, a coloring agent, a pharmaceutical excipient, or combination thereof. In one aspect described herein, the tamper resistant controlled release matrix further comprises a peripherally acting mu-opioid receptor antagonist comprising naloxone, methyl naltrexone, or naltrexone. In another aspect described herein, the weight percentage ratio of naloxone, methyl naltrexone or naltrexone to oxycodone is about 15:1 to about 1:18. In another aspect described herein, the weight percentage ratio of naloxone to oxycodone is about 1:2.

Another embodiment described herein is a tamper resistant oral pharmaceutical composition comprising a tamper resistant controlled release matrix comprising: (a) about 50% to about 65% mono- and di-glycerides (e.g., Capmul® MCM); (b) about 25% to about 35% polyethylene oxide having a molecular weight of about 4,000,000 or about 7,000,000; and (c) about 10% of oxycodone; (g) about 1% to about 5% of naloxone; and optionally (d) about 1% of carboxyvinyl polymer (e.g., Carbopol® 974P); (e) about 0.25% BHT; and (f) about 0.1% BHA; wherein the matrix is resistant to tampering and has controlled release properties; the matrix being encapsulated in a soft capsule shell comprising: (g) about 25% to about 50% gelatin; (h) about 15% to about 25% glycerol; (i) about 20% to about 40% water; and (j) optionally, an opacifying agent, a coloring agent, a pharmaceutical excipient, or combination thereof.

Another embodiment described herein is a tamper resistant oral pharmaceutical composition comprising a tamper resistant controlled release matrix comprising: (a) about 50% to about 65% mono- and di-glycerides (e.g., Capmul® MCM); (b) about 25% to about 35% polyethylene oxide having a molecular weight of about 4,000,000 or about 7,000,000; (c) about 1% to about 5% polyvinylpyrrolidone K90 (d) about 2% to about 10% of oxycodone; and optionally (e) about 0.25% BHT; and (f) about 0.1% BHA; wherein the matrix is resistant to tampering and has controlled release properties; the matrix being encapsulated in a soft capsule shell comprising: (g) about 25% to about 50% gelatin; (h) about 15% to about 25% glycerol; (i) about 20% to about 40% water; and (j) optionally, an opacifying agent, a coloring agent, a pharmaceutical excipient, or combination thereof.

Another embodiment described herein is a tamper resistant oral pharmaceutical composition comprising a tamper resistant controlled release matrix comprising: (a) about 50% to about 65% oleic acid; (b) about 25% to about 35% polyethylene oxide having a molecular weight of about 4,000,000 or about 7,000,000; (c) about 1% to about 5% ethylcellulose 20 cP (e.g., Ethocel™ 20 cP); (d) about 2% to about 10% of oxycodone; and optionally (e) about 0.25% BHT; and (f) about 0.1% BHA; wherein the matrix is resistant to tampering and has controlled release properties; the matrix being encapsulated in a soft capsule shell comprising: (g) about 25% to about 50% gelatin; (h) about 15% to about 25% glycerol; (i) about 20% to about 40% water; and (j) optionally, an opacifying agent, a coloring agent, a pharmaceutical excipient, or combination thereof.

Another embodiment described herein is a tamper resistant oral pharmaceutical composition comprising a tamper resistant controlled release matrix comprising: (a) about 50% to about 65% glyceryl monolinoleate (e.g., Maisine™ 35-1); (b) about 25% to about 35% polyethylene oxide having a molecular weight of about 4,000,000 or about 7,000,000; and (c) about 2% to about 10% of oxycodone; and optionally (e) about 0.25% BHT; and (f) about 0.1% BHA; wherein the matrix is resistant to tampering and has controlled release properties; the matrix being encapsulated in a soft capsule shell comprising: (g) about 25% to about 50% gelatin; (h) about 15% to about 25% glycerol; (i) about 20% to about 40% water; and (j) optionally, an opacifying agent, a coloring agent, a pharmaceutical excipient, or combination thereof.

Another embodiment described herein is a method for treating, reducing the symptoms or onset of, or prophylaxis of pain stemming from diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica or granuloma annulare comprising administering to a subject in need thereof the pharmaceutical composition as described herein. In one aspect described herein, the administration is sufficient to achieve a reduction of pain relative to baseline in the subject without substantially inducing one or more of opioid induced bowel disfunction (OIBD) comprising constipation (opioid induced constipation; OIC), anorexia, nausea and vomiting, gastro-oesophageal reflux, delayed digestion, abdominal pain, flatulence, bloating, hard stools, incomplete evacuation or straining during bowel movements.

Another embodiment described herein is a method for delivering about a 10 mg to about 80 mg dose of oxycodone comprising administering to a subject a pharmaceutical composition comprising oxycodone and other pharmaceutically acceptable excipients in a tamper resistant matrix in a soft gel capsule, the method capable of achieving one or more of the following pharmacokinetic parameters: (a) a mean plasma oxycodone $T_{max}$ of about 1 hours to about 8 hours; (b) a mean plasma oxycodone $C_{max}$ of about 10 ng/mL to about 150 ng/mL; (c) a mean plasma oxycodone $AUC_{0 \to \infty}$ of about 100 h·mg/L to about 1000 h·mg/L.

In one aspect described herein, the method further comprises delivering a dose of a peripherally acting mu-opioid receptor antagonist comprising naloxone, methyl naltrexone, or naltrexone. In another aspect described herein, the weight percentage ratio of naloxone methyl naltrexone or naltrexone to oxycodone is about 15:1 to about 1:18. In another aspect described herein, the weight percentage ratio of naloxone to oxycodone is about 1:2.

In another aspect described herein, the administration of the compositions described herein is sufficient to achieve a reduction of pain relative to baseline in the subject without substantially inducing one or more of opioid induced bowel disfunction (OIBD) comprising constipation (opioid induced constipation), anorexia, nausea and vomiting, gastro-oesophageal reflux, delayed digestion, abdominal pain, flatulence, bloating, hard stools, incomplete evacuation, or straining during bowel movements.

In another aspect described herein, the administration of the compositions described herein provides an improvement of bowel function during pain therapy, comprising an improvement of the mean bowel function score of at least about 5, at least about 8, at least about 10, or at least about 15 after steady state administration to human patients, wherein the mean bowel function score is measured with a numerical analog scale ranging from 0 to 100. In another aspect described herein, the pharmaceutical composition comprises the tamper resistant controlled release matrix as described herein.

In another aspect described herein, the pharmaceutical composition exhibits an in vitro dissolution rate at pH 1.2, of about 35% to about 95% after about 60 minutes to about 480 minutes. In another aspect described herein, the pharmaceutical composition exhibits an in vitro dissolution rate at pH 1.2, of less than about 20% after about 60 minutes to about 480 minutes. In another aspect described herein, the pharmaceutical composition exhibits an in vitro dissolution rate under boiling conditions of less than about 35% to about 60% after about 10 minutes to about 45 minutes. In another aspect described herein, the pharmaceutical composition exhibits an in vitro dissolution rate in an aqueous alcohol solution or distilled water of less than about 20% to about 50% after about 30 minutes to about 360 minutes.

Another embodiment described herein is method for reducing the ability of a subject to extract an active pharmaceutical ingredient from a pharmaceutical composition though crushing, grating, grinding, cutting, or solvating or dissolving the matrix comprising: providing the abuse deterrent composition as described herein, wherein the composition is resistant to crushing, grating, grinding, cutting, solvation, or dissolution. In one aspect described herein, the pharmaceutical composition comprises a soft capsule shell or hard capsule shell as described herein.

Another embodiment described herein is an abuse deterrent oral pharmaceutical composition comprising a tamper resistant controlled release matrix, wherein the tamper resistant controlled release matrix comprises a means for preventing the crushing, grating, grinding, cutting, solvating, or dissolving of the tamper resistant controlled release matrix comprising one or more active pharmaceutical ingredients.

Another embodiment described herein is a kit for dispensing the abuse deterrent oral pharmaceutical composition described herein comprising: (a) at least one soft capsule comprising a tamper resistant controlled release matrix comprising an active pharmaceutical ingredient; (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and (c) optionally, an insert comprising instructions or prescribing information for the active pharmaceutical ingredient.

DETAILED DESCRIPTION

Figure 1:
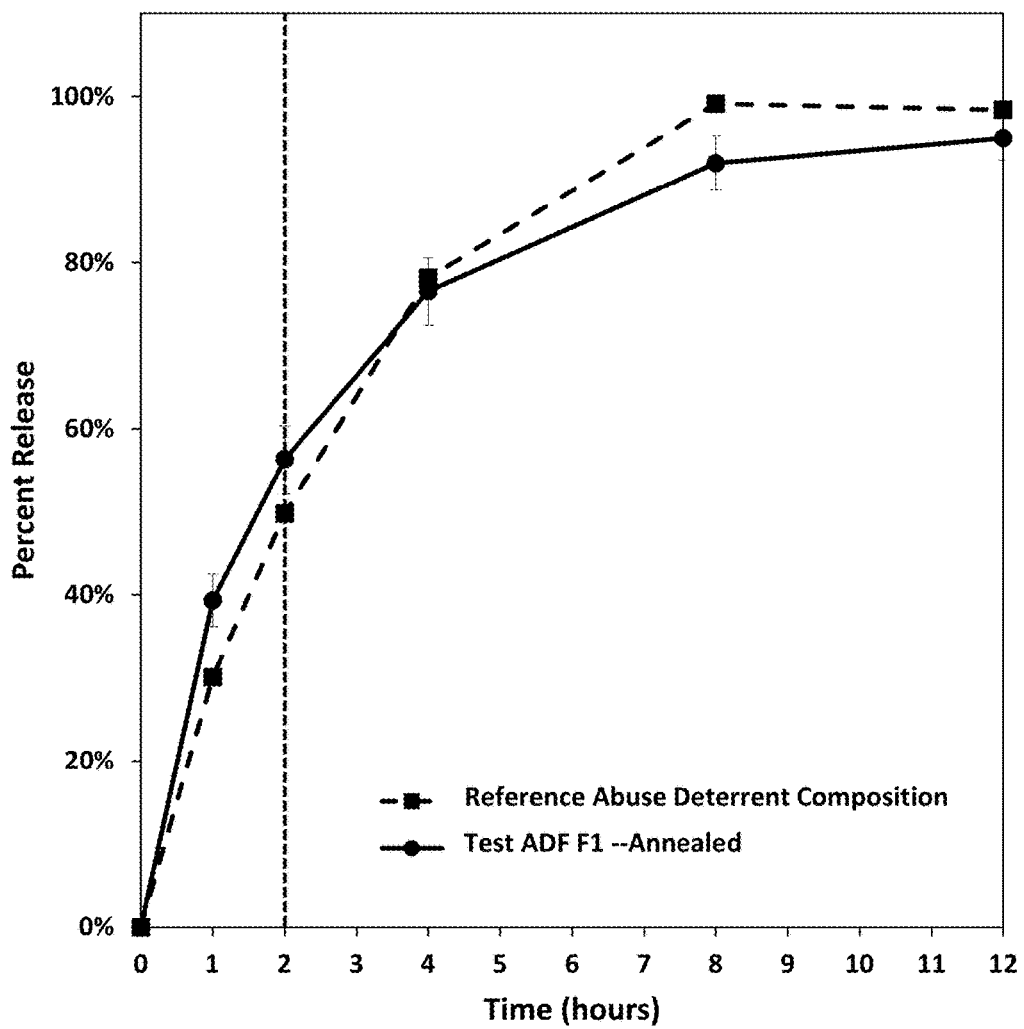
FIG. 1. Percent release of oxycodone from an annealed test abuse deterrent pharmaceutical composition (F1) compared to the percent release of oxycodone from a reference abuse deterrent pharmaceutical composition in fasted state simulated gastric fluid FaSSGF and fasted state simulated intestinal fluid FaSSIF buffer.

Described herein are abuse deterrent controlled release pharmaceutical compositions. The pharmaceutical compositions described herein provide abuse deterrent matrices and methods for preparation thereof. Also described herein are compositions and methods for manufacturing soft or hard capsules comprising abuse deterrent controlled release pharmaceutical matrices. In some embodiments described herein, the capsule is a soft capsule. In some embodiments described herein, the soft capsule is a hard capsule. In some embodiments described herein, the soft capsule is an enteric soft capsule. In some embodiments described herein, the soft capsule is an enteric hard capsule.

The term "abuse deterrent," or "tamper resistant" as used herein, refers to a pharmaceutical composition that is resistant to tampering or accessing the active pharmaceutical ingredient for recreational drug use or drug abuse.

The phrase "recreational drug use," as used herein, refers to the voluntary use of an active pharmaceutical agent or drug for a non-medical purpose to induce an effect, such as pleasure, satisfaction, euphoria, dissociation, or to enhance an experience.

The term "drug abuse," as use herein, refers to the habitual, compulsive, or recurrent use of an active pharmaceutical agent or drug, often despite negative consequences.

The term "tampering," as used herein, refers to any kind of actual or attempted physical manipulation or interference that may result in particle size reduction of a pharmaceutical composition. Tampering, as used herein also includes any actual or attempted dissolution or extraction of active pharmaceutical ingredients using solvents. Compositions that are resistant to physical tampering are formulated in such a way that the composition cannot readily reduced to a form that is suitable for abuse, such as, for example, injection or snorting, because the tablet cannot easily be ground, grated, dissolved, extracted, and the like at any temperature. Examples of physical tampering include, but are not limited to, crushing, grinding, grating, cutting, crisping, and other methods of particle size reduction. Dissolution tampering includes actual or attempted actions to dissolve or extract active pharmaceutical ingredients using aqueous or organic solvents such as water, ethanol, isopropanol, ethyl acetate, acetone, ether, or the like, at any temperature including boiling. Tampering, as used herein, includes "dose dumping."

The term "dose dumping" or "dumping" as used herein refers to the rapid release of the entire amount or a significant fraction of an active pharmaceutical ingredient or drug. Drug abusers often intentionally pursue dumping of a drug from the dosage form.

The terms "drug", "active ingredient," "active pharmaceutical ingredient," or "active pharmaceutical agent" as used herein refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The term "anti-OIC agent" as used herein refers specifically to any agent, active ingredient, compound, substance, composition, or mixture thereof, which reduces opioid induced constipation (OIC) or one or more symptoms thereof.

The terms "dosage" or "dose" denote any form of the active ingredient formulation that contains an amount sufficient to produce a therapeutic effect with a single administration. The dosage form used herein is for oral administration. The oral dosage forms are soft capsules, enteric soft capsules, hard capsules, or enteric hard capsules.

The term "annealed" as used herein refers to a pharmaceutical composition that has been heated to an elevated temperature (e.g., 60° C. to 80° C.) for a time period (e.g., from 10 min to 120 min) and then slowly cooled at a specific rate (e.g., 2° C. per 10 min) to form an annealed dosage form. In some aspects, pharmaceutical compositions comprising a capsule shell encapsulating a fill composition as described herein may be annealed at a temperature from about 50° C. to about 90° C. for about 0.1 hours to about 5 hours, including all integers within the specified ranges of temperature and time. In some aspects described herein, pharmaceutical compositions comprising a soft or hard capsule shell encapsulating a matrix fill as described herein may be annealed at a temperature of about 70° C. from about 20 min to about 90 min, including all integers within the specified range. In some aspects described herein, pharmaceutical compositions comprising a soft or hard capsule shell encapsulating a matrix fill as described herein may be annealed at a temperature of about 70° C. for about 1 hour. In some aspects, after annealing, the dosage form is slowly cooled to room temperature at a cooling rate of about 2° C. to about 10° C. per about 5 min to about 20 min (e.g., 2-10° C./5-20 min). In some aspects described herein, a capsule is coated prior to the annealing step.

The term "non-annealed" refers to a pharmaceutical composition comprising a soft or hard capsule shell encapsulating a matrix fill described herein that has not been heated following encapsulation.

The terms "active pharmaceutical ingredient load" or "drug load" as used herein refers to the quantity (mass) of the active pharmaceutical ingredient comprised in a single soft or hard capsule fill.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The term "controlled release" as used herein encompasses the terms "immediate release," "modified release," "sustained release," "extended release," and "delayed release."

The terms "extended release" or "sustained release" as used herein refers to a composition that releases an active ingredient according to a desired profile over an extended period under physiological conditions or in an in vitro test. By "extended period" it is meant a continuous period of time of at least about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of about 18 hours under physiological conditions or in an in vitro assay.

The term "modified release" as used herein refers to a composition that releases an active ingredient at a slower rate than does an immediate release formulation under physiological conditions or in an in vitro test.

The term "delayed" release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under physiological conditions or in an in vitro test.

As used herein, the phrase "abuse deterrent controlled release" refers to a pharmaceutical composition comprising components or a formulation that prevents liberation of the active pharmaceutical ingredient(s) from the composition for potential abuse or dose dumping and the composition provides controlled release delivery of the active pharmaceutical ingredient upon ingestion of the composition by a subject.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{last}$" as used herein refers to the area under the blood (plasma, serum, or whole blood) concentration versus time curve at the last measurable concentration of the analyte, and is expressed in units of h·mg/L (or h·ng/mL) for at least one or more doses of the pharmaceutical compositions described herein.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The phrase "room temperature" as used herein refers to about 25° C. at standard atmospheric pressure.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing," "has," or "having," and the like, mean "comprising."

The term "or" can be conjunctive or disjunctive.

Described herein are pharmaceutical compositions comprising abuse deterrent controlled release matrices comprising active pharmaceutical ingredients. The matrix is structured to prevent extraction of the active pharmaceutical ingredients.

One embodiment described herein is an oral abuse deterrent controlled release pharmaceutical composition that releases one or more active pharmaceutical ingredients over a period of about 12 hours.

In some embodiments, the pharmaceutical composition described herein comprises a soft or hard capsule comprising an abuse deterrent controlled release matrix comprising an active pharmaceutical ingredient. In one embodiment, the active pharmaceutical ingredient is an analgesic. In another embodiment, the active pharmaceutical ingredient is an opioid agonist. In another embodiment, the active pharmaceutical ingredient is an opioid analgesic.

In another embodiment, the soft or hard capsule comprising a matrix can provide controlled release properties. Such controlled release matrix fills are described in International Patent Application Publication No. WO 2005/009409 and WO 2006/096580, U.S. Patent Application Publication Nos. US 2006/0115527 and US 2007/0053868, and U.S. Pat. Nos. 8,293,270 and 8,333,989, each of which are incorporated by reference herein for such teachings. In one aspect, the soft or hard capsule and matrix can be configured to provide controlled release, extended release, sustained release, delayed release, or combinations thereof.

In other embodiments, the pharmaceutical composition described herein comprises abuse deterrent properties. These abuse deterrent properties reduce the likelihood that the active pharmaceutical ingredient can be extracted from the composition through mechanisms, including but not limited to crushing, grating, grinding, or cutting of the capsule to expose the matrix thereby facilitating solvation or extraction of the active pharmaceutical ingredient. Exemplary and non-limiting abuse deterrent matrices useful in the pharmaceutical composition described herein may be those found in International Application No. PCT/US2015/024464; U.S. patent application Ser. No. 14/679,233; PCT International Application No. PCT/US2015/054443; U.S. patent application Ser. No. 14/877,208, each of which is incorporated by reference herein in their entirety. In addition, the abuse deterrent properties reduce the likelihood that the active pharmaceutical ingredient can be extracted from the composition by dissolving or extracting in ethanol solutions, dissolving in solutions having pH values from about 1 to about 12, or dissolving in household chemical compositions, including water, coffee, vinegar, cola, milk, ethanol, isopropanol, acetone, ethyl acetate, or other common solvents. In addition, the abuse deterrent properties further reduce the likelihood that the active pharmaceutical ingredient can be extracted by boiling in water or ethanol solutions.

In other embodiments described herein, the matrix comprises a lipid or lipophilic vehicle that provides a suspension or a solution of the active pharmaceutical ingredient. In one aspect, a soft or hard capsule comprising an active pharmaceutical ingredient provides controlled release of the active pharmaceutical ingredient.

In other embodiments described herein, the pharmaceutical composition provides matrix fills for the active pharmaceutical ingredient, or derivatives thereof, based on lipids or lipophilic materials. The matrices described herein have a hydrophobic (lipophilic) surface in contact with a hydrophilic soft capsule shell to minimize any potential shell-fill interactions, such as when soft capsules are filled with hydrophilic materials. In one embodiment described herein are methods for manufacturing matrix fills comprising an abuse deterrent controlled release matrix comprising an active pharmaceutical ingredient in a soft capsule in the form of a suspension, where part or all of the active pharmaceutical ingredient is suspended within the matrix. In one embodiment described herein is a soft capsule having a shell and an abuse deterrent controlled release matrix fill, wherein the matrix includes an active pharmaceutical ingredient suspended as particles within the matrix.

In one embodiment described herein, an exemplary abuse deterrent controlled release matrix has the composition of Table 1, including all possible iterations of the specified ranges that provide 100% for the total weight percentage, including or excluding optional excipients.

TABLE 1

Exemplary Abuse Deterrent Controlled Release Matrix Composition

| Component | Exemplary Components | Composition Range (%) |
|---|---|---|
| Flowability Enhancer | Mono-, di-, tri-glycerides, glyceryl monocaprylate; oleic acid; glyceryl monolinoleate (e.g., Maisine ™ 35-1) | 35-70 |
| Release Modifier | Polyethylene oxide (PEO) (e.g., POLYOX ™) | 20-50 |
| Release Modifier 2 | Carboxyvinyl polymers (e.g., Carbopol ® polymers) | 0-10 |
| Viscosity Modifier | Polyvinylpyrrolidone; ethylcellulose | 0-10 |
| Antioxidant | BHT, BHA | 0-0.5 |
| Active pharmaceutical ingredient(s) | Oxycodone, hydrocodone, tapentadol | 0.1-50 |

In one embodiment, the matrix may comprise one or more flowability enhancers. In one aspect, suitable flowability enhancers have surfactant like properties. Exemplary and non-limiting flowability enhancers may comprise partial triglyceride medium chain, monoglycerides, diglycerides and triglycerides, polyethylene glycol (molecular weight of about 200 or greater), medium chain triglycerides of caprylic/capric acid, glyceryl monooleate, glyceryl monostearate, glyceryl monolinoleate (e.g., Maisine™ 35-1), polyglyceryl-3-dioleate, oleoyl macrogol-6 glycerides, linoleoyl macrogol-6 glycerides. In one aspect, the flowability enhancer comprises a medium chain mono- and di-glycerides (e.g., glyceryl monocaprylate or Capmul® MCM) In one aspect, the flowability enhancer comprises oleic acid. In another aspect, the flowability enhancer comprises oleic acid. In another aspect, the flowability enhancer comprises glyceryl monolinoleate (e.g., Maisine™ 35-1).

In another embodiment, the matrix may comprise one or more surfactants as described herein. In one aspect, the flowability enhancer comprises a non-ionic surfactant, an anionic surfactant, a zwitterionic surfactant, or a cationic surfactant or a combination thereof. In another aspect, the flowability enhancer comprises a non-ionic surfactant. Exemplary and non-limiting surfactants that may be useful in the abuse deterrent matrices described herein comprise Suitable surfactants include: Pluronic® 10R5, Pluronic® 17R2, Pluronic® 17R4, Pluronic® 25R2, Pluronic® 25R4, Pluronic® 31R1, Pluronic® F 108, Pluronic® F 108 NF, Pluronic® F 108, Pluronic® F 108NF, Poloxamer 338, Pluronic® F 127, Pluronic® F 127 NF, Pluronic® F 127 NF 500 BHT Prill, Pluronic® F 127 NF Prill, Poloxamer 407, Pluronic® F 38, Pluronic® F 38 Pastille, Pluronic® F 68, Pluronic® F 68 LF Pastille, Pluronic® F 68 NF, Pluronic® F 68 NF Prill, Poloxamer 188, Pluronic® F 68 Pastille, Pluronic® F 77, Pluronic® F 77 Micropastille, Pluronic® F 87, Pluronic® F 87 NF, Pluronic® F 87 NF Prill, Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® O10, Brij® O10, BRIJ® O20, Brij® S10, Brij®

S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, sodium lauryl sulfate, 2,4,7,9-tetramethyl-5-decyne-4,7-diol ethoxylate, Nonidet™ P-40, Triton™ N-101, Span® 80, Triton™ X-100, Triton™ X-114, Triton™ X-405, TWEEN® 20, TWEEN® 40, TWEEN® 60, TWEEN® 85, Zonyl® FS-300, or Zonyl® FSN.

Additional exemplary and non-limiting flowability enhancers may include higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

In another embodiment, the flowability enhancer has a hydrophilic lipophilic balance (HLB) ranging from about 0 to about 20. In one aspect, the flowability enhancer has an HLB value of less than 10. In another aspect, the flowability enhancer has an HLB value of between 1 and 6. In another aspect, the flowability enhancer has an HLB value of less than 5. The HLB characteristic of surfactants and other compounds can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993).

In another embodiment, the matrix may further include a lipid or lipophilic vehicles, such as olive oil, soybean oil, sunflower oil, canola oil, palmitoleic acid, oleic acid, myristoleic acid, linoleic acid, arachidonic acid, vegetable oil, corn oil, sun flower oil, coconut oil, cocoa oil, peanut oil, almond oil, cottonseed oil, persic oil, sesame oil, squalane oil, castor oil, fish oil, paraffin oil, or mineral oil.

In another embodiment, the matrix may comprise one or more release modifiers. In one aspect, the release modifier comprises a high molecular weight polyethylene oxide or a carboxyvinyl polymer, or a combination thereof. As described herein, high molecular weight polyethylene oxide polymers have an approximate molecular weight based on viscosity or rheology ($M_v$) of at least about 600,000 to about 10,000,000 or greater. In one aspect, the release modifier may comprise a high molecular weight polyethylene oxide having a molecular weight ($M_v$) of about 600,000 to about 10,000,000, including each integer within the specified range. In another aspect, the release modifier may comprise a high molecular weight polyethylene oxide having a molecular weight ($M_v$) of about 5,000,000 to about 10,000,000, including each integer within the specified range. In another aspect, the release modifier may comprise a high molecular weight polyethylene oxide having a molecular weight ($M_v$) of about 4,000,000 to about 7,000,000, including each integer within the specified range. In another aspect, the release modifier may comprise a high molecular weight polyethylene oxide having a molecular weight (MO of about 600,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000 or about 10,000,000. In another aspect, the release modifier may comprise a high molecular weight polyethylene oxide having a molecular weight ($M_v$) of about 4,000,000. In another aspect, the release modifier may comprise a high molecular weight polyethylene oxide having a molecular weight ($M_v$) of about 5,000,000. In another aspect, the release modifier may comprise a high molecular weight polyethylene oxide having a molecular weight ($M_v$) of about 7,000,000.

The molecular weight measurements of polyethylene oxide may be approximated using rheological measurements using a viscometer. For example, polyethylene oxide is considered to have an approximate molecular weight ($M_v$) of 600,000 when a 5% (by wt) aqueous solution of polyethylene oxide using a Brookfield viscometer Model RVF, spindle No. 2, at 2 rpm, at 25° C. shows a viscosity range of 30 to 50 mPa s (cP). Polyethylene oxide is considered to have an approximate molecular weight ($M_v$) of 1,000,000 when a 2% (by wt) aqueous solution of polyethylene oxide using a Brookfield viscometer Model RVF, spindle No. 1, at 10 rpm, at 25° C. shows a viscosity range of 400 to 800 mPa s (cP). Polyethylene oxide is considered to have an approximate molecular weight ($M_v$) of 2,000,000 when a 2% (by wt) aqueous solution of polyethylene oxide using a Brookfield viscometer Model RVF, spindle No. 3, at 10 rpm, at 25° C. shows a viscosity range of 2000 to 4000 mPa s (cP). Polyethylene oxide is considered to have an approximate molecular weight ($M_v$) of 4,000,000 when a 1% (by wt) aqueous solution of polyethylene oxide using a Brookfield viscometer Model RVF, spindle No. 2, at 2 rpm, at 25° C. shows a viscosity range of 1650 to 5500 mPa s (cP). Polyethylene oxide is considered to have an approximate molecular weight ($M_v$) of 5,000,000 when a 1% (by wt) aqueous solution of polyethylene oxide using a Brookfield viscometer Model RVF, spindle No. 2, at 2 rpm, at 25° C. shows a viscosity range of 5500 to 7500 mPa s (cP). Polyethylene oxide is considered to have an approximate molecular weight ($M_v$) of 7,000,000 when a 1% (by wt) aqueous solution of polyethylene oxide using a Brookfield viscometer Model RVF, spindle No. 2, at 2 rpm, at 25° C. shows a viscosity range of 7500 to 10,000 mPa s (cP). Polyethylene oxide is considered to have an approximate molecular weight ($M_v$) of 8,000,000 when a 1% (by wt) aqueous solution of polyethylene oxide using a Brookfield viscometer Model RVF, spindle No. 2, at 2 rpm, at 25° C. shows a viscosity range of 10,000 to 15,000 mPa s (cP). Suitable polyethylene oxide polymers with the above described viscosity and molecular weight values that are useful for the matrices described are, for example, POLYOX™ polymers, such as WSR-205, WSR-1105, WSR N-12K, WSR N-60K, WSR-301, WSR Coagulant, WSR-303, WSR 308, UCARFLOC Polymers 300, 302, 304, and 309 commercially available from Dow Chemical Company. In one aspect, the polyethylene oxide polymer is POLYOX™ WSR-301 ($M_v \approx 4,000,000$) or POLYOX™ WSR-303 ($M_v \approx 7,000,000$) (Dow Chemical Co.). In one aspect, the polyethylene oxide polymer is POLYOX™ WSR-301 ($M_v \approx 4,000,000$).

In another embodiment, the composition comprises one or more viscosity modifiers. Suitable and non-limiting viscosity modifiers that may be present in the matrices described herein comprise methylcellulose, ethylcellulose, hydroxypropylmethyl cellulose, hydroxypropyl cellulose, hydroxyethyl cellulose, hydroxymethyl cellulose, polymethylmethacrylate, polyhydroxyethylmethacrylate, polyvinylpyrrolidone, copovidone, polyvinyl alcohol, a copolymer of polyvinylpyrrolidone and polyvinyl acetate, or combinations thereof. For example, polymers commercially available as Methocel™ K100M, Methocel™ A4M, Ethocel™ Premium LV CR, K4M Premium CR, K15M Premium CR, K100 Premium CR, E4M Premium CR, E10M Premium CR, or E4M Premium (Dow Chemical Co.), CELLOSIZE™, or WALOCEL™ CRT may be used in the abuse deterrent matrices described herein. These viscosity modifiers may comprise a viscosity of about 50 cP to about 100,000 cP, including each integer within the specified range. For example, these additional release modifiers may comprise a viscosity of about 50 cP, about 100 cP, about 200 cP, about 300 cP, about 400 cP, about 500 cP, about 750 cP, about 1,000 cP, about 1,500 cP, about 2,000 cP, about 2,500 cP, about 3,000 cP, about 3,500 cP, about 4,000 cP, about 4,500 cP, about 5,000 cP, about 6,000 cP, about 7,000 cP, about 8,000 cP, about 9,000 cP, or about 10,000 cP, about 15,000 cP, about 20,000 cP, about 30,000 cP, about 40,000 cP, about 50,000 cP, about 60,000 cP, about 70,000 cP, about 80,000 cP, about 90,000 cP, about 100,000 cP, greater than 100,000 cP, or even greater. In one embodiment, the matrix comprises hydroxylpropyl methylcellulose (e.g., Methocel™ K100M). In another embodiment, the matrix comprises ethylcellulose (e.g., Ethocel™ 20cP). In another embodiment, the matrix comprises a polyvinylpyrrolidone (e.g., polyvinylpyrrolidone K90).

In another embodiment, the abuse-deterrent matrix may optionally comprise one or more antioxidants. Suitable antioxidants comprise tocopherols (e.g., alpha-tocopherol, beta-tocopherol, gamma-tocopherol, or delta-tocopherol), butylated hydroxytoluene (BHT), butylated hydroxyanisole (BHA), citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or combinations thereof.

In one embodiment described herein, the abuse deterrent matrix may comprise one or more flowability enhancers, one or more release modifiers, one or more active pharmaceutical ingredients, optionally one or more antioxidants, optionally one or more viscosity modifiers, optionally one or more hydrophilic vehicles, and optionally one or more other pharmaceutically acceptable excipients in a weight percentage amount of the matrix fill mass as further described herein.

In another embodiment, the one or more flowability enhancers comprises from about 40% to about 80% of the matrix fill mass, including all integers within the specified range. In one aspect, the one or more flowability enhancers comprises from about 50% to about 80% of the matrix fill mass, including all integers within the specified range. In another aspect, the one or more flowability enhancers comprises from about 50% to about 60% of the matrix fill mass, including all integers within the specified range. In another aspect, the one or more flowability enhancers comprises from about 50% to about 60% of the matrix fill mass, including all integers within the specified range. In another aspect, the one or more flowability enhancers comprises from about 40%, about 45%, about 50%, about 55%, about 60%, about 65%, about 70%, about 75%, or about 80% of the matrix fill mass.

In another embodiment, the one or more release modifiers comprises from about 20% to about 50% of the matrix fill mass, including all integers within the specified range. In one aspect, the one or more release modifiers comprises from about 25% to about 50% of the matrix fill mass, including all integers within the specified range. In another aspect, the one or more release modifiers comprises from about 25% to about 40% of the matrix fill mass, including all integers within the specified range. In another aspect, the one or more release modifiers comprises from about 25% to about 35% of the matrix fill mass, including all integers within the specified range. In another aspect, the one or more release modifiers comprises about 20%, about 25%, about 30%, about 35%, about 40%, about 45%, or about 50% of the matrix fill mass.

In another embodiment, the one or more viscosity modifiers may comprise from about 0.5% to about 8% of the matrix fill mass, including all integers within the specified range. In one aspect, the one or more viscosity modifiers may comprise from about 0.5% to about 5% of the matrix fill mass, including all integers within the specified range. In another aspect, the one or more viscosity modifiers may comprise from about 0.5% to about 3% of the matrix fill mass, including all integers within the specified range. In another aspect, the one or more viscosity modifiers may comprise from about 0.5% to about 2% of the matrix fill mass, including all integers within the specified range. In another aspect, the one or more viscosity modifiers may comprise about 0.5%, about 0.75%, about 1%, about 2%, about 3%, about 4%, about 5%, about 6%, about 7%, or about 8%, of the matrix fill mass. In another aspect, matrix fill mass may not have any viscosity modifier.

In another embodiment, one or more antioxidants may comprise from about 0.1% to about 0.5% of the matrix mass, including all integers within the specified range. In one aspect, the one or more antioxidants may comprise about 0.3%, 0.4%, or 0.5% of the matrix fill mass.

In another embodiment, the one or more hydrophilic polymers comprises from about 1% to about 50% by weight of the matrix fill mass, including all integers within the specified range. In one aspect, the one or more hydrophilic polymer s comprises from about 1% to about 30% of the matrix fill mass, including all integers within the specified range. In another aspect, the one or more hydrophilic polymers comprises from about 25% to about 40% of the matrix fill mass, including all integers within the specified range. In another aspect, the one or more hydrophilic polymers comprises from about 25% to about 35% of the matrix fill mass, including all integers within the specified range. In one aspect, the one or more hydrophilic polymer s comprises from about 1% to about 10% of the matrix fill mass, including all integers within the specified range. In another aspect, the one or more hydrophilic polymers comprises about 1%, about 5%, about 10% about, 20%, about 25%, about 30%, about 35%, about 40%, about 45%, or about 50% of the matrix fill mass.

In another embodiment, the one or more active pharmaceutical ingredient comprises from about 0.1% to about 50% of the matrix fill mass, including all integers within the specified range. In another embodiment, the one or more active pharmaceutical ingredient comprises from about 1% to about 50% of the matrix fill mass, including all integers within the specified range. In another embodiment, the one or more active pharmaceutical ingredient comprises from about 1% to about 25% of the matrix fill mass, including all integers within the specified range. In one aspect, the active pharmaceutical ingredient comprises about 5% of the matrix fill mass. In one aspect, the active pharmaceutical ingredient comprises about 7% of the matrix fill mass. In one aspect, the active pharmaceutical ingredient comprises about 10% of the matrix fill mass. In one aspect, the active pharmaceutical ingredient comprises about 20% of the matrix fill mass. In one aspect, the active pharmaceutical ingredient comprises about 25% of the matrix fill mass.

In another embodiment, the weight percentage ratio of release modifier to flowability enhancer ranges from about 0.2:1 to about 1:1.5, including all iterations of ratios within the specified range. In one aspect, the weight percentage ratio of release modifier to flowability enhancer ranges from about 0.2:1 to about 0.75:1, including all iterations of ratios within the specified range. In one aspect, the weight percentage ratio of release modifier to flowability enhancer ranges from about 0.2:1 to about 0.5:1, including all iterations of ratios within the specified range. In one aspect, the weight percentage ratio of release modifier to flowability enhancer ranges from about 0.2:1, about 0.3:1, about 0.4:1, about 0.5:1, about 0.6:1, about 0.7:1, about 0.9:1, about 1:1, about 1.1:1, or about 1.2:1.

In another embodiment, the weight percentage ratio of active pharmaceutical ingredient to the total matrix fill mass ranges from about 1:1000 to about 1:3, including all iterations of ratios within the specified range. In another embodiment, the weight percentage ratio of active pharmaceutical ingredient to the total matrix fill mass ranges from about 1:100 to about 1:2, including all iterations of ratios within the specified range. In another embodiment, the weight percentage ratio of active pharmaceutical ingredient to the total matrix fill mass ranges from about 1:15 to about 1:2, including all iterations of ratios within the specified range. In one aspect, the weight percentage ratio of active pharmaceutical ingredient to the total matrix fill mass is about 1:100. In another aspect, the weight percentage ratio of active pharmaceutical ingredient to the total matrix is about 1:10. In another aspect, the weight percentage ratio of active pharmaceutical ingredient to the total matrix fill mass is about 1:7.5. In another aspect, the weight percentage ratio of active pharmaceutical ingredient to the total matrix fill mass is about 1:5. In another aspect, the weight percentage ratio of active pharmaceutical ingredient to the total matrix fill mass is about 1:3. In another aspect, the weight percentage ratio of active pharmaceutical ingredient to the total matrix fill mass is about 1:2.

In one embodiment described herein, the abuse deterrent matrix may comprise one or more flowability enhancers, one or more release modifiers, one or more active pharmaceutical ingredients, optionally one or more viscosity modifiers, wherein the matrix comprises any one of the compositions of Tables 7 and 9-10.

It was found that the addition of one or more flowability enhancers such as mono- or di-glycerides (e.g., Capmul® MCM), oleic acid, and glyceryl monolinoleate (e.g., Maisine™ 35-1) increases the flowability of the one or more release modifiers (e.g., high molecular weight polyethylene oxide), and thus, provides for a flowable matrix suitable for encapsulation in the soft or hard capsule shells as described herein. For example, using a conventional hydrophilic vehicle, such as polyethylene glycol, it was demonstrated that a carrier comprising polyethylene glycol had a high degree of miscibility with the high molecular weight polyethylene oxide. The resulting mixtures of polyethylene oxide and polyethylene glycol became highly viscous at room temperature, which complicates further processing steps. Further, it was found that certain oils and lipophilic vehicles are not suitable as a flowability enhancer for the one or more release modifiers.

Thus, without being bound by any theory, it is believed that the flowable characteristics of the matrices described herein may be due to the limited miscibility of the one or more release modifiers and the one or more flowability enhancers described herein at room temperature. For example, it was found that mono- or di-glycerides (e.g., Capmul® MCM), oleic acid, or glyceryl monolinoleate (e.g., Maisine™ 35-1) allows adequate matrix flowability at room temperature due to solubilization of high molecular weight polyethylene oxide that allows standard encapsulation techniques to be employed. It was further found that matrix compositions comprising a flowability enhancer with surfactant-like properties, such as for example, mono- or di-glycerides (e.g., Capmul® MCM), oleic acid, or glyceryl monolinoleate (e.g., Maisine™ 35-1) and a high molecular weight polyethylene oxide had a fluid-like consistency at room temperature.

It was further demonstrated that the flowability enhancer and polyethylene oxide became more miscible after being heated to about 70° C. Surprisingly, it was discovered that these matrices having the flowability enhancers, such as mono- or di-glycerides (e.g., Capmul® MCM), oleic acid, or glyceryl monolinoleate (e.g., Maisine™ 35-1) when heated to an elevated temperature of about 70° C. and then cooled to room temperature, became an elastic, rubbery, semi-solid material having an increased Young's modulus. In contrast, it was also unexpectedly demonstrated that this solidifying effect did not occur for compositions having soybean oil as a flowability enhancer. Furthermore, it was surprisingly and advantageously found that the process of heating and cooling the matrices comprising polyethylene oxide and a suitable flow ability enhancer further allow for reduced levels of polyethylene oxide to be used, while exhibiting effective abuse deterrent and controlled release properties, which has previously been unrealized.

Without being bound by any theory, it is thought that the release modifier is suspended in the flowability enhancer throughout the processing steps. During the annealing steps, the release modifier is believed to become molten. The two components, therefore, become miscible at this point. This appears to be a synergistic effect wherein the flowability enhancer reduces the melting point of the release modifier and also solubilizes the release modifier at the elevated annealing temperature (which is lower than the typical melting point of the release modifier by about 20-50° C.). When cooled, the release modifier and flowability enhancer recrystallizes and forms an elastic semi-solid composition enveloping the active pharmaceutical ingredient. For example, high molecular weight polyethylene oxide is a semi-crystalline polymer known to melt at about 100° C. In the presence of a suitable flowability enhancer, such as mono- or di-glycerides (e.g., Capmul® MCM), oleic acid, or glyceryl monolinoleate (e.g., Maisine™ 35-1), polyethylene oxide becomes solubilized at about 50 to 80° C. After subsequent cooling, the polyethylene oxide and flowability enhancer mixture solidify to form an elastic, rubbery, semi-solid composition. Thus, the composition and annealing process described herein unexpectedly resulted in the formation of an elastic semi-solid composition with advantageous abuse deterrent properties.

As described herein, the heated pharmaceutical compositions comprising the abuse deterrent matrix fills are in some embodiments annealed by heating the compositions.

In some embodiments, the pharmaceutical compositions comprising a soft or hard capsule shell encapsulating a matrix fill as described herein may be annealed at a temperature of about 70° C. for about 1 hour or less. These annealed elastic semi-solid matrices comprise advantageous abuse deterrent characteristics.

A common method for extracting abuse prone drugs is by boiling the composition. It was found that the abuse deterrent matrix fills described herein further provide for abuse deterrence by reducing the percentage of released active pharmaceutical ingredient released during boiling, suggesting that the matrices described herein maintain a semi-solid elastic material at high temperatures (e.g., in excess of 90-100° C.). Without wishing to be bound by any theory, it is thought that the lipophilic and solubilizing nature of the flowability enhancer in combination with high molecular weight polyethylene oxide provide abuse deterrent characteristics following an annealing step. The semi-solid elastic characteristics of the abuse deterrent matrix fills described herein further prevent or reduce the likelihood for the extraction of active pharmaceutical ingredients through the additional means of crushing, grating, grinding, or cutting the dosage forms further described herein.

Another common method for extracting abuse prone drugs is through ethanol based extraction of the composition. It was found that the abuse deterrent matrices described herein further reduce the extraction of one or more active pharmaceutical ingredients in high percentage Ethanol solutions (e.g., 80%), while maintaining desired release rates in gastric-like environments. Thus, the presence of the components of the abuse deterrent matrix compositions described herein function to inhibit drug release from the pharmaceutical compositions described herein using common attempts of drug extraction. Thus, the matrix compositions described herein have abuse deterrent properties by preventing the liberation of the active ingredient for injection or insufflation and prevent solvation, dissolution, or extraction of the active pharmaceutical ingredient by use of aqueous or organic solutions. Furthermore, the matrix compositions also provide controlled release delivery of the active pharmaceutical ingredient after ingestion by a subject.

In one embodiment, the matrix contains an active pharmaceutical ingredient in a suspended form, soluble form, insoluble form, or combinations thereof. The active pharmaceutical ingredient can be dispersed in the internal phase as a suspension form. A suspension as used herein means the API does not dissolve in one of the phases and remains as a solid.

In another embodiment, the matrix contains an active pharmaceutical ingredient useful for the treatment of pain. In one embodiment, the API comprises one or more opioid receptor agonists. In one embodiment, the active pharmaceutical ingredient includes one or more of oxycodone, hydrocodone, oxymorphone, hydromorphone, morphine, codeine, methadone, fentanyl, tapentadol, tramadol, meperidine, propoxyphene, flunitrazepam, barbiturates, amytal, nembutal, seconal, phenobarbital; benzodiazepines, zolpidem, zaleplon, eszopiclone, amphetamines, methylphenidate, salts thereof, or a combination thereof.

In another embodiment, the matrix comprises one or more active pharmaceutical ingredients (API). In one aspect, the active pharmaceutical ingredient is useful in treating pain. In one aspect, the active pharmaceutical ingredient is oxycodone, hydrocodone, oxymorphone, hydromorphone, tapentadol, morphine, or codeine. In one aspect, the active pharmaceutical ingredient is oxycodone or hydrocodone. In one aspect, the active pharmaceutical ingredient is oxycodone.

Examples of specific active drug substances suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine, or bucillamine.

In another embodiment, suitable active pharmaceutical ingredients can comprise analgesics, such as, for example: opioids, natural opium alkaloids, morphine, opium, hydromorphone, nicomorphine, oxycodone, dihydrocodone, diamorphine, tapentadol, papaveretum, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, difluni sal, potassium salicylate, guaceti sal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

In another embodiment, suitable active pharmaceutical ingredients can comprise anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

In another embodiment, suitable active pharmaceutical ingredients can comprise antimigraine active drug substances, such as, for example: ergot alkaloids, dihydroergotamine, ergotamine, methysergide, lisuride, corticosteroid derivatives, flumedroxone, selective serotonin ($5HT^1$) agonists, sumatriptan, naratriptan, zolmitriptan, rizatriptan, almotriptan, eletriptan, frovatriptan, other antimigraine preparations, pizotifen, clonidine, iprazochrome, dimetotiazine, or oxetorone.

In another embodiment, suitable active pharmaceutical ingredients can comprise antiepileptic active drug substances, such as, for example: barbiturates and derivatives, methylphenobarbital, phenobarbital, primidone, barbexaclone, metharbital, hydantoin derivatives, ethotoin, phenytoin, amino(diphenylhydantoin) valeric acid, mephenytoin, fosphenytoin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, or beclamide.

In another embodiment, suitable active pharmaceutical ingredients can comprise anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, or etybenzatropine.

In another embodiment, suitable active pharmaceutical ingredients can comprise dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine, oxidase B inhibitors, selegiline, rasagiline, other dopaminergic agents, such as, for example: tolcapone, entacapone, or budipine.

In another embodiment, suitable active pharmaceutical ingredients can comprise antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopenthixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, or paliperidone.

In another embodiment, suitable active pharmaceutical ingredients can comprise anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclooctadiene derivatives, benzoctamine, azaspirodecanedione derivatives, buspirone, other anxiolytics, such as, for example: mephenoxalone, gedocarnil, or etifoxine.

In another embodiment, suitable active pharmaceutical ingredients can comprise hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, ethallobarbital, allobarbital, proxibarbal, aldehydes and derivatives, chloral hydrate, chloralodol, acetylglycinamide chloral hydrate, dichloralphenazone, paraldehyde, benzodiazepine emepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, or dipiperonylaminoethanol.

In another embodiment, suitable active pharmaceutical ingredients can comprise antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, amineptine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lis dexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, or vinpocetine.

In another embodiment, suitable active pharmaceutical ingredients can comprise anti-dementia active drug substances, such as, for example: anticholinesterases, tacrine, donepezil, rivastigmine, galantamine, other anti-dementia drugs, memantine, or *ginkgo biloba*.

In another embodiment, suitable active pharmaceutical ingredients can comprise other nervous system active drug substances, such as, for example: parasympathomimetics, anticholinesterases, neostigmine, pyridostigmine, distigmine, ambenonium, choline esters, carbachol, bethanechol, and other parasympathomimetics, such as, for example, pilocarpine, or choline alfoscerate.

Active drug substances used in addictive disorders, such as, for example: nicotine, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, dexhydroxybutyric acid, or amifampridine.

In another embodiment, suitable active pharmaceutical ingredients can comprise opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodone, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, or dimethoxanate.

In another embodiment, the active pharmaceutical ingredient may be a substance with abuse potential that presents a safety risk. Such active drug substance may include: 1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine, 1-phenylcyclohexylamine, 1-piperidinocyclohexanecarbonitrile, 2,5-dimethoxy-4-ethylamphetamine, 2,5-dimethoxyamphetamine, 2C-B-(4-bromo-2,5-dimethoxyphenethylamine), 2C-D (2,5-dimethoxy-4-methylphenethylamine), 2C-I (4-iodo-2,5-dimethoxyphenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiophenethylamine), 3,4-methylenedioxymethamphetamine, 3,4,5-trimethoxyamphetamine, 3,4-methylenedioxy amphetamine, 3,4-methylenedioxy-N-ethyl amphetamine, 3-methylfentanyl, 3-methylthiofentanyl, 4-bromo-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-diisopropyltryptamine), 5-MeO-DMT (5-methoxy-N,N-dimethyltryptamine), 5-methoxy-3,4-methylenedioxyamphetamine, acetorphine, acetorphine, acetyl-alpha-methylfentanyl, acetyl-alpha-methylfentanyl, acetyldihydrocodone, acetylmethadol, acetylmethadol, alfentanil, allobarbital, allylprodine, alphacetylmethadol except levo-alphacetylmethadol, alpha-ethyltryptamine, alphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amilnitrite (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylcetone, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamine, bromazepam, brotizolam, bufotenine, buprenorphine, butabarbital, butalbital, butobarbital, butorphanol, BZP (A2)(1-benzylpiperazin), camazepam, cannabis, carfentanil, catha edulis, cathine, cathinone, chloral betaine, chloral hydrate, chlordiazepoxide, chlorhexadol, chlorotestosterone (same as clostebol), chlorphentermine, clobazam, clonazepam, clonitazene, clonitazene, clorazepate, clortermine, clostebol, clotiazepam, cloxazolam, coca leaves, cocaine, codeine, codeine and isoquinoline alkaloid, codeine methylbromide, codeine-N-oxide, codoxime, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodone, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidine, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the species psilocybe semilanceata, furethidine, gamma hydroxybutyric acid, glutethimide, halazepam, haloxazolam, heroine, hydrocodone, hydrocodone & isoquinoline alkaloid, hydromorphinol, hydromorphone, hydroxypethidine, ibogaine, isobutyl nitrite, isomethadone, ketamine, ketazolam, ketobemidone, levamfetamine, levo-alphacetylmethadol, levo-methamphetamine, levomethorphan, levomoramide, levophenacylmorphan, levorphanol, lis dexamfetamine, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine), mCPP (1-(3-chlorphenyl)piperazine), mebutamate, mecloqualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandrolone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrol, piritramide, PMMA (paramethyxymethyl amphetamine), prazepam, proheptazine, properidine, propiram, psilocybine, psilocine, pyrovalerone, quazepam, racemethorphane, racemoramide, racemorphane, remifentanil, salvia divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamine, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine and zolazepam in combination, tilidine, trenbolone, triazolam, trimeperidine, vinbarbital, zaleplon, zipeprol, zolpidem, or zopiclone.

Other suitable examples of active drug substances suitable for use in the pharmaceutical compositions described herein include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodone, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narcine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, or pethidine.

Other examples of active drug substances suitable for use in the pharmaceutical compositions described herein include anabolic steroids, cannabis, cocaine, or diazepam.

In another embodiment, the active drug substance comprises the therapeutic classes including non-steroidal anti-inflammatory substances or antirheumatic active drug substances.

In other embodiments, the active drug substance comprises analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-adrenergic, serotonin, H3 antagonists used for ADHD or nootropics agents used in addictive disorders.

In other embodiments, the active drug substance comprises therapeutic classes including anaesthetics, centrally acting analgesics, sedative-hypnotics, anxiolytics, appetite suppressants, decongestants, antitussives, antihistamines, antiemetics, antidiarrheals, and drugs used to treat narcolepsy, or attention deficit hyperactivity disorder.

In another embodiment, the active drug substance is associated with abuse syndromes and the active drug substance may, for example, be selected from opioids, CNS depressants, CNS stimulants, cannabinoids, nicotine-like compounds, glutamate antagonists, or N-methyl-D-aspartate (NMDA) antagonists.

In another embodiment, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodone, diamorphine, tapentadol, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, or ziconotide.

In another embodiment, the active drug substance is an opioid. Where an opioid is included as an active drug substance, the opioid may comprise naturally occurring opioids, synthetic opioids, or semisynthetic opioids.

In other embodiment, the active drug substance comprises amfetamine, dexamfetamine, lisdexamfetamine, metamfetamine, methylphenidate, dexmethylphenidate, or combinations thereof.

In another embodiment, the pharmaceutical compositions disclosed herein includes an opioid, the opioid is selected from buprenorphine, codeine, dextromoramide, dihydrocodone, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semi-crystalline, or amorphous or polyamorphous forms.

Some embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In other embodiments, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

In another embodiment, the active pharmaceutical ingredient is hydrocodone or oxycodone or a pharmaceutically acceptable salt form of either hydrocodone or oxycodone. Pharmaceutically acceptable salts forms are those formed by contacting hydrocodone or oxycodone free base with a suitable acid in a suitable solvent under suitable conditions that will form a form of hydrocodone or oxycodone acid addition salt. Suitable acids include hydrochloric acid, camphorsulfonic acid, hydrobromic acid, sulfuric acid, methanesulfonic acid, formic acid, acetic acid, oxalic acid, succinic acid, tartaric acid, mandelic acid, malic acid, salicylic acid, fumaric acid, lactic acid, citric acid, glutamic acid, and/or aspartic acid.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

The concentration of the active pharmaceutical ingredient in the pharmaceutical composition described herein depends on the specific active pharmaceutical ingredient substance, the disease to be treated, the condition of the patient, the age, and gender of the patient, etc. The active pharmaceutical ingredient may be known and a person skilled in the art will be able to find information as to the dosage of each active drug substance and, accordingly, will know how to determine the amount of each active drug substance in the pharmaceutical composition.

The active pharmaceutical ingredient may be a new chemical entity for which the amount of information is limited. In such cases, the dosage has to be evaluated based on available preclinical and/or clinical data.

In some embodiments described herein, the pharmaceutical composition comprises a dosage form comprising a soft capsule shell or a hard capsule shell.

In one embodiment, the soft capsule shell has the composition of Table 2, including all possible iterations of the specified ranges that provide 100% for the total weight percentage, including or excluding the optional colorings, flavorings, or excipients.

TABLE 2

Exemplary soft gelatin capsule composition

| Component | Exemplary Component | Weight Percentage (%) |
| --- | --- | --- |
| Film-forming polymer | Gelatin | 20-36 (Gelatin) |
| Plasticizer | Glycerol | 10-30 |
| Solvent | Water | 20-70 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the enteric soft capsule shell has the exemplary composition shown in Table 3.

TABLE 3

Exemplary Soft Capsule Shell Composition

| Component | Percent weight (%) |
| --- | --- |
| Gelatin | 43 |
| Glycerol | 20 |
| Titanium dioxide (optional) | 0.7 |
| Coloring agent (optional) | 0.1 |
| Water | 36.2 |
| TOTAL | 100% |
| Final pH | ~4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment described herein, the enteric soft capsule described herein comprises a composition of about 3% to about 10% film forming polymer (e.g., a composition of carrageenan); about 10% to about 30% filler; about 10% to about 30% plasticizer; and about 30% to about 70% solvent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming 1 polymer weight percentage is about 42%. In another aspect, the film-forming polymer weight percentage is about 44%.

In one embodiment, the weight percentage range of film-forming polymer of the soft capsule described herein is about 3% to about 15%, including all integers within the specified range. In one aspect, the film-forming polymer weight percentage is about 3%. In one aspect, the film-forming polymer weight percentage is about 5%. In one aspect, the film-forming polymer weight percentage is about 7%. In one aspect, the film-forming polymer weight percentage is about 10%. In one aspect, the film-forming polymer weight percentage is about 12%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In another embodiment described herein, the pharmaceutical composition comprises an enteric soft capsule shell comprising a matrix fill comprising an active pharmaceutical ingredient.

Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

Film-former polymers that are useful for creating enteric soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), alginic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth) acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs.

Plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 4, including all possible iterations of the specified ranges that provide 100% for the total weight percentage, including or excluding the optional, excipients, opacifiers, colorants, and flavorings.

TABLE 4

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer | 8-20 |
| Plasticizer | Glycerol, Triethyl citrate | 15-22 |
| Alkali neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, an enteric soft capsule shell comprises a composition of about 30% film forming polymer (e.g., gelatin); about 10% enteric, acid insoluble polymer; about 20% plasticizer; about 1% alkali neutralizing agent; and about 37% solvent.

In one embodiment described herein, the enteric soft capsule described herein comprises a composition of about 3% film forming polymer (e.g., a composition of carrageenan); about 10% enteric, acid insoluble polymer; about 10% filler; about 10% plasticizer; about 1% alkali neutralizing agent; about 2% sealant; and about 60% solvent.

In one embodiment, the weight percentage range of total polymer content (i.e., film forming polymer and enteric acid-insoluble polymer) of the enteric soft capsule described herein is about 30% to about 45%, including all integers within the specified range. In another embodiment, the weight percentage range of total polymer content (i.e., film forming polymer and enteric acid-insoluble polymer) of the enteric soft capsule described herein is about 9% to about 35%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%. In another aspect, the total polymer weight percentage is about 12%. In another aspect, the total polymer weight percentage is about 16%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the weight ratio range of film forming polymer to enteric acid insoluble polymer (film forming: enteric) is about 25:75 (0.33) to about 40:60 (0.67) (i.e., ≈0.33-0.67), including all iterations of ratios within the specified range. In one aspect, the ratio of film forming polymer to enteric acid insoluble polymer is about 30:70 (≈0.43). In another aspect, the ratio of film forming polymer to enteric acid insoluble polymer is about 28:72 (≈0.38).

In another embodiment described herein, the weight ratio range of film forming polymer (i.e., total carrageenan composition) to enteric acid insoluble polymer (film forming: enteric) in the enteric soft gel composition is about 3:9 (≈0.3) to about 4:3 (≈4.3) (i.e., ≈0.3-1.3) including all ratios within the specified range. In some aspects, the ratio of film forming polymer to enteric acid insoluble polymer in the gel mass is about 1:3 (≈0.33), about 1:2.5 (≈0.4), about 1:2 (≈0.5), about 1:1.6 (≈0.6), about 1:1.25 (≈0.8), about 1:1 (≈1), about 1.1:1 (≈1.1), about 1.21 (≈1.2), or about 1.3:1 (≈1.3). In one aspect, the ratio of film forming polymer to enteric acid insoluble polymer in the gel mass is about 1:2.5 (≈0.4). In another aspect, the ratio of film forming polymer to enteric acid insoluble polymer is about 1:3 (≈0.3).

In one embodiment, the weight ratio of total plasticizer to film forming polymer is about 20:40 to 21:30 (i.e., ≈0.5-0.7), including all iterations of ratios within the specified range. In one aspect, the weight ratio of total plasticizer to film forming polymer is about 20:40 (≈0.5). In another aspect, the weight ratio of total plasticizer to film forming polymer is about 21:30 (≈0.7). In another aspect, the weight ratio of total plasticizer to film forming polymer is about 19:29 (≈0.65). In another aspect, the weight ratio of total plasticizer to film forming polymer is about 19.3:29.2 (≈0.66).

In one embodiment, the weight ratio of total plasticizer to enteric acid insoluble polymer is about 1:1 to about 2:1 (≈1-2), including all iterations of ratios within the specified range. In one aspect, the weight ratio of total plasticizer to enteric acid insoluble polymer is about 11:10 (≈1.1). In another aspect, the weight ratio of total plasticizer to enteric acid insoluble polymer is about 14:10 (≈1.4). In another aspect, the weight ratio of total plasticizer to enteric acid insoluble polymer is about 17:10 (≈1.7). In another aspect, the weight ratio of total plasticizer to enteric acid insoluble polymer is about 20:10 (≈2). In another aspect, the weight ratio of total plasticizer to enteric acid insoluble polymer is about 19.3:11.2 (≈1.73).

In one embodiment, the weight ratio range of total plasticizer to total polymer (film forming and enteric acid insoluble polymer) is about 18:45 to about 20:40 (i.e., ≈0.40-0.5), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 5.

TABLE 5

Exemplary Enteric Soft Capsule Shell Composition

| Component | Percent weight |
|---|---|
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | ~4-9 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In some embodiments, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films that form the enteric capsule and the dimensions of the capsules are similar to those described herein.

In another embodiment, the capsule is a soft capsule comprising a film-forming polymer that is stable at higher temperatures (e.g., about 50° C. to about 80° C.). An exemplary film-forming polymer is carrageenan (e.g., kappa or iota carrageenan). Exemplary, non-limiting soft capsules comprising carrageenan are described in the International Patent Application Publication No. WO 2003/061633; U.S. Patent Application Publication No. US 2004/0052839; and U.S. Pat. Nos. 6,949,256 and 7,887,838, each of which is incorporated by reference herein for such teachings. In one aspect, soft capsules comprising a film-forming polymer stable at high temperatures allow for matrix fills having a higher viscosity to be encapsulated minimizing the use of additional plasticizers. The increased encapsulation temperature, for example, from about 50° C. to about 80° C. allows for a viscous matrix at a lower temperature to exhibit flowability for encapsulation by the methods described herein (e.g., rotary die encapsulation).

In another embodiment, the capsule shell is a hard capsule shell. In one aspect, the hard capsule shell may comprise the abuse deterrent matrices described herein. Any hard capsule shell, for example hard capsule shells comprising gelatin, HPMC, or pullulan, including hard capsule shells exhibiting enteric properties, maybe used with the abuse deterrent matrix fills described herein. Hard capsule shells are known in the art and are described by Kathpalia et al., *J. Adv. Pharm. Edu. & Res.* 4(2): 165-177 (2014), which is incorporated by reference herein for the specific teachings related to hard capsules.

Another embodiment is a controlled release pharmaceutical composition comprising a capsule shell encapsulating a matrix fill comprising one or more active pharmaceutical ingredients, wherein the capsule shell comprises one or more subcoatings, coatings, or topcoatings. Suitable coatings may be adherence coatings, enteric coatings, moisture barriers, air or gas barriers, polymer coatings, colorings, flavors, writings, or combinations thereof.

Exemplary polymers useful for coatings include cellulose acetate phthalate, hydroxypropylmethyl cellulose phthalate, hydroxypropyl methylcellulose acetate succinate, polyvinyl acetate phthalate, polyvinyl alcohols, cellulose acetate trimellitate, carboxymethylcellulose, methacrylic acid copolymers such as, Eudragit L (polymethacrylic acid, methylmethacrylate, 1:1 ratio), or Eudragit S (polymethacrylic acid, methylmethacrylate, 1:2 ratio), shellac, zein, or combinations thereof.

Suitable plasticizers include acetyl triethyl citrate, dibutyl phthalate, tributyl citrate, triethyl citrate, acetyl tributyl citrate, propylene glycol, triacetin, polyethylene glycol, diethyl phthalate, or combinations thereof.

Suitable solubilizers include sodium lauryl sulfate, sodium lauroyl sarcosinate sodium dodecyl sulfate, polysorbate 20, polysorbate 80, other detergents or surfactants, or combinations thereof.

Anti-adherent agents serve to prevent potential agglomeration in acid media. Suitable anti-adherents include talc, magnesium stearate, calcium stearate, stearic acid, hydrogenated vegetable oils, polyethylene glycols, fumed silica, silicon dioxide, or combinations thereof.

Pore-forming agents serve to create pores or channels in the enteric coating after administration to a human. Suitable pore-forming agents include sodium chloride, potassium chloride, sucrose, sorbitol, mannitol, polyethylene glycols (PEG), propylene glycol, hydroxypropyl cellulose, hydroxypropyl methylcellulose, polyvinyl alcohols, methacrylic acid copolymers, poloxamers, or combinations thereof.

Many conventional coating excipients are described in the art. See e.g., Rowe et al., Eds. *Handbook of Pharmaceutical Excipients*, 7$^{th}$ ed. Royal Pharmaceutical Society, UK (2012).

In one embodiment, adjusting the amount of coating and the ratio of polymer to other components allows for tuning the release profile of the dosage form.

Subcoats can be applied to the capsules prior to coating to prevent shell-coat interactions and improve coating adhesion to the capsule. Exemplary subcoatings can comprise polyvinylpyrrolidone, polyvinyl alcohols, hydroxypropyl methylcellulose, polyethylene glycol, oils, or combinations thereof.

Coatings, top coatings, or subcoatings are applied to the exterior of a capsules using various methods know in the art. The coatings are typically prepared as suspensions and sprayed on capsules in perforated coating pans through one or more spray nozzles at a specific temperature. Coating solutions or dispersion may be applied at spray rates between 100 and 400 g/min. The spray rate may be proportionately higher for coatings with higher solid content and lower for more dilute dispersions. In one embodiment, capsules are coated using a pan coater. After the coating suspension is applied, the coated capsules are dried in the pan coater for a specific period of time at a specific temperature.

Another embodiment described herein comprises a subcoating that is applied prior to applying a coating. In one embodiment, the subcoating comprises hydroxypropyl methylcellulose, methylcellulose, ethylcellulose, or a combination thereof.

Another embodiment described herein comprises a coating that is applied directly on the exterior of the capsule. In one embodiment, the coating comprises polyvinyl alcohol, polyvinyl acetate hydroxpropyl methylcellulose, methylcellulose, ethylcellulose, or a combination thereof.

Another embodiment described herein comprises a moisture barrier that is applied as a coating. The moisture barrier can be applied directly to the capsule or on top of a subcoating. In one embodiment the moisture barrier comprises one or more polyvinyl alcohols and appropriate pharmaceutically acceptable excipients. In one embodiment the moisture barrier comprises polyvinyl alcohol, sodium lauryl sulfate, glyceryl mono-caprylate-caprate, and talc. In one aspect, the moisture barrier aids in preserving the cosmetic appearance of the dosage forms by preventing dimpling, sticking, or other processing or storage induced blemishes. In one embodiment, the polyvinyl alcohol coating comprises Opadry® amb II, (Colorcon).

Without being bound by any theory, it is believed that a coating such as polyvinyl alcohol applied to achieve about 10% to about 15% weight gain of the dosage form permits the dosage form to be annealed at a temperature of about 60° C. to about 75° C. for about 10 min to about 90 min and slowly cooled to room temperature without causing cosmetic defects such as dimpling, flattening, sticking, or other defects. It is believed that the coating protects the soft gelatin capsule and prevents it from becoming molten or tacky during the annealing and cooling steps.

In one embodiment, a coating is applied to the capsule dosage form to achieve about a 10% to about 15% weight gain to the dosage form. In one aspect, the weight gain is about 10% to about 20%, including each integer within the specified range. In one aspect the weight gain is about 8%, about 9%, about 10%, about 11%, about 12%, about 13%, about 14%, about 15%, about 16%, about 17%, about 18%, about 19%, or about 20%. In another embodiment, a first coating is applied to achieve about a 10% weight gain. In another embodiment, a second coating comprising one or more coloring agents is applied to the first coated dosage form to achieved about a 5% weight gain, for a total coating weight gain of about 12% to about 15%.

The pharmaceutical composition described herein can comprise a soft or hard capsule comprising a matrix fill that is liquid, semi-solid, or solid. Capsules prepared as described herein can contain a hydrophobic solution, suspension, or lipid or lipophilic vehicle comprising vegetable oils, shortening, or waxes, or combinations thereof. In some aspects described herein, the lipid or lipophilic vehicle may comprise one or more hydrophilic polymers, but as described herein, the vehicle is considered a lipid or lipophilic vehicle. The composition can be formulated to prevent interaction with the capsule shell components and release the pharmaceutical composition at a specified rate.

Additional pharmaceutical excipients useful for the pharmaceutical composition as described herein include, for example, the following: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl alcohol, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); Sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agent (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

One embodiment described herein, is a pharmaceutical composition comprising any of the formulations shown in the Tables or Examples described herein. Any of the components of the formulations shown in the Tables or Examples can be increased, decreased, combined, recombined, switched, or removed to provide for a formulation comprising about 100% by weight.

Another embodiment described herein is a method for preparing abuse deterrent pharmaceutical compositions comprising the abuse deterrent controlled release matrix described herein comprising (a) mixing one or more optional viscosity modifiers, one or more release modifiers, and one or more antioxidants in one or more flowability enhancers to form a first mixture; (b) adding one or more active pharmaceutical ingredient to the first mixture to form a matrix fill mixture; (c) filling the matrix fill mixture into capsule shells using standard rotary die encapsulation techniques; and (d) annealing the capsules at an elevated temperature for a period of time. In one aspect, the flowability enhancer is heated to a first elevated temperature prior to mixing the viscosity modifier and/or release modifiers. In another aspect, the flowability enhancer or mixture comprising the flowability enhancer is cooled to a second temperature. In another aspect, the flowability enhancer or mixture comprising the flowability enhancer is cooled to a third temperature. In another aspect, the one or more viscosity modifiers are added to the heated flowability enhancer before adding the one or more release modifiers. In another aspect, the heated mixture is cooled to a second elevated temperature prior to adding the active pharmaceutical ingredient and the one or more release modifiers. In another aspect, the active pharmaceutical ingredient is added prior to adding the one or more release modifiers. In another aspect, one or more antioxidants are added prior to adding the one or more release modifiers. In another aspect, a first viscosity modifier is added to the flowability enhancer at a first temperature, followed by cooling the mixture to a second temperature and adding one or more antioxidants to the mixture, and cooling the mixture to a third temperature and adding the active pharmaceutical ingredient and release modifier.

In another embodiment, the method for preparing the abuse deterrent pharmaceutical compositions described herein comprise (a) heating one or more flowability enhancers to a first temperature; (b) adding one or more antioxidants and mixing; (c) adding one or more release modifiers to the mixture of b; (d) cooling the mixture to a second temperature; (e) adding one or more active pharmaceutical ingredients to the cooled mixture of step d; (f) deaerating the mixture of step e; (g) filling the deaerated mixture of step f into capsule shells using rotary die encapsulation techniques; (h) annealing the capsules at an elevated temperature for a period of time; and (i) slowly cooling the annealed capsules of h to room temperature in a controlled manner. In one aspect, the elevated annealing temperature of step h is from about 60° C. to about 80° C. and the period of time is from about 30 min to about 120 min. In one aspect, the controlled cooling of step i comprises cooling the capsules at a rate of about 5° C. per about 10 to about 15 min.

In another embodiment, the method for preparing the abuse deterrent pharmaceutical compositions described herein comprise (a) heating one or more flowability enhancers to a first temperature; (b) adding one or more viscosity modifiers to the heated flowability enhancer and mixing; (c) cooling the mixture of step b to a second temperature; (d) adding one or more antioxidants to the mixture of step c and mixing; (e) cooling the mixture of step d to a third temperature; (f) adding one or more release modifiers and the active pharmaceutical ingredient to the cooled mixture of step e and mixing; (g) filling the matrix fill mixture into capsule shells using standard rotary die encapsulation techniques; (h) annealing the capsules at an elevated temperature for a period of time; and (i) cooling the capsules to room temperature in a controlled manner. In one aspect, the elevated annealing temperature of step h is from about 60° C. to about 80° C. and the period of time is from about 30 min to about 120 min. In one aspect, the controlled cooling comprises cooling the capsules at a rate of about 5° C. per about 10 to about 15 min.

Another embodiment described herein is a method for manufacturing an abuse deterrent pharmaceutical composition comprising (a) heating one or more flowability enhancers to about 55° C. to about 70° C. under nitrogen; (b) adding one or more antioxidants to the flowability enhancer and mixing at about 50 to about 300 RPM until dissolved; (c) cooling the mixture of step b to about 25° C. to about 35° C. while mixing at about 50 to about 300 RPM; (d) adding the active pharmaceutical ingredient and mixing at about 50 to about 300 RPM for about 30 min; (e) adding a viscosity modifier to the mixture of step d and mixing at about 50 to about 300 RPM for about 30 min; (f) deaerating the mixture of step e for at least about 30 min; (g) maintaining the deaerated mixture at a third temperature with continuous mixing at about 50 to about 100 RPM under nitrogen during encapsulation; (h) encapsulating the mixture of step g into soft capsule shells using rotary die encapsulation; (i) drying the capsules; (i) removing processing lubrication with isopropyl alcohol; (j) transferring the capsules to a coating pan operating at about 1-2 RPM at a temperature of about 30° C. to about 35° C.; (k) coating the capsules of step j with a coating composition at about 1-2 RPM until about 10% to about 20% weight gain is achieved; (l) heating the capsules of step k to about 60° C. to about 80° C. for about 30 min to about 90 min at about 1-2 RPM; (m) cooling the capsules of step l to about 30° C. at a rate of about 2° C. to about 10° C. per each about 5 min to about 20 min period while maintaining about 1-2 RPM; (n) cooling the capsules of step m from about 30° C. to room temperature (ca. 25° C.) while maintaining about 1-2 RPM; (o) printing labels on the capsule; and (p) packaging the capsules. In one aspect described herein, the coating and annealing process are conducted in a coating pan.

In one embodiment, the methods for preparing the abuse deterrent pharmaceutical compositions described herein comprise heating the flowability enhancer or a mixture comprising the flowability enhancer to a first temperature. In one aspect, the first temperature is about 40° C. to about 170° C., including each integer within the specified range. In another aspect, the first temperature is about 120° C. to about 170° C., including each integer within the specified range. In another aspect, the first temperature is about 40° C. to about 90° C., including each integer within the specified range. In another aspect, the first temperature is about 40° C. to about 90° C., including each integer within the specified range. In another aspect, the first temperature is about 40° C., about 45° C., about 50° C., about 55° C., about 60° C., about 65° C., about 70° C., about 75° C., about 80° C., about 90° C., about 100° C., about 110° C., about 120° C., about 130° C., about 140° C., about 150° C., about 160° C., or about 170° C.

In another embodiment, the methods for preparing the abuse deterrent pharmaceutical compositions described herein comprise cooling the flowability enhancer or a mixture comprising the flowability enhancer to a second temperature. In one aspect, the second temperature is about 25° C. to about 100° C., including each integer within the specified range. In another aspect, the second temperature is about 25° C. to about 50° C., including each integer within the specified range. In another aspect, the second temperature is about 40° C. to about 90° C., including each integer within the specified range. In another aspect, the second temperature is about 40° C. to about 90° C., including each integer within the specified range. In another aspect, the second temperature is about 25° C., about 30° C., about 35° C., about 40° C., about 45° C., about 50° C., about 55° C., about 60° C., about 65° C., about 70° C., about 75° C., about 80° C., about 90° C., or about 100° C.

In another embodiment, the methods for preparing the abuse deterrent pharmaceutical compositions described herein comprise cooling the flowability enhancer or a mixture comprising the flowability enhancer to a third temperature. In one aspect, the third temperature is about 25° C. to about 100° C., including each integer within the specified range. In another aspect, the third temperature is about 25° C. to about 50° C., including each integer within the specified range. In another aspect, the third temperature is about 40° C. to about 90° C., including each integer within the specified range. In another aspect, the third temperature is about 40° C. to about 90° C., including each integer within the specified range. In another aspect, the third temperature is about 25° C., about 30° C., about 35° C., about 40° C., about 45° C., about 50° C., about 55° C., about 60° C., about 65° C., about 70° C., about 75° C., about 80° C., about 90° C., or about 100° C.

In another embodiment, the methods for preparing the abuse deterrent pharmaceutical compositions described herein comprise annealing the pharmaceutical composition comprising a soft or capsule shell and a matrix fill as described herein at specified temperature for a period of time. In one aspect, the temperature ranges from about 45° C. to about 120° C., including each integer within the specified range. In another aspect, the temperature ranges from about 55° C. to about 85° C., including each integer within the specified range. In another aspect, the temperature is about 45° C., about 50° C., about 55° C., about 60° C., about 65° C., about 70° C., about 75° C., about 80° C., about 90° C., about 100° C., about 110° C., or about 120° C. In another aspect, the annealing time ranges from about 10 minutes to about 160 minutes, including each integer within the specified range. In another aspect, the annealing time ranges from about 1 minute to about 80 minutes, including each integer within the specified range. In another aspect, the annealing time ranges from about 40 minutes to about 80 minutes, including each integer within the specified range. In another aspect, the annealing time is about 1 min, about 3 min, about 6 min, about 9 min, about 12 min, about 15 min, about 20 min, about 25 min, about 30 min, about 35 min, about 40 min, about 45 min, about 50 min, about 55 min, about 60 min, about 70 min, about 80 min, about 90 min, about 100 min, about 110 min, about 120 min, about 130 min, about 140 min, about 150 min, or about 160 min.

In another embodiment, the abuse deterrent pharmaceutical composition described herein provides a dosage of an active pharmaceutical ingredient described herein for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In one embodiment, the dosage may be administered to a human in need of management of moderate to severe chronic pain and neuropathic pain associated with diabetic peripheral neuropathy (DPN), when a continuous, persistent (around-the-clock) opioid analgesic is needed for an extended period of time.

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition, including but not limited to, pain.

In one embodiment, the pharmaceutical composition described herein is administered in multiple dosages simultaneously to achieve a desired dose. For example, two or more identical dosages are administered at one time to achieve a desired dose. Two 40 mg dosage forms may be administered simultaneously to provide 80 mg. Likewise, three 40 mg dosage forms or four 30 mg dosage forms may be administered simultaneously to provide 120 mg. In another embodiment, two or more different dosages are administered at one time. Such dual or different simultaneous doses can be used to provide an effective dose of the pharmaceutical composition to a subject in need thereof.

In one embodiment, the abuse deterrent oral composition described herein, comprises one or more active pharmaceutical ingredients in an amount of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or even more.

In another embodiment, the abuse deterrent oral composition described herein, comprises one or more active pharmaceutical ingredients in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg.

In one embodiment described herein, the abuse deterrent oral composition described herein may comprise an active pharmaceutical ingredient load (e.g., a drug load of one or more active pharmaceutical ingredients) of about 1% to about 90%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 3%. In one aspect, the drug load is about 5%. In one aspect, the drug load is about 6%. In one aspect, the drug load is about 9%. In one aspect, the drug load is about 10%. In one aspect, the drug load is about 12%. In one aspect, the drug load is about 15%. In one aspect, the drug load is about 20%. In one aspect, the drug load is about 25%. In one aspect, the drug load is about 30%. In one aspect, the drug load is about 35%. In one aspect, the drug load is about 40%. In one aspect, the drug load is about 50%. In one aspect, the drug load is about 60%. In one aspect, the drug load is about 28%. In one aspect, the drug load is about 32%. In one aspect, the drug load is about 44%. In one embodiment, the drug load is about 48%.

In one embodiment, the active pharmaceutical ingredient is oxycodone, hydrocodone or codeine, or a salt, ether, ester, variant, or derivative thereof. In one embodiment, the active pharmaceutical ingredient is oxycodone. In one embodiment, the active pharmaceutical ingredient is oxycodone hydrochloride. In another embodiment, the active pharmaceutical ingredient is hydrocodone. See Prescribing Information for OxyContin® ER 04/2014 (Purdue Pharma LP; available at www.purduepharma.com) and Zohydro® ER 01/2015 (Zogenix® Inc.; available at: www.zogenix.com), which are incorporated by reference herein for such teachings.

In another embodiment, the active pharmaceutical ingredient may comprise oxycodone, hydrocodone, or codeine and an additional active pharmaceutical ingredient. In one aspect, the additional active pharmaceutical ingredient prevents opioid abuse when an excess of opioid is used. In another aspect, the additional active pharmaceutical ingredient reduces or prevents opioid induced side effects.

In one embodiment, the active pharmaceutical ingredient comprises oxycodone hydrochloride. The oxycodone may comprise trace amounts of impurities from the manufacturing process. In one embodiment described herein, the oxycodone hydrochloride comprises greater than 25 ppm of 14-hydroxycodeinone, but less than 100 ppm. In another embodiment the oxycodone hydrochloride comprises about 50 ppm of 14-hydroxycodeinone. In another embodiment the oxycodone hydrochloride comprises about 90 ppm of 14-hydroxycodeinone. In another embodiment the oxycodone hydrochloride comprises <100 ppm of 14-hydroxycodeinone.

In one embodiment, the abuse deterrent oral composition described herein comprises a dose of opioid analgesic. In one aspect, the dose of opioid analgesic is about 5 mg. In one aspect, the dose of opioid analgesic is about 10 mg. In one aspect, the dose of opioid analgesic is about 20 mg. In another aspect, the dose of opioid analgesic is about 30 mg. In another aspect, the dose of opioid analgesic is about 40 mg. In another aspect, the dose of opioid analgesic is about 50 mg. In another aspect, the dose of opioid analgesic is about 60 mg. In another aspect, the dose of opioid analgesic is about 70 mg. In another aspect, the dose of opioid analgesic is about 80 mg. In another aspect, the dose of opioid analgesic is about 90 mg. In another aspect, the dose of opioid analgesic is about 100 mg. In another aspect, the dose of opioid analgesic is about 120 mg. In another aspect, the dose of opioid analgesic is about 140 mg. In another aspect, the dose of opioid analgesic is about 160 mg. In another aspect, the dose of opioid analgesic is about 180 mg. In another aspect, the dose of opioid analgesic is about 200 mg.

In one embodiment, the abuse deterrent oral composition described herein comprises a dose of oxycodone. In one aspect, the dose of oxycodone is about 5 mg. In another aspect, the dose of oxycodone is about 10 mg. In another aspect, the dose of oxycodone is about 15 mg. In another aspect, the dose of oxycodone is about 20 mg. In another aspect, the dose of oxycodone is about 30 mg. In another aspect, the dose of oxycodone is about 40 mg. In another aspect, the dose of oxycodone is about 50 mg. In another aspect, the dose of oxycodone is about 60 mg. In another aspect, the dose of oxycodone is about 70 mg. In another aspect, the dose of oxycodone is about 80 mg. In another aspect, the dose of oxycodone is about 100 mg. In another aspect, the dose of oxycodone is about 120 mg. In another aspect, the dose of oxycodone is about 140 mg. In another aspect, the dose of oxycodone is about 160 mg. In another aspect, the dose of oxycodone is about 180 mg. In another aspect, the dose of oxycodone is about 200 mg.

In another embodiment, the total dosage of oxycodone administered in a 24-hour period is about 20 mg to about 600 mg per 24-hour period. In one aspect, the total dosage of oxycodone or hydrocodone administered in a 24-hour period is about 50 mg to about 250 mg per 24-hour period. The dosage can contain a total amount of oxycodone effective for treatment, amelioration, prophylaxis, or reducing the onset of or symptoms of pain.

In one embodiment, the recommended dosage is based upon the condition of the subject in need thereof. The subject can comprise a human or mammal in need thereof. In one aspect, the need is defined as a painful condition or perception of pain. In one embodiment, the perception of pain is described as a numerical scale. In one aspect, this numerical scale indicates 0 for no pain, 1-3 suggestive of mild pain; annoying or nagging pain that does not affect the activities of daily life, 4-6 for moderate pain that interferes significantly with the activities of daily life, and 7-10 for severe pain that is disabling for which the activities of daily life are not possible. Another aspect described herein comprises orally administering a maximal dosage of about 10 mg to about 120 mg of oxycodone every 24 hours for humans or mammals with a pain of 1-3. Another aspect described herein comprises orally administering a maximal dosage of about 80 mg to about 400 mg of oxycodone every 24 hours for humans or mammals with a pain of 4-6. Another aspect described herein comprises orally administering a maximal dosage of 120 mg to about 600 mg of oxycodone every 24 hours for humans or mammals with a pain of 7-10. In one aspect, the level of pain is assessed by observing the human or mammal.

Another aspect described herein comprises orally administering a delayed release dosage of about 10 mg of oxycodone every 12 hours for a human or mammal with a pain of 1-3. Another aspect described herein comprises orally administering a delayed release dosage of about 30 mg of oxycodone 1 every 12 hours for a human or mammal with a pain of 4-6. Another aspect described herein comprises orally administering a delayed release dosage of about 80 mg of oxycodone every 12 hours for a human or mammal with a pain of 7-10. Another aspect described herein comprises increasing the delayed release dosage of oxycodone by 10 mg increments every 24 hours to a maximal daily dosage of 600 mg if pain of any type is not ameliorated in the human or mammal in need thereof. Another aspect described herein comprises decreasing the dosage of oxycodone as needed every 24 hours if pain of any type has decreased or has been ameliorated in the human or mammal in need thereof.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of opioid analgesic is 10 mg to about 40 mg. In one aspect, an initial dose of about 10 mg to about 40 mg is suitable for a subject that not tolerant of an opioid. In one aspect, the initial dose is about 10 mg of opioid analgesic. In another aspect, the initial dose is about 20 mg of opioid analgesic. In another aspect, the initial dose is about 20 mg of opioid analgesic. In another aspect, the initial dose is about 30 mg of opioid analgesic. In another aspect, the initial dose is about 40 mg of opioid analgesic. In another aspect, the dose of opioid analgesic may be maintained and given every 8 to 12 hours. In another aspect, the dose of opioid analgesic may be increased by about 10 mg to about 20 mg every 8 hrs to 12 hrs until pain relief occurs.

In another embodiment, the initial dosage of opioid analgesic is 40 mg to about 80 mg. In one aspect, an initial dose of about 40 mg to about 80 mg is suitable for a subject that has an opioid tolerant phenotype. In one aspect, the initial dose is about 40 mg of opioid analgesic. In another aspect, the initial dose is about 50 mg of opioid analgesic. In another aspect, the initial dose is about 60 mg of opioid analgesic. In another aspect, the initial dose is about 70 mg of opioid analgesic. In another aspect, the initial dose is about 80 mg of opioid analgesic. In another aspect, the dose of opioid analgesic may be maintained and given every 8 to 12 hours. In another aspect, the dose of opioid analgesic may be increased by about 10 mg to about 20 mg every 8 hrs to 12 hrs until pain relief occurs.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of oxycodone is 10 mg to about 40 mg. In one aspect, an initial dose of about 10 mg to about 40 mg is suitable for a subject that not tolerant of an opioid and a dose. In one aspect, the initial dose is about 10 mg of oxycodone. In another aspect, the initial dose is about 20 mg of oxycodone. In another aspect, the initial dose is about 20 mg of oxycodone. In another aspect, the initial dose is about 30 mg of oxycodone. In another aspect, the initial dose is about 40 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until pain relief occurs.

In another embodiment, the initial dosage of oxycodone is 40 mg to about 160 mg. In one aspect, an initial dose of about 40 mg to about 80 mg is suitable for a subject that has an opioid tolerant phenotype. In one aspect, the initial dose is about 40 mg of oxycodone. In another aspect, the initial dose is about 50 mg of oxycodone. In another aspect, the initial dose is about 60 mg of oxycodone. In another aspect, the initial dose is about 70 mg of oxycodone. In another aspect, the initial dose is about 80 mg of oxycodone. In another aspect, the initial dose is about 100 mg of oxycodone. In another aspect, the initial dose is about 120 mg of oxycodone. In another aspect, the initial dose is about 140 mg of oxycodone. In another aspect, the initial dose is about 160 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until pain relief occurs.

Additionally, the abuse deterrent pharmaceutical compositions described herein may be useful for the treatment of pain stemming from, including but not limited to, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, trauma, or granuloma annulare.

Another embodiment described herein is an abuse deterrent pharmaceutical composition as described herein for administration to a subject having pain, comprising a therapeutically effective amount of one or more active pharmaceutical ingredients, wherein the subject achieves a reduction of pain relative to baseline without substantially experiencing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is an abuse deterrent pharmaceutical composition as described herein for administration to a subject having pain, comprising a therapeutically effective amount of one or more active pharmaceutical ingredients exhibiting an in vitro dissolution rate at pH 1.2 comprising about 35% to about 95% dissolution after about 60 minutes to about 480 minutes including each integer within the specified ranges of dissolution and time. In one aspect, the in vitro dissolution rate at pH 1.2 is about 35% after about 60 min, about 50% after about 120 min, about 70% after about 240 min, about 85% after about 480 min.

Another embodiment described herein is an abuse deterrent pharmaceutical composition as described herein for administration to a subject having pain, comprising a therapeutically effective amount of one or more active pharmaceutical ingredients exhibiting an in vitro dissolution rate at pH 1.2 comprising about 15% to about 95% dissolution after about 60 minutes to about 480 minutes including each integer within the specified ranges of dissolution and time. In one aspect, the in vitro dissolution rate at pH 1.2 is about 10% after about 60 min, about 20% after about 90 minutes, about 50% after about 120 min, about 70% after about 240 min, about 85% after about 480 min.

In another embodiment, the abuse deterrent pharmaceutical composition comprising an abuse deterrent matrix as described herein reduces the dissolution and extraction of an active pharmaceutical ingredient. Suitable non-limiting examples of extraction methods comprise incubating the abuse deterrent pharmaceutical composition in boiling conditions, in aqueous solutions of alcohol, and in distilled water. These methods may be used in conjunction with additional means of agitating, for example, with paddles, dipping, vigourous shaking, physical manipulations, and the like.

In another embodiment, the abuse deterrent pharmaceutical composition as described herein has an in vitro dissolution rate under boiling conditions in an aqueous media (e.g., a temperature of about 90° C. to about 120° C.) is less than about 35% to about 60% after about 10 minutes to about 45 minutes, including each integer within the specified ranges of dissolution and time. In one aspect, the in vitro dissolution rate of the controlled release pharmaceutical composition under boiling conditions in an aqueous media is less than about 50% after about 5 minutes. In another aspect, the in vitro dissolution rate of the controlled release pharmaceutical composition under boiling conditions in an aqueous media is less than about 50% after about 10 minutes. In another aspect, the in vitro dissolution rate of the controlled release pharmaceutical composition under boiling conditions in an aqueous media is less than about 50% after about 20 minutes. In another aspect, the in vitro dissolution rate of the controlled release pharmaceutical composition under boiling conditions in an aqueous media is less than about 50% after about 30 minutes. In another aspect, the in vitro dissolution rate of the controlled release pharmaceutical composition under boiling conditions in an aqueous media is less than about 60% after about 45 minutes.

In another embodiment, the abuse deterrent controlled release pharmaceutical composition as described herein has an in vitro dissolution rate in an aqueous alcohol solution (e.g., an aqueous solution of ethanol of 80%) of less than about 20% to about 50% after about 30 minutes to about 360 minutes, including each integer within the specified ranges of dissolution and time. In one aspect, the in vitro dissolution rate of the controlled release pharmaceutical composition in an aqueous alcohol solution is less than about 10% after about 30 minutes. In another aspect, the in vitro dissolution rate of the controlled release pharmaceutical composition in an aqueous alcohol solution is less than about 20% after about 60 minutes. In another aspect, the in vitro dissolution rate of the controlled release pharmaceutical composition in an aqueous alcohol solution is less than about 50% after about 60 minutes. In another aspect, the in vitro dissolution rate of the controlled release pharmaceutical composition in an aqueous alcohol solution is less than about 50% after about 120 minutes. In another aspect, the in vitro dissolution rate of the controlled release pharmaceutical composition in an aqueous alcohol solution is less than about 50% after about 180 minutes. In another aspect, the in vitro dissolution rate of the controlled release pharmaceutical composition in an aqueous alcohol solution is less than about 50% after about 360 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate at pH 1.2 of about 35% to about 95% after about 60 minutes to about 480 minutes, an in vitro dissolution rate under boiling conditions less than about 35% to about 60% after about 10 minutes to about 45 minutes, and an in vitro dissolution rate in an aqueous alcohol solution of less than about 20% to about 50% after about 30 minutes to about 360 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate as described herein in any one of Drawings 1-7, 9, 11-22, or 28.

Another embodiment described herein is a method for orally administering a dosage form of an abuse deterrent pharmaceutical composition comprising an active pharmaceutical ingredient described herein for the treatment, amelioration, prophylaxis, or reducing the onset of or symptoms of pain.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, wherein the pharmaceutical composition exhibits an in vitro dissolution rate at pH 1.2, of about 35% to about 95% after about 60 minutes to about 480 minutes, an in vitro dissolution rate under boiling conditions less than about 35% to about 60% after about 10 minutes to about 45 minutes, and an in vitro dissolution rate in an aqueous alcohol solution of less than about 20% to about 50% after about 30 minutes to about 360 minutes.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate as described herein in any one of Drawings 1-7, 9, 11-22, or 28.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibit a mean plasma oxycodone $C_{max}$ of about 10 ng/mL to about 150 ng/mL, including each integer within the specified range. In one aspect, the composition is provided in a dosage form containing a total amount of about 10 mg of oxycodone, wherein subjects administered a single dosage exhibit a mean plasma oxycodone $C_{max}$ of about 10 ng/mL. In another aspect, the composition is provided in a dosage form containing a total amount of about 20 mg of oxycodone, wherein subjects administered a single dosage exhibit a mean plasma oxycodone $C_{max}$ of about 20 ng/mL. In another aspect, the composition is provided in a dosage form containing a total amount of about 40 mg of oxycodone, wherein subjects administered a single dosage exhibit a mean plasma oxycodone $C_{max}$ of about 40 ng/mL. In another aspect, the composition is provided in a dosage form containing a total amount of about 80 mg of oxycodone, wherein subjects administered a single dosage exhibit a mean plasma oxycodone $C_{max}$ of about 100 ng/mL.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibit a mean plasma oxycodone $AUC_{0\to\infty}$ of about 100 h·mg/L to about 1000 h·mg/L, including each integer within the specified range. In one aspect, the composition is provided in a dosage form containing a total amount of about 10 mg of an oxycodone, wherein subjects administered a single dosage exhibit a mean plasma oxycodone $AUC_{0\to\infty}$ of about 100 h·mg/L. In another aspect, the composition is provided in a dosage form containing a total amount of about 20 mg of oxycodone, wherein subjects administered a single dosage exhibit a mean plasma oxycodone $AUC_{0\to\infty}$ of about 200 h·mg/L. In another aspect, the composition is provided in a dosage form containing a total amount of about 40 mg of oxycodone, wherein subjects administered a single dosage exhibit a mean plasma oxycodone $AUC_{0\to\infty}$ of about 400 h·mg/L. In another aspect, the composition is provided in a dosage form containing a total amount of about 80 mg of oxycodone, wherein subjects administered a single dosage exhibit a mean plasma oxycodone $AUC_{0\to\infty}$ of about 1000 h·mg/L.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibits a $T_{max}$ of about 1 hr to about 8 hrs, including each integer within the specified range. In one aspect, the composition is provided in a dosage form containing a total amount of about 10 mg to about 80 mg of oxycodone, wherein subjects administered a single dosage exhibit a $T_{max}$ of about 1 hr, about 1.5 hrs, about 2 hrs, about 2.5 hrs, about 3 hrs, about 3.5 hrs, about 4 hrs, 4.5 hrs, 5 hrs, 5.5 hrs, 6 hrs, 6.5 hrs, 7 hrs, 7.5 hrs, or about 8 hrs.

Another embodiment described herein is a method for treating an individual having pain, with a pharmaceutical composition described herein comprising an abuse deterrent matrix described herein comprising a dosage of about 10 mg of opioid analgesic to about 80 mg of opioid analgesic, wherein subjects administered a single dosage exhibit a mean plasma opioid analgesic $C_{max}$ of about 10 ng/mL to about 120 ng/mL, including each integer within the specified range. In one aspect, the composition is provided in a dosage form containing a total amount of about 10 mg of an opioid analgesic, wherein subjects administered a single dosage exhibit a mean plasma opioid analgesic $C_{max}$ of about 20 ng/mL. In another aspect, the composition is provided in a dosage form containing a total amount of about 20 mg of opioid analgesic, wherein subjects administered a single dosage exhibit a mean plasma opioid analgesic $C_{max}$ of about 30 ng/mL. In another aspect, the composition is provided in a dosage form containing a total amount of about 30 mg of opioid analgesic, wherein subjects administered a single dosage exhibit a mean plasma opioid analgesic $C_{max}$ of about 40 ng/mL. In another aspect, the composition is provided in a dosage form containing a total amount of about 40 mg of opioid analgesic, wherein subjects administered a single dosage exhibit a mean plasma opioid analgesic $C_{max}$ of about 60 ng/mL. In another aspect, the composition is provided in a dosage form containing a total amount of about 80 mg of opioid analgesic, wherein subjects administered a single dosage exhibit a mean plasma opioid analgesic $C_{max}$ of about 120 ng/mL.

Another embodiment described herein is a method for treating an individual having pain, with a pharmaceutical composition described herein comprising an abuse deterrent matrix described herein comprising a dosage of about 10 mg of opioid analgesic to about 80 mg of opioid analgesic, wherein subjects administered a single dosage exhibit a mean plasma opioid analgesic $AUC_{0\to\infty}$ of about 100 h·mg/L to about 1600 h·mg/L, including each integer within the specified range. In one aspect, the composition is provided in a dosage form containing a total amount of about 10 mg of an opioid analgesic, wherein subjects administered a single dosage exhibit a mean plasma opioid analgesic $AUC_{0\to\infty}$ of about 150 h·mg/L. In another aspect, the composition is provided in a dosage form containing a total amount of about 20 mg of opioid analgesic, wherein subjects administered a single dosage exhibit a mean plasma opioid analgesic $AUC_{0\to\infty}$ of about 400 h·mg/L. In another aspect, the composition is provided in a dosage form containing a total amount of about 40 mg of opioid analgesic, wherein subjects administered a single dosage exhibit a mean plasma opioid analgesic $AUC_{0\to\infty}$ of about 850 h·mg/L. In another aspect, the composition is provided in a dosage form containing a total amount of about 80 mg of opioid analgesic, wherein subjects administered a single dosage exhibit a mean plasma opioid analgesic $AUC_{0\to\infty}$ of about 1600 h·mg/L.

Another embodiment described herein is a method for treating an individual having pain, with a pharmaceutical composition described herein comprising an abuse deterrent matrix described herein comprising a dosage of about 10 mg of opioid analgesic to about 80 mg of opioid analgesic, wherein subjects administered a single dosage exhibits a $T_{max}$ of about 3 hrs to about 8 hrs, including each integer within the specified range. In one aspect, the composition is provided in a dosage form containing a total amount of about 10 mg to about 80 mg of opioid analgesic, wherein subjects administered a single dosage exhibit a $T_{max}$ of about 3 hrs, about 4 hrs, about 5 hrs, about 6 hrs, about 7 hrs, or about 8 hrs.

In another embodiment, the pharmaceutical compositions described herein further comprise one or more active pharmaceutical ingredient(s) suitable for treating, ameliorating, or prophylactically treating a bowel dysfunction due to acute or chronic opioid use, often referred to as opioid induced bowel disfunction (OIBD). Symptoms of OIBD typically comprise constipation (e.g., opioid induced constipation; OIC), anorexia, nausea and vomiting, gastro-oesophageal reflux, delayed digestion, abdominal pain, flatulence, bloating, hard stools, incomplete evacuation or straining during bowel movements. Alternative or additional uses for the one or more active pharmaceutical ingredient(s) described herein may be to treat, reduce, inhibit, or prevent additional effects of acute or chronic opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of one or more active pharmaceutical ingredient(s) include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases, terminally ill patients receiving opioid therapy such as an AIDS patient, a cancer patient, a cardiovascular patient;

subjects receiving opioid therapy for maintenance of opioid withdrawal. In one aspect, the subject is a subject using an opioid for chronic pain management. In another aspect, the subject is a subject using an acutely using an opioid for temporary pain management. In another aspect, the subject is a terminally ill patient. In another aspect, the subject is a person receiving opioid withdrawal maintenance therapy.

In another embodiment, suitable active pharmaceutical ingredients for treating a symptom or condition of opioid use comprise one or more active pharmaceutical ingredients for the treatment, amelioration, or prophylaxis of OIBD or OIC referred to herein as an anti-OIC agent. In some aspects, the anti-OIC agent comprises a peripherally acting mu-opioid receptor antagonist (PAMORA). In some aspects, the PAMORA comprises methylnaltrexone, naltrexone, naloxone, naloxegol, naldemadine, axelopran, or alvimopan, or a mixture or combination thereof.

In another embodiment, suitable active pharmaceutical ingredients that function as an anti-OIC agent does not function as a PAMORA. Exemplary and non-limiting additional non-PAMORA anti-OIC agents comprise a CLC-2 chloride channel agonist, such as lubiprostone; a non-selective opioid antagonist, such as levallorphan (naloxiphan), etorphine, dihydroetorphine, or diprenorphine; a mixed agonist/antagonist, such as cyclazocine, nalorphine, or nalmexone; a guanylate cyclase agonist, such as linaclotide; or a laxative, such as docusate, magnesium citrate, or senna.

It is understood that activation of mu-opiod receptors along the gastro intestinal tract are responsible for decreased bowel function and constipation. Thus, without being bound by any theory, PAMORAs and other opioid receptor antagonists described herein are useful for preventing symptoms of OIBD, and specifically OIC, by inhibiting the action of the mu-opioid receptor peripherally along the gastro-intestinal tract without inhibiting the mu-opiod receptors of the central nervous system (CNS). Therefore, a combination of an opioid agonist (e.g., oxycodone or other opioid analgesic) activates the CNS receptors and the co-administration of a PAMORA or other opioid antagonist inhibits the peripheral gut mu-opioid receptors, which are believed to be responsible for the incurrence of OIC.

It is further understood that alternative non-opioid antagonists, such as linaclotide and lubiprostone also prevent OIC symptoms. For example, lubiprostone is known to activate the ClC-2 chloride channels. This activation results in chloride-rich secretions, which soften stool and increase bowel motility resulting in bowel movements. In addition, the guanylate cyclase agonist linaclotide is thought to activate clonic motor neurons, which results in the promotion of bowel movements. Therefore, a combination of an opioid agonist (e.g., oxycodone or other opioid analgesic) activates the CNS receptors and the co-administration of a non-opioid antagonist anti-OIC agent or laxative prevents OIC by promoting bowel movements.

In one embodiment, the pharmaceutical composition described herein comprises a dose of an anti-OIC agent and a dose of an opioid (e.g., oxycodone or other opioid analgesic). In one aspect, the dose of an anti-OIC agent ranges from about 50 mg to about 600 mg and the dose of the opioid is from about 5 mg to about 150 mg, including every integer within the specified ranges. In another aspect, the dose of an anti-OIC agent ranges from about 50 mg to about 550 mg and the dose of the opioid is from about 5 mg to about 150 mg, including every integer within the specified ranges. In another aspect, the dose of an anti-OIC agent ranges from about 5 mg to about 50 mg and the dose of the opioid is from about 5 mg to about 100 mg, including every integer within the specified ranges.

In another embodiment, the weight percentage ratio range of an anti-OIC agent to opioid (e.g., oxycodone or other opioid analgesic) in the pharmaceutical composition described herein ranges from about 15:1 to about 1:18, including each ratio within the specified range. In one aspect, the weight percentage ratio range of an anti-OIC agent to opioid is from about 13:1 to about 1:1, including each ratio within the specified range. In another aspect, the weight percentage ratio range of an anti-OIC agent to opioid is from about 1:16 to about 1:1, including each ratio within the specified range. In another aspect, the weight percentage ratio range of an anti-OIC agent to opioid is about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1.

In one embodiment, the pharmaceutical compositions described herein comprise a dose of an opioid (e.g., oxycodone or other opioid analgesic) and a dose of a PAMORA. In one aspect, the pharmaceutical compositions described herein comprise a dose of an opioid and a dose of a PAMORA comprising naloxone or a pharmaceutically acceptable salt form thereof. In one aspect, the pharmaceutical compositions described herein comprise a dose of an opioid and a dose of a PAMORA comprising naltrexone or a pharmaceutically acceptable salt form thereof. In another aspect, the pharmaceutical compositions described herein comprise a dose of an opioid and a dose of a PAMORA comprising methylnaltrexone or a pharmaceutically acceptable salt form thereof. In another aspect, the pharmaceutical compositions described herein comprise a dose of an opioid and a dose of a PAMORA comprising naloxegol or a pharmaceutically acceptable salt form thereof.

In one embodiment, the pharmaceutical composition described herein comprises a dose of naloxone and a dose of an opioid comprising oxycodone or other opioid analgesic as described herein. In one aspect, the dose of the naloxone ranges from about 2.5 mg to about 100 mg, including each integer within the specified range. In another aspect, the dose of naloxone ranges from about 2.5 mg to about 50 mg, including each integer within the specified range. In another aspect, the dose of naloxone ranges from about 10 mg to about 50 mg, including each integer within the specified range. In another aspect, the dose of naloxone ranges from about 20 mg to about 40 mg, including each integer within the specified range. In another aspect, the dose of naloxone is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxone to opioid comprising oxycodone or other opioid analgesic in the pharmaceutical composition described herein ranges from about 1:10 to about 5:1, including all iterations of ratios within the specified range. In one aspect, the weight percentage ratio range of naloxone to opioid comprising hydrocodone or oxycodone is from about 1:5 to about 1:1, including all iterations of ratios within the specified range. In another aspect, the weight percentage ratio range of naloxone to opioid comprising oxycodone or other opioid analgesic is from about 1:4 to about 1:2, including all iterations of ratios within the specified range. In another aspect, the weight percentage ratio range of naloxone to opioid comprising oxycodone or other opioid analgesic is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxone to opioid comprising oxycodone or other opioid analgesic is about 1:2.

In another embodiment, the pharmaceutical composition described herein comprises a dose of about 5 mg of naloxone and a dose of about 10 mg of oxycodone. In another embodiment, the pharmaceutical composition described herein comprises a dose of about 10 mg of naloxone and a dose of about 20 mg of oxycodone. In another embodiment, the pharmaceutical composition described herein comprises a dose of about 20 mg of naloxone and a dose of about 40 mg of oxycodone. In another embodiment, the pharmaceutical composition described herein comprises a dose of about 40 mg of naloxone and a dose of about 80 mg of oxycodone. In another embodiment, the pharmaceutical composition described herein comprises a dose of about 80 mg of naloxone and a dose of about 160 mg of oxycodone.

In another embodiment, the pharmaceutical composition described herein comprises a dose of about 5 mg of naloxone and a dose of about 10 mg of opioid analgesic. In another embodiment, the pharmaceutical composition described herein comprises a dose of about 10 mg of naloxone and a dose of about 20 mg of opioid analgesic. In another embodiment, the pharmaceutical composition described herein comprises a dose of about 20 mg of naloxone and a dose of about 40 mg of opioid analgesic. In another embodiment, the pharmaceutical composition described herein comprises a dose of about 40 mg of naloxone and a dose of about 80 mg of opioid analgesic. In another embodiment, the pharmaceutical composition described herein comprises a dose of about 80 mg of naloxone and a dose of about 160 mg of opioid analgesic.

In another embodiment, the pharmaceutical composition described herein comprises a dose of about 40 mg of oxycodone and a dose of about 20 mg of naloxone. In one aspect, the composition is provided in a dosage form containing a total amount of about 40 mg of an oxycodone and about 20 mg of naloxone, wherein subjects administered a single dosage exhibit a mean plasma oxycodone $AUC_{0 \to \infty}$ of about 400 h·mg/L to about 600 h·mg/L and a mean plasma naloxone $AUC_{0 \to \infty}$ of about 500 h·mg/L to about 600 h·mg/L. In another aspect, the composition is provided in a dosage form containing a total amount of about 40 mg of oxycodone and about 20 mg of naloxone, wherein subjects administered a single dosage exhibit a mean plasma oxycodone $C_{max}$ of about 30 ng/mL to about 50 ng/mL and a mean plasma naloxone $C_{max}$ of about 50 ng/mL to about 70 ng/mL. In another aspect, the composition is provided in a dosage form containing a total amount of about 40 mg of oxycodone and about 20 mg of naloxone, wherein subjects administered a single dosage exhibit an oxycodone $T_{max}$ of about 1 hr to about 5 hrs and a naloxone $T_{max}$ of about 0.5 hr to about 3 hrs.

In one embodiment, the pharmaceutical composition described herein comprises a dose of methylnaltrexone or naltrexone and a dose of an opioid comprising opioid analgesic or oxycodone as described herein. In one aspect, the dose of the methylnaltrexone or naltrexone ranges from about 2.5 mg to about 100 mg, including each integer within the specified range. In another aspect, the dose of methylnaltrexone or naltrexone ranges from about 50 mg to about 600 mg, including each integer within the specified range. In another aspect, the dose of methylnaltrexone or naltrexone ranges from about 100 mg to about 600 mg, including each integer within the specified range. In another aspect, the dose of methylnaltrexone or naltrexone ranges from about 300 mg to about 600 mg, including each integer within the specified range. In another aspect, the dose of methylnaltrexone or naltrexone ranges from about 400 mg to about 600 mg, including each integer within the specified range. In another aspect, the dose of methylnaltrexone or naltrexone is about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, or about 550 mg.

In another embodiment, the weight percentage ratio range of methylnaltrexone or naltrexone to opioid comprising opioid analgesic or oxycodone in the pharmaceutical composition described herein ranges from about 13:1 to about 1:1, including all iterations of ratios within the specified range. In one aspect, the weight percentage ratio range of methylnaltrexone or naltrexone to opioid comprising opioid analgesic or oxycodone is from about 10:1 to about 1:1, including all iterations of ratios within the specified range. In another aspect, the weight percentage ratio range of methylnaltrexone or naltrexone to opioid comprising opioid analgesic or oxycodone is from about 5:1 to about 1:1, including all iterations of ratios within the specified range. In another aspect, the weight percentage ratio range of methylnaltrexone or naltrexone to opioid comprising opioid analgesic or oxycodone is about 1:1, about 2:1, about 3:1, about 4:1, about 5:1, about 6:1, about 7:1, about 8:1, about 9:1, about 10:1, about 11:1, about 12:1, or about 13:1.

In one embodiment, the pharmaceutical composition described herein comprises a dose of naloxegol and a dose of an opioid comprising oxycodone or other opioid analgesic as described herein. In one aspect, the dose of the naloxegol ranges from about 2.5 mg to about 100 mg, including each integer within the specified range. In another aspect, the dose of naloxegol ranges from about 2.5 mg to about 50 mg, including each integer within the specified range. In another aspect, the dose of naloxegol ranges from about 10 mg to about 50 mg, including each integer within the specified range. In another aspect, the dose of naloxegol ranges from about 20 mg to about 40 mg, including each integer within the specified range. In another aspect, the dose of naloxegol is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxegol to opioid comprising oxycodone or other opioid analgesic in the pharmaceutical composition described herein ranges from about 1:10 to about 5:1, including all iterations of ratios within the specified range. In one aspect, the weight percentage ratio range of naloxegol to opioid comprising oxycodone or other opioid analgesic is from about 1:5 to about 1:1, including all iterations of ratios within the specified range. In another aspect, the weight percentage ratio range of naloxegol to opioid comprising oxycodone or other opioid analgesic is from about 1:4 to about 1:2, including all iterations of ratios within the specified range. In another aspect, the weight percentage ratio range of naloxegol to opioid comprising oxycodone or other opioid analgesic is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxegol to opioid comprising oxycodone or other opioid analgesic e is about 1:2.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, opioid use, such as, for example, opioid induced bowel dysfunction, opioid induced constipation, gastrointestinal dysfunction (e.g., inhibition of intestinal motility, constipation, GI sphincter constriction), nausea, emesis (vomiting), biliary spasm, colic, dysphoria, pruritus, urinary retention, depression of respiration, papillary constriction, cardiovascular effects, chest wall rigidity and cough suppression, depression of stress response, and immune suppression associated with use of narcotic analgesia, etc., or combinations thereof.

Another embodiment described herein is a method for treating, retarding the progression of, prophylaxis of, delaying the onset of, ameliorating, or reducing the symptoms of, irritable bowel syndrome, colitis, post-operative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (colectomy, e.g., right hemicolectomy, left hemicolectomy, transverse hemicolectomy, colectomy takedown, low anterior resection), and delayed absorption of orally administered medications or nutritive substances comprising the administration of a therapeutically effective amount of one or more abuse deterrent pharmaceutical compositions described herein.

Another embodiment described herein is a method for improving the quality of life of subjects receiving opioids, as well as to reduce complications arising from chronic constipation, such as hemorrhoids, appetite suppression, mucosal breakdown, sepsis, colon cancer risk, and myocardial infarction comprising the administration of a therapeutically effective amount of one or more abuse deterrent pharmaceutical compositions described herein.

In another embodiment, the pharmaceutical composition described herein provides a dosage form comprising an opioid and a PAMORA as described in, which in terms of efficacy, is ranked good or very good by more than 50% of patients, 60%, 70%, 80%, 90%, or more of patients. In aspect, the dosage form is provided which comprises an opioid and a PAMORA as described in, which in terms of tolerability, is ranked good or very good by more than 50% of patients, 60%, 70%, 80%, 90%, or more of patients.

In another embodiment, the pharmaceutical composition described herein provides a dosage form comprising an opioid and a PAMORA as described in, which provides a reduction of days with laxative intake by at least 10%, 20%, 30%, 40%, 50%, 60%, 70%, 80%, or even 90%. In one aspect, the dosage form completely reduces the need for any laxatives to be taken independently.

In some embodiments, bowel function is assessed by observing parameters that are associated with bowel function. In particular, bowel function may be determined based on parameters selected from ease or difficulty of defecation, feeling of incomplete bowel evacuation, and/or personal judgment of patient regarding constipation. Other parameters which may be observed alternatively or in addition in order to assess the bowel function of a patient include among other things stool frequency, stool consistency, cramping, and painful laxation. In addition, the measurement of spontaneous bowel movements indicates improved bowel function.

Bowel function may be assessed by measuring parameters, which are associated with bowel function using numerical analog scales (NAS) for these parameters because this may provide more accurate results. This approach is particularly advantageous when assessing the bowel function in patients receiving treatment with analgesics, because analgesic efficacy of drugs is usually assessed using a numeric analog scale.

In one embodiment, a reduction in OIC is assessed by measuring a change in the spontaneous bowel movements (SBMs) frequency rate (e.g., SBMs/week). Patients are typically classified as having OIC when having less than 3 SBMs per week for about 4 weeks while taking an opioid. A positive response to an OIC agent is assessed as an increase in SBMs over a period of time following the administration of the OIC agent.

In another embodiment a reduction in OIC by an anti-OIC agent is assessed by measuring the time to first SBM following administration of the anti-OIC agent compared to a placebo agent.

In another embodiment, a reduction in OIC by an anti-OIC agent is assessed by measuring a change in stool consistency from baseline over a period of time. For example, the Bristol Stool Scale may be used to assess changes.

In some embodiments, the pharmaceutical compositions comprising an opioid and an anti-OIC agent as described herein provides improvement of the bowel function characterized by an increase of the mean bowel function score of at least 5, at least about 8, at least about 10 or at least about 15 after administration at steady state or of a single dose to human patients or healthy human subjects, wherein the mean bowel function score is measured with a numerical analog scale ranging from 0 to 100.

In one embodiment, the bowel function is assessed by the bowel function index (BFI), which is measured in patients. The mean bowel function score may be determined by a method for assessing bowel function in a patient comprising the steps of: providing the patient with a numeric analog scale for at least one parameter, which parameter is associated with bowel function; causing the patient to indicate on the numeric analog scale the amount and/or intensity of the parameter being experienced; and observing the amount and/or intensity of the at least one parameter indicated on the numeric analog scale in order to assess bowel function. In one aspect the patient indicates the amount and/or intensity of parameter being experienced during the last days or weeks, e.g. during the last 1, 2, 3, 4, 5, 6, 7, 10, or 14 days. In another aspect, the numerical analog scale on which the patient indicates his/her subjective experience of the observed parameter may have any size or form and may range from 0 or any other number to any number, such as from 0 to 10 or from 0 to 50 or from 0 to 300 or from 1 to 10.

In another embodiment, if more than one parameter is observed, a mean bowel function may be obtained in form of a numerical value. This numerical value is the mean of the parameters observed, e.g., the three numeric analog scale values for ease or difficulty of defecation, feeling of incomplete bowel evacuation and judgment of constipation. The parameters, which are measures of bowel function or which are associated with bowel function, may comprise opioid induced bowel dysfunctions (OIBD or OIC) as described herein.

In another embodiment, bowel function may be determined based on the following parameters: ease or difficulty of defecation, for example during the last 7 days according to the patient assessment, wherein 0 corresponds to no difficulties and 100 corresponds to severe difficulties; feeling of incomplete bowel evacuation, for example during the last 7 days according to the patient assessment, wherein 0 corresponds to no feeling of incomplete bowel evacuation and 100 corresponds to very strong feeling of incomplete bowel evacuation; personal judgment of patient regarding constipation, for example during the last 7 days, wherein 0 corresponds to no constipation at all and 100 corresponds to very heavy constipation.

In another embodiment, bowel function may be assessed with analogs scales as described in U.S. Pat. No. 6,258,042 and International Patent Application Publication No. WO 2003/073937, which may be adapted to devices or analog scales as described above as would be understood by one of ordinary skill in the art. The disclosures of these two references are hereby incorporated by reference for such teachings.

In another embodiment, the pharmaceutical compositions described herein further comprise one or more active pharmaceutical ingredient(s) comprising a PAMORA may also further limit or prevent drug abuse by inhibiting the action or effects of an opioid. The PAMORAs described herein, for example, methylnaltrexone, naltrexone, naloxone, naloxegol, or alvimopan can function to have an aversive effect. This aversive affect may include any unpleasant side effect comprising inducing opioid withdrawl symptoms, diarrhea, nausea, reduced euphoria or a mixture or combination thereof.

In another embodiment, the abuse deterrent pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Abuse deterrent matrices as described herein were prepared using the composition shown in Tables 6-10. The compositions were prepared according to the method of Example 2 and encapsulated in a hard capsule shell. Other suitable non-limiting capsule shells for the abuse deterrent matrices described herein comprise a soft capsule shell, enteric soft capsule shell, and an enteric hard capsule shell.

TABLE 6

Abuse Deterrent Controlled Release Matrix Compositions

| Ingredient | Weight Percentage (%) | | |
|---|---|---|---|
| | F1 | F2 | F3 |
| Capmul ® MCM | 59 | 60 | 60 |
| Polyethylene oxide (WSR 301) | 30 | 30 | 0 |
| Polyethylene oxide (WSR 303) | 0 | 0 | 30 |
| Carbopol 974P | 1 | 0 | 0 |
| Oxycodon HCl | 10 | 10 | 10 |
| TOTAL | 100% | 100% | 100% |

TABLE 7

Abuse Deterrent Controlled Release Matrix Compositions

| Ingredient | Weight Percentage (%) | | |
|---|---|---|---|
| | F4 | F5 | F6 |
| Polyethylene glycol 600 | 60 | 57.6 | 60 |
| Polyethylene glycol 1000 | 8 | 7.6 | 8 |
| Polyvinylpyrrolidone K90 | 1 | 1 | 1 |
| Methocel ™ K100M | — | — | 10.7 |
| Carbopol 974P | 1 | 5 | 1 |
| Polyethylene oxide (WSR 301) | 10.7 | 9.6 | — |
| Polyethylene oxide (WSR 303) | 10.7 | 9.6 | 10.7 |
| Oxycodone HCl | 9 | 8.6 | 9 |
| TOTAL | 100% | 100% | 100% |

TABLE 8

Abuse Deterrent Controlled Release Matrix Compositions

| Ingredient | Weight Percentage (%) F7 |
|---|---|
| Capmul ® MCM | 63.4 |
| Polyethylene oxide (WSR 301) | 27 |
| Polyvinylpyrrolidone K90 | 1.25 |
| BHA | 0.25 |
| BHT | 0.10 |
| Oxycodone HCl | 8 |
| TOTAL | 100% |

TABLE 9

Abuse Deterrent Controlled Release Matrix Compositions

| Ingredient | Weight Percentage (%) F8 |
|---|---|
| Oleic Acid | 60.7 |
| Ethocel ™ 20cP | 1 |
| Polyethylene oxide (WSR 301) | 30 |
| BHA | 0.25 |
| BHT | 0.10 |
| Oxycodone HCl | 8 |
| TOTAL | 100% |

TABLE 10

Abuse Deterrent Controlled Release Matrix Compositions

| Ingredient | Weight Percentage (%) F9 |
|---|---|
| Maisine ™ 35-1 | 60.7 |
| Polyethylene oxide (WSR 301) | 30 |
| BHA | 0.25 |
| BHT | 0.10 |
| Oxycodone HCl | 9 |
| TOTAL | 100% |

TABLE 11

Abuse Deterrent Controlled Release Matrix Compositions

| Ingredient | Weight (grams) | Weight Percentage (%) F10 |
|---|---|---|
| Oleic Acid | 15.5 | 62 |
| Ethocel ™ 20 cP | 0.25 | 1 |
| Polyethylene oxide (301 FP) | 7.5 | 30 |
| BHA | 0.05 | 0.2 |
| BHT | 0.02 | 0.9 |
| Sodium lauryl sulfate | 1.25 | 5 |
| Hydrocodone bitartrate | 0.42 | 1.7 |
| TOTAL | 25 | 100% |

TABLE 12

Abuse Deterrent Controlled Release Matrix Compositions

| Ingredient | Weight Percentage (%) F11 |
|---|---|
| Soybean Oil | 55.7 |
| Ethocel ™ 20 cP | 20 |
| Polyethylene Glycol | 20 |
| BHA | 0.25 |
| BHT | 0.10 |
| HPMC K100M | 15 |
| Oxycodone HCl | 8 |
| TOTAL | 100% |

Example 2

Abuse deterrent controlled release matrix compositions as described herein comprise one or more flowability enhancers, one or more release modifiers, optionally one or more viscosity modifiers, optionally one or more antioxidants, and one or more active pharmaceutical ingredients. Flowability enhancers comprise any one or more of a medium chain mono- and di-glyceride (e.g., Capmul® MCM), oleic acid, or glyceryl monolinoleate (e.g., Maisine™ 35-1); the one or more release modifiers comprises a high molecular weight polyethylene oxide (e.g., POLYOX™ WSR 301 or POLYOX™ WSR 303) and optionally a carboxyvinyl polymer (e.g., Carbopol® 974P); the optional one or more viscosity modifiers comprises a polyvinylpyrrolidone (e.g., polyvinylpyrrolidone K90) or an ethylcellulose polymer (e.g., Ethocel™ 20 cP); the optional one or more antioxidants comprises BHA or BHT, and the one or more active pharmaceutical ingredients comprises oxycodone or other opioid analgesic.

Abuse deterrent controlled release matrices according to compositions F1-F3 of Table 6 were prepared by suspending the specified amount of Carbopol™ 974P and POLYOX™ WSR 301 or POLYOX™ WSR 303 in the specified amount of Capmul® MCM to form a suspension mixture. Next, the specified amount of oxycodone was added to the mixture and thoroughly mixed to form a final matrix fill mixture and this mixture was filled into soft capsule shells. The filled capsules were then annealed at 70° C. for about one hour.

The abuse deterrent controlled release matrix according to composition F7 of Table 8 was prepared by heating the specified amount of Capmul® MCM to 55° C. The specified amount of polyvinylpyrrolidone K90 was mixed in the heated Capmul® MCM until completely dissolved. Next BHA and BHT were added until completely dissolved. The resulting mixture was cooled to approximately 30° C. and the specified amount of the active pharmaceutical ingredient oxycodone HCl was added and mixed until uniformly dispersed. Next the polyethylene oxide 301 was added and mixed uniformly to form a suspension mixture. The resulting liquid mixture was encapsulated as a liquid suspension and was dried and cured at a high temperature for 45±15 minutes at 70±2° C.

The abuse deterrent controlled release matrix according to composition F8 of Table 9 was prepared by heating the specified amount of oleic acid to 140° C. The specified amount of Ethocel™ 20 cP was mixed in the heated oleic acid until completely dissolved. This mixture was then cooled to about 85° C. and BHA and BHT was added until completely dissolved. The resulting mixture was cooled to approximately 30° C. and the specified amount of the active pharmaceutical ingredient oxycodone HCl and polyethylene oxide 301 was added and mixed until uniformly suspended in a dispersion. The resulting liquid mixture was encapsulated as a liquid suspension into soft gelatin capsules and was dried and cured for 45±15 minutes at 70±2° C.

The abuse deterrent controlled release matrix according to composition F9 of Table 10 was prepared by heating the specified amount of Maisine™ 35-1 to 65° C. BHA and BHT were added until completely dissolved. This mixture was then cooled to about 30° C. and the specified amount of the active pharmaceutical ingredient oxycodone HCl was added and mixed until uniformly dispersed. Next the specified amount of polyethylene oxide 301 was added and mixed uniformly to form a suspension mixture. The resulting liquid mixture was encapsulated as a liquid suspension into soft gelatin capsules and was dried and for 45±15 minutes at 70±2° C.

The abuse deterrent controlled release matrix according to composition F10 of Table 11 was prepared by heating the specified amount of oleic acid to 140° C. The specified amount of Ethocel™ 20 cP was mixed in the heated oleic acid until completely dissolved. This mixture was then cooled to about 85° C. and BHA and BHT was added until completely dissolved. The resulting mixture was cooled to approximately 30° C. and the specified amount of the active pharmaceutical ingredient hydrocodone bitartrate, sodium lauryl sulfate, and polyethylene oxide 301 was added and mixed until uniformly suspended in a dispersion. The resulting liquid mixture was encapsulated as a liquid suspension into soft gelatin capsules and was dried and cured for 45±15 minutes at 70±2° C.

The abuse deterrent matrices prior to encapsulation and annealing demonstrated a viscous yet flowable aspect. Following the annealing step at 70° C., the capsules demonstrated a semi-solid elastic aspect.

The process for manufacturing a soft capsule comprising the abuse deterrent matrices as described herein includes preparing a gel mass for a soft capsule; casting the gel mass into films or ribbons using heat-controlled drums or surfaces; and manufacturing a soft capsule comprising a matrix fill using rotary die technology. During this process, the abuse deterrent controlled release matrix is injected into the lumen as the soft capsule is formed by rotary die encapsulation. The soft capsule can be a typical soft capsule ("soft gel") or an enteric soft capsule.

Figure 8:
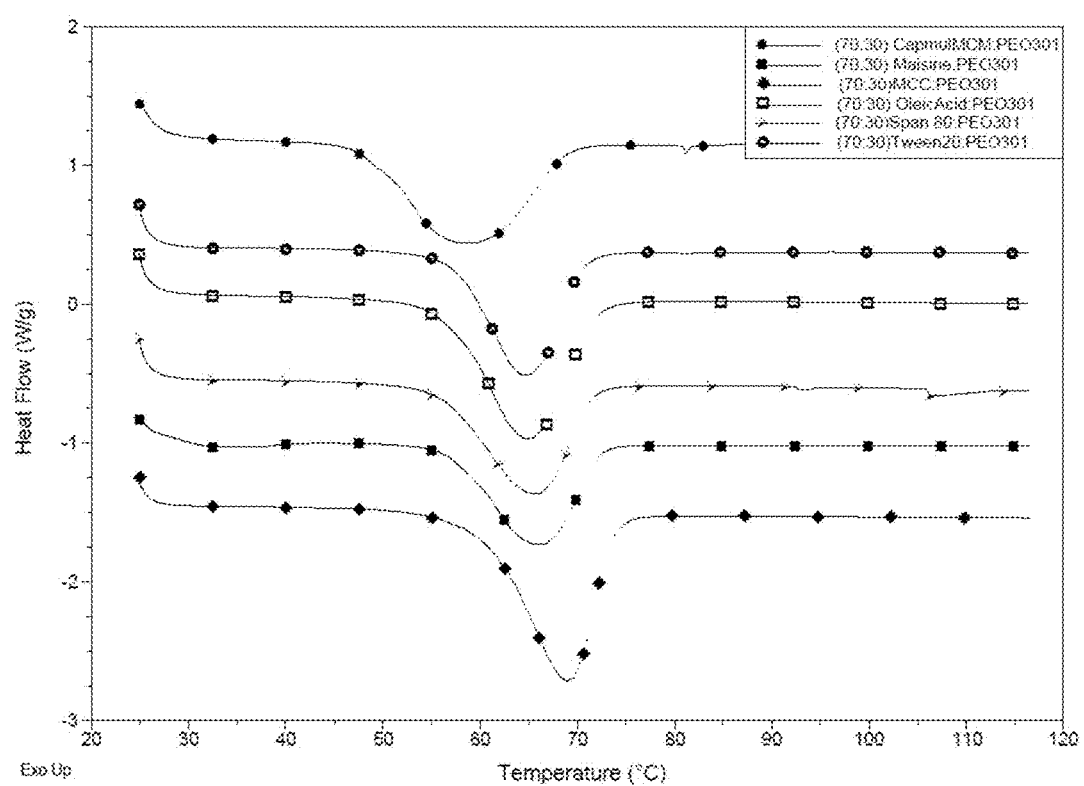
FIG. 8. Representative thermogram data demonstrating PEO melting point depression results in various flowability enhancers compared to a non-flowability enhancing excipient control.

The melting point of PEO in different flowability enhancers including medium chain mono- and di-glyceride (e.g., Capmul® MCM), oleic acid, or glyceryl monolinoleate (e.g., Maisine™ 35-1) was tested. It is hypothesized that the PEO release modifier is suspended and not dissolved within the flowability enhancer throughout the processing steps. During the annealing steps, however, the release modifier is believed to become molten at the two components may be miscible. When subsequently cooled, the release modifier subsequently recrystallizes and forms a semi-solid elastic matrix that encapsulates the flowability enhancer and an active pharmaceutical ingredient. To test this hypothesis, the various flowability enhancers used in the abuse deterrent matrix formulations of Tables 9-11 were tested. Thermograms show that PEO exhibits a surprising and significant melting point depression in the presence of Capmul, which impacts processability. Other flowability enhancers evaluated, including Maisine™ 35-1, oleic acid, Span® 80 and Tween® 20, also decreased the PEO melting point but to a lesser extent. An inert diluent powder, microcrystalline cellulose, was used as a control, which demonstrated no impact on the melting point (FIG. 8).

Example 4

The dissolution and release profiles under different dissolution conditions for pharmaceutical compositions comprising the test abuse deterrent matrix compositions described in Table 6 and Table 7 are shown in FIGS. 1-7.

The percent release of oxycodone from the abuse deterrent controlled release matrix compositions shown in Table 6, generated by the methods described herein and encapsulated in a hard shell capsule as described herein, were tested. As shown in FIG. 1, a test pharmaceutical composition comprising the abuse deterrent matrix according to F1 of Table 6 comprising oxycodone in an annealed capsule shell demonstrated a similar release rate of oxycodone compared to a reference oxycodone abuse deterrent pharmaceutical composition. The percent release of oxycodone was determined by measuring the amount of oxycodone released from the test and reference abuse deterrent compositions in fasted state simulated gastric fluid (FaSSGF) at pH 1.2 for two hours and in fasted state simulated intestinal fluid (FaSSIF) at pH 6.8 for ten hours according to USP specifications using Apparatus III at 30 dpm.

Figure 2:
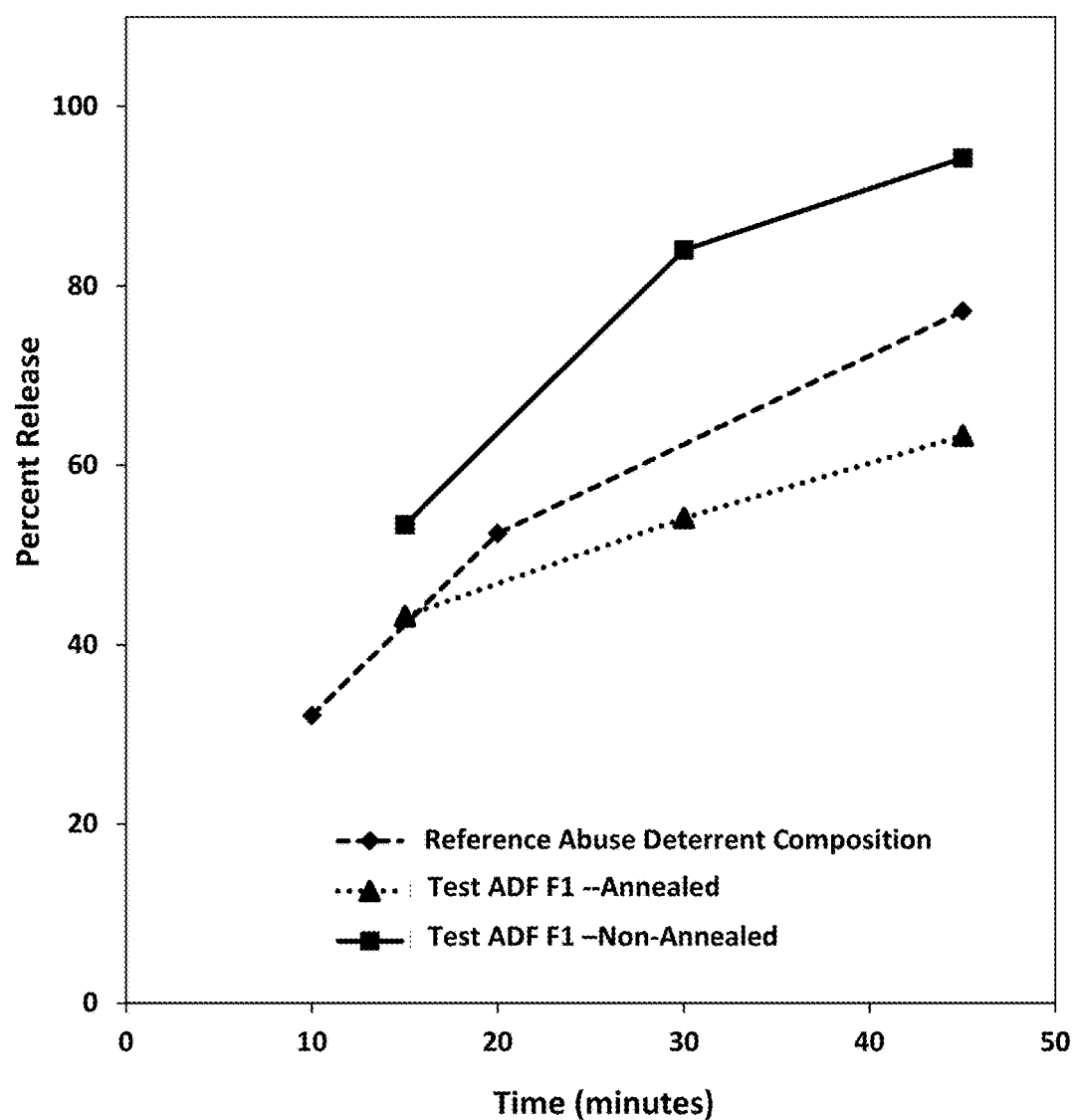
FIG. 2. Percent release of oxycodone from annealed and non-annealed test abuse deterrent pharmaceutical compositions (F1) compared to the percent release of oxycodone from a reference abuse deterrent pharmaceutical composition under aqueous boiling conditions.

Next, non-annealed and annealed pharmaceutical compositions generated by the annealing procedure described in Example 2 were tested. As shown in FIG. 2, the annealed test pharmaceutical composition comprising the abuse deterrent matrix according to F1 of Table 6 released less oxycodone under aqueous boiling conditions compared to a reference oxycodone abuse deterrent composition. However, the same composition (F1 of Table 6) that was not annealed demonstrated a higher release rate as compared to both the annealed test and reference abuse deterrent compositions. This result suggests that the annealing procedure listed in Example 2 may be one contributor to the abuse deterrent properties of the compositions described herein.

Figure 3:
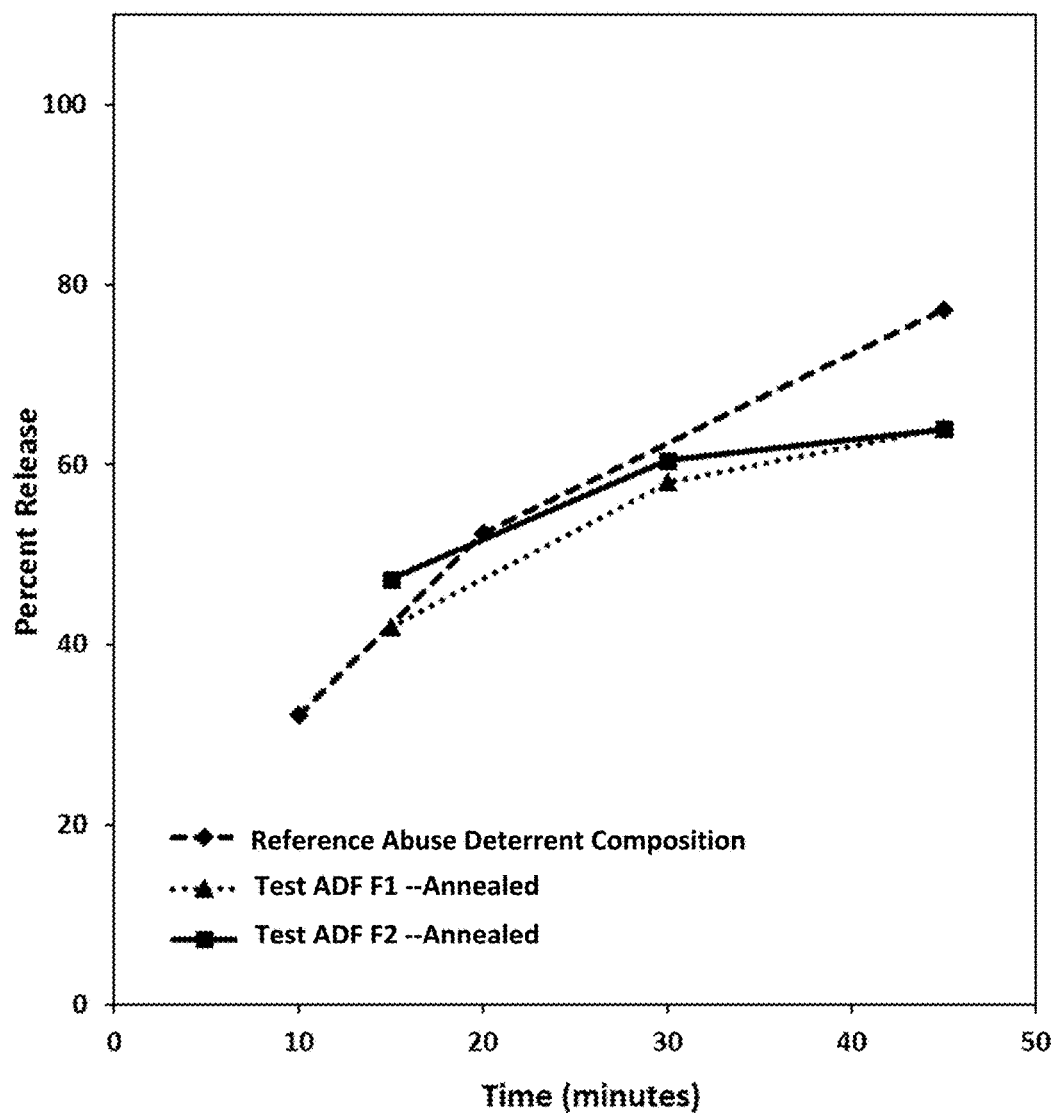
FIG. 3. Percent release of oxycodone from annealed test abuse deterrent pharmaceutical compositions (F1 and F2) with or without a viscosity modifier compared to the percent release of oxycodone from a reference abuse deterrent pharmaceutical composition under aqueous boiling conditions.

The effects of the viscosity modifier Carbopol® 974P on oxycodone percent release under boiling conditions were assessed. As shown in FIG. 3, the oxycodone percent release difference between the annealed test pharmaceutical composition comprising the abuse deterrent matrix according to F1 (1% Carbopol® 974P) and F2 (no Carbopol® 974P) of Table 6 was minimal.

Figure 4:
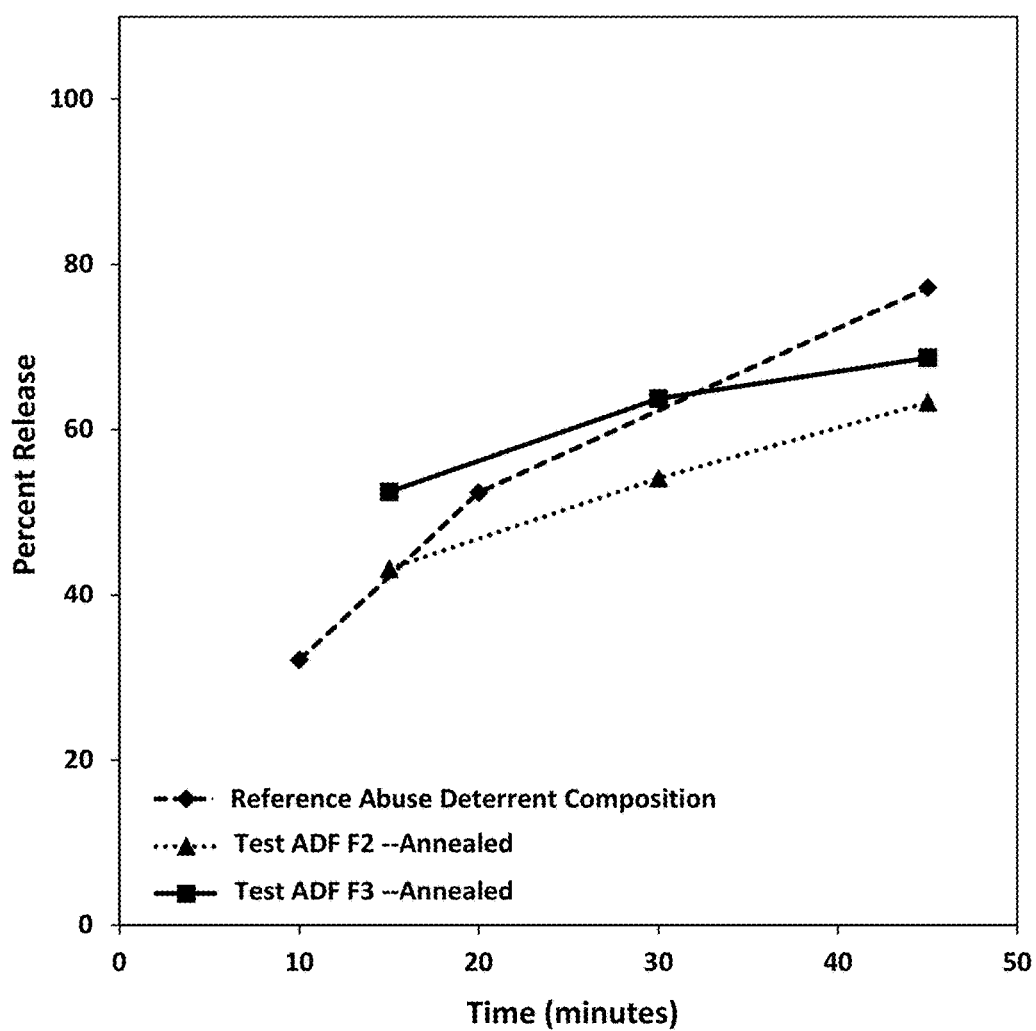
FIG. 4. Percent release of oxycodone from annealed test abuse deterrent pharmaceutical compositions (F2 and F3) having different molecular weight polyethylene oxide compared to the percent release of oxycodone from a reference abuse deterrent pharmaceutical composition under aqueous boiling conditions.

Next, the effects of different molecular weight polyethylene oxide in annealed test pharmaceutical compositions comprising the abuse deterrent matrices were tested for under boiling conditions. As shown in FIG. 4, the annealed test abuse deterrent composition having higher molecular weight polyethylene oxide according to F3 of Table 6 demonstrated a modestly higher percent release of oxycodone compared to the composition having lower molecular weight polyethylene oxide according to F2 of Table 6, but was still lower than the percent release in the reference abuse deterrent formulation after 40 minutes.

Figure 5:
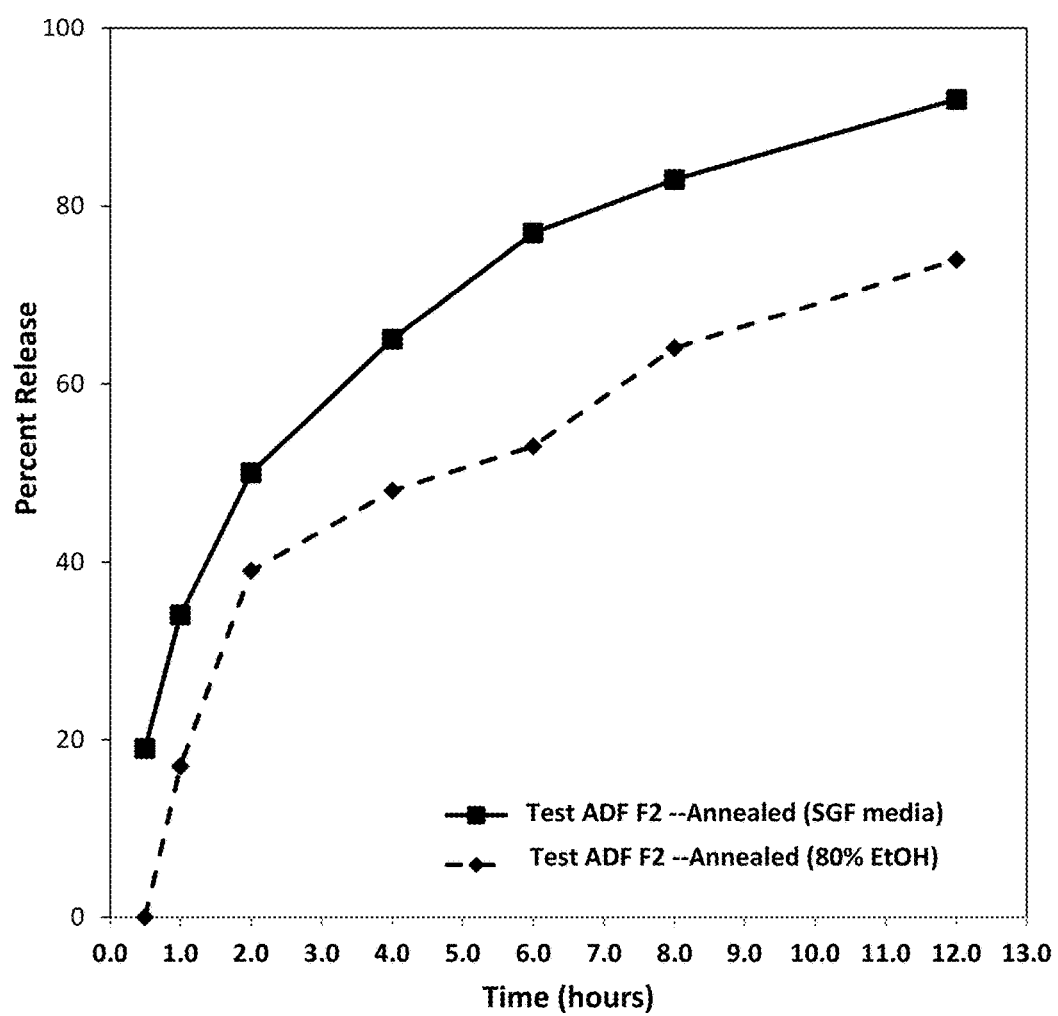
FIG. 5. Percent release of oxycodone from an annealed test abuse deterrent pharmaceutical composition (F2) in either SGF or an 80% ethanol solution.

Next, the dissolution of the annealed test pharmaceutical composition comprising the abuse deterrent matrix according to F2 of Table 6 was tested for oxycodone release in simulated gastric fluid or in an 80% ethanol solution. As shown in FIG. 5, this test abuse deterrent composition demonstrated a lower percent release in ethanol compared to the percent release in simulated gastric fluid (pH 1.2).

Figure 6:
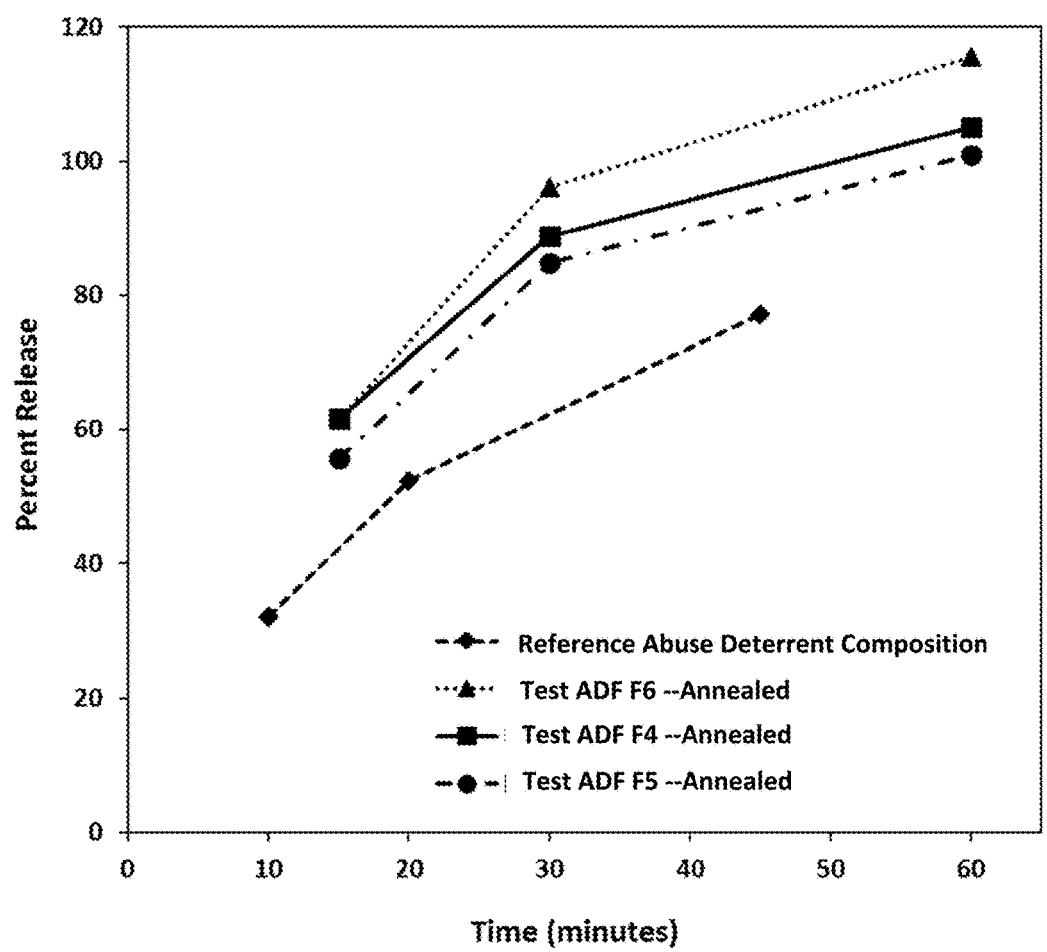
FIG. 6. Percent release of oxycodone from annealed test abuse deterrent pharmaceutical compositions (F4-F6) in aqueous conditions at 80° C. compared to a reference oxycodone abuse deterrent composition.

The percent release of oxycodone from the abuse deterrent controlled release matrix compositions shown in Table 7 encapsulated in a soft gel capsule were tested in aqueous conditions at 80° C. These matrix compositions all had reduced polyethylene oxide percentages compared to the matrix compositions of Table 6 and demonstrated a higher percent release of oxycodone compared to the tested reference abuse deterrent composition (FIG. 6). This result indicates that higher levels of polyethylene oxide (e.g., 25%-30%) may also contribute to the abuse deterrent characteristics in boiling or near boiling conditions.

Figure 7:
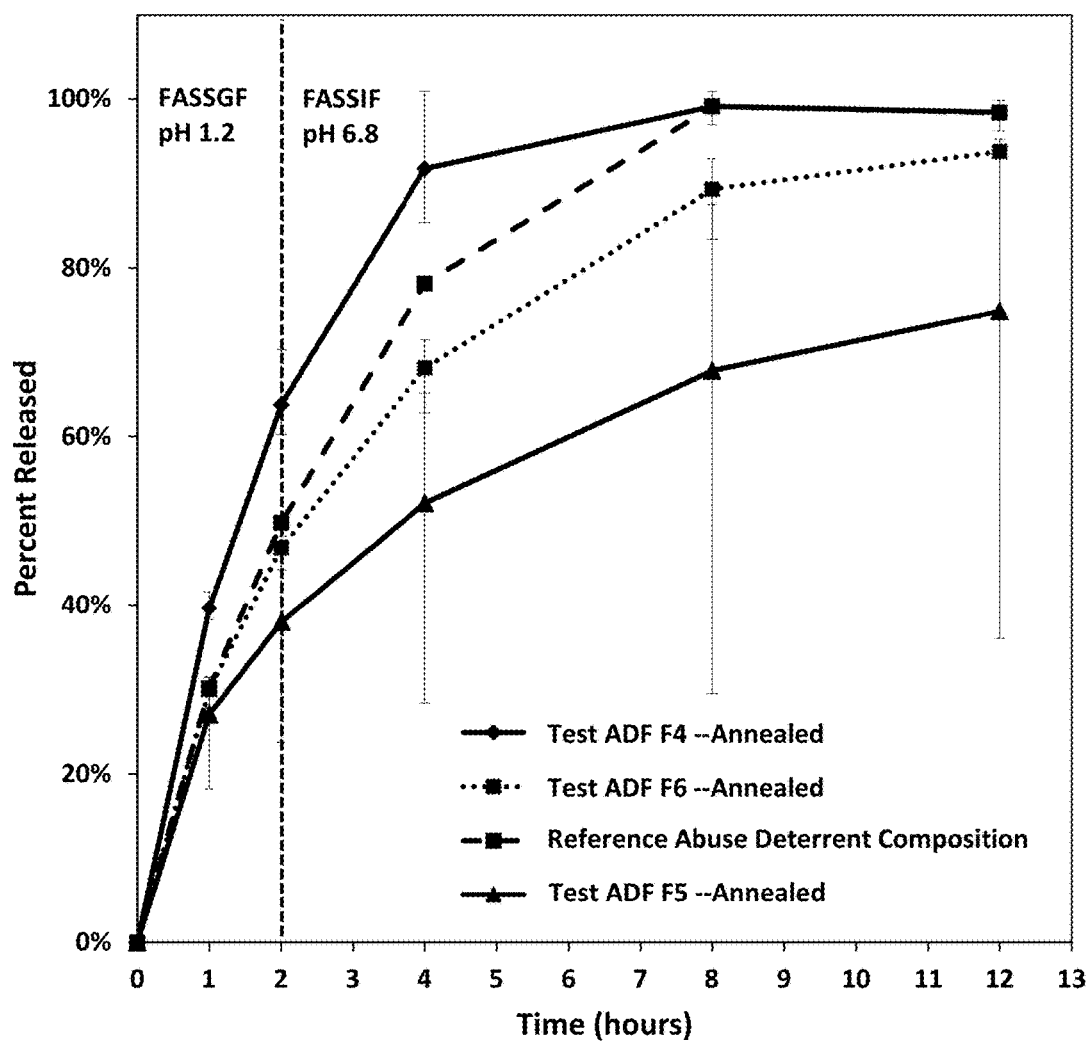
FIG. 7. Percent release of oxycodone from annealed test abuse deterrent pharmaceutical compositions (F4-F6) compared to the percent release of oxycodone from a reference abuse deterrent pharmaceutical composition in FASSGF and FASSIF buffer.

Next, the percent release of oxycodone from the reference abuse deterrent composition and the compositions F4-F6 of Table 7 were determined by conducting a dissolution test in FaSSGF at pH 1.2 for two hours and FaSSIF at pH 6.8 for ten hours according to USP specifications using Apparatus III at 30 dpm (FIG. 7).

Example 5

Figure 9:
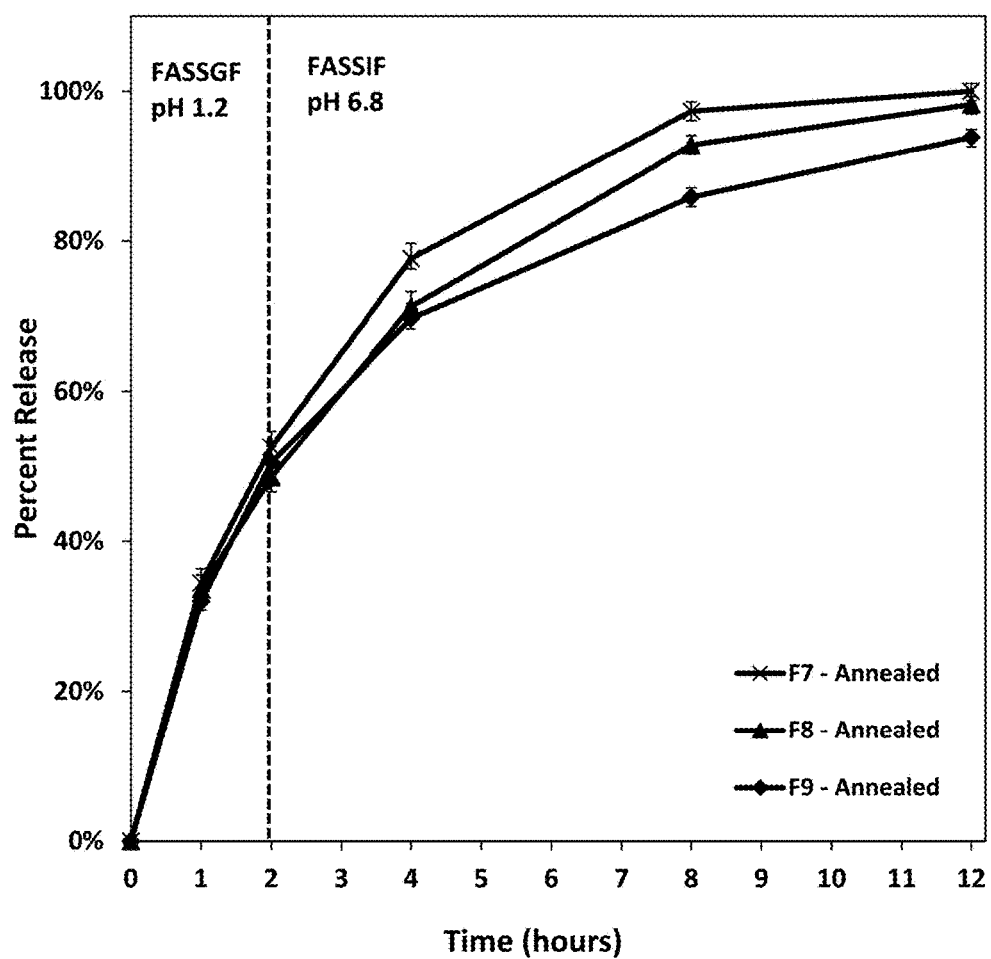
FIG. 9. Percent release of oxycodone from annealed test abuse deterrent pharmaceutical compositions (F7-F9) compared in FaSSGF and FaSSIF buffer.

The dissolution and release profiles under different dissolution conditions for pharmaceutical compositions comprising the test abuse deterrent matrix compositions described in Tables 8-10 corresponding to F7-F9 compared to a reference abuse deterrent matrix are shown in Table 13 below and in FIG. 9. The release profiles during conditions of non-abuse demonstrated a low variability between each of the compositions. The dissolution of these abuse deterrent matrices were determined by conducting a dissolution test in FaSSGF at pH 1.2 for two hours and FaSSIF at pH 6.8 for ten hours according to USP specifications using Apparatus III at 30 dpm.

TABLE 13

Dissolution % of API from Abuse Deterrent Matrix F7-F9

| Time (hr) | % Release Ref | % Release F7 | % Release F8 | % Release F9 |
|---|---|---|---|---|
| 1 | 34 | 34 | 30 | 34 |
| 2 | 55 | 53 | 50 | 49 |
| 4 | 83 | 78 | 70 | 71 |
| 8 | 99 | 97 | 85 | 93 |
| 12 | 100 | 100 | 93 | 100 |

Figure 10:
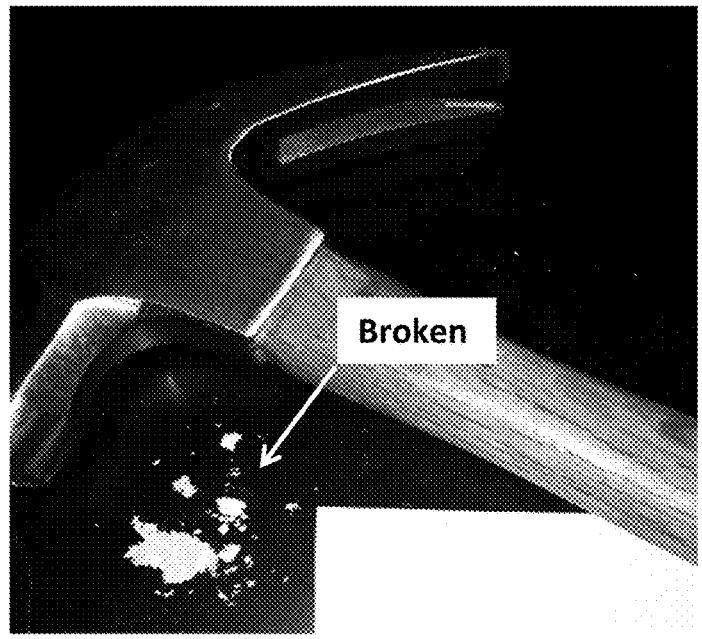
FIG. 10. Representative image of (A) a reference abuse deterrent formulation after being struck with a hammer and (B) the test abuse deterrent formulation F9 shown in Table 11.
Figure 10:
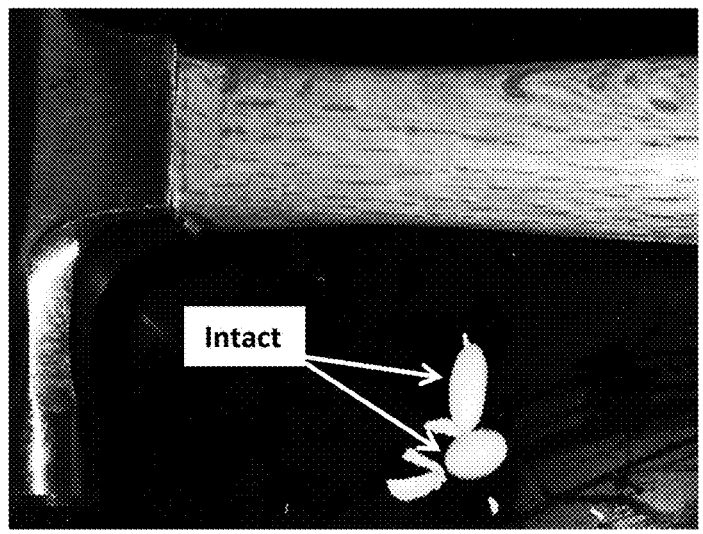
Figure 11:
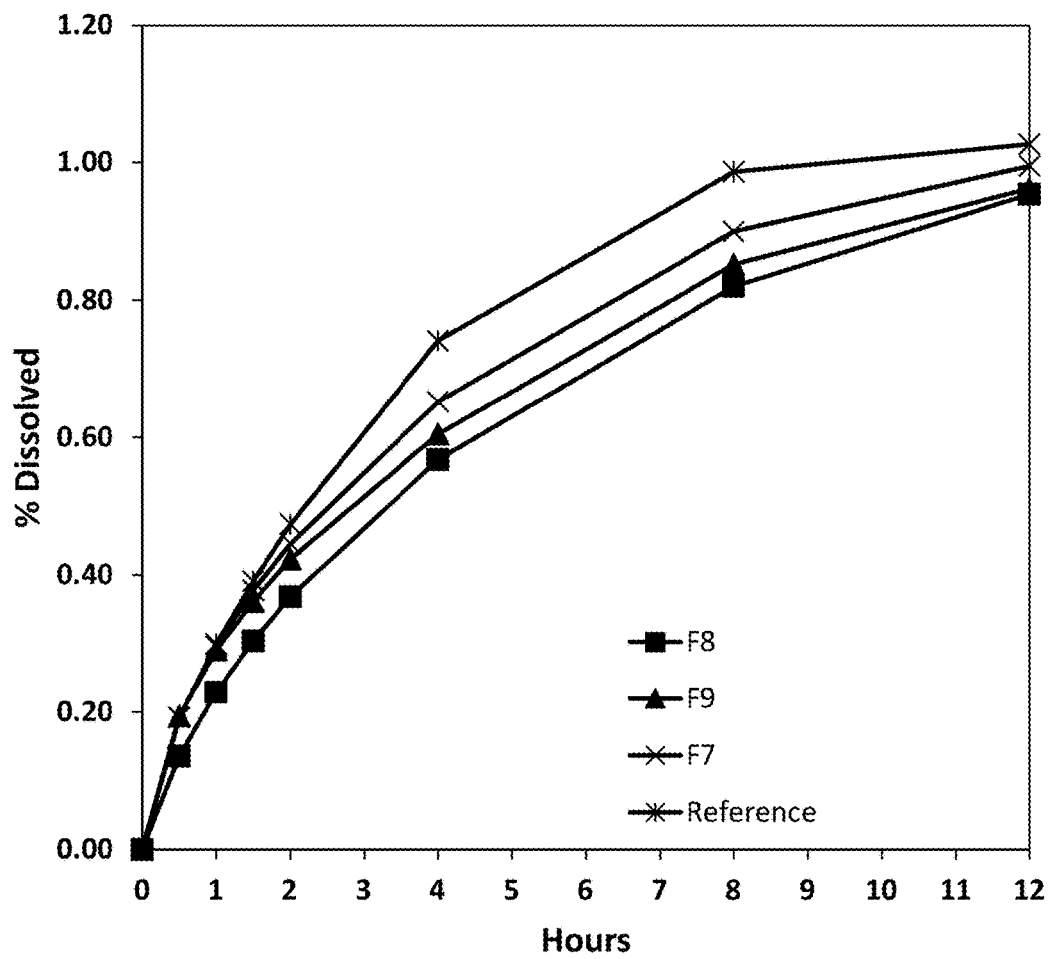
FIG. 11. Percent release of oxycodone from annealed test abuse deterrent pharmaceutical compositions (F7-F9) compared to the percent release of oxycodone from a reference abuse deterrent pharmaceutical composition in simulated gastric fluid.
Figure 12:
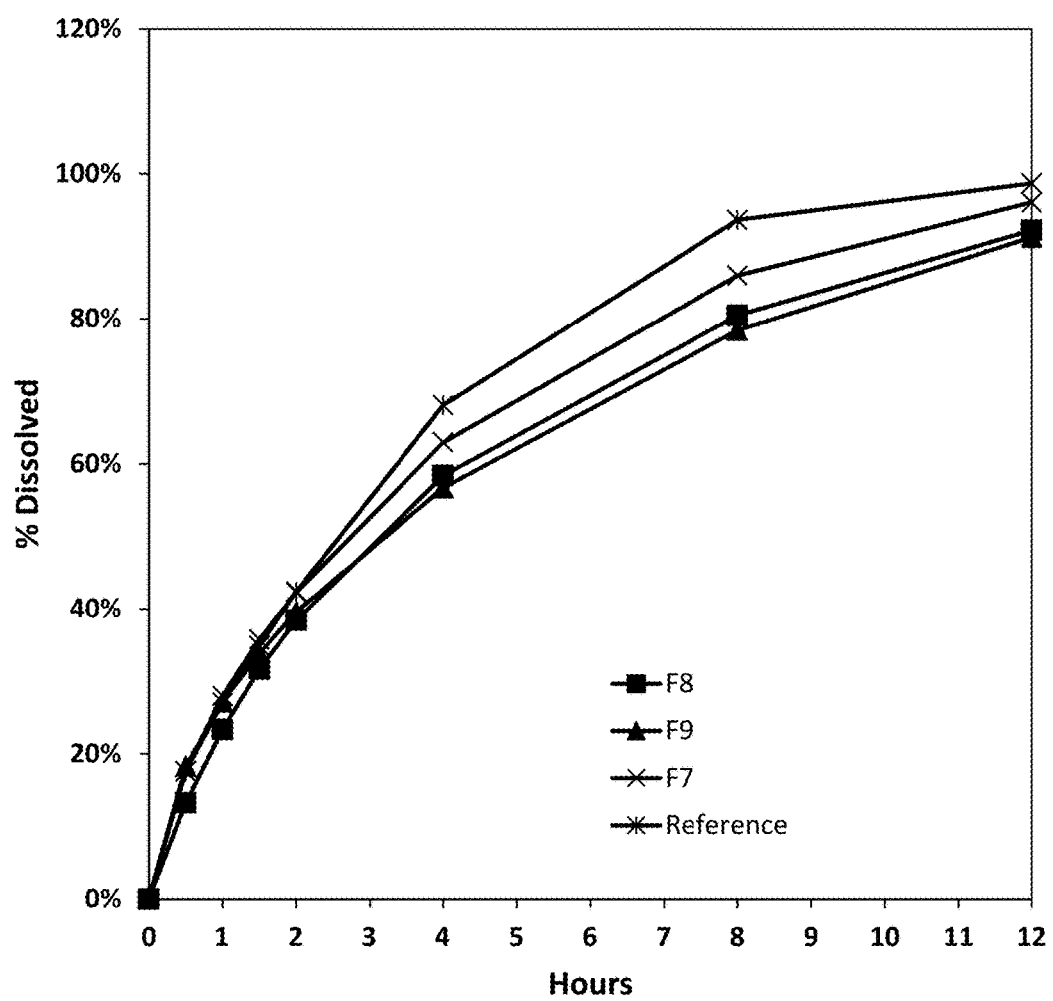
FIG. 12. Percent release of oxycodone from annealed test abuse deterrent pharmaceutical compositions (F7-F9) compared to the percent release of oxycodone from a reference abuse deterrent pharmaceutical composition in simulated gastric fluid containing 5% ethanol.
Figure 13:
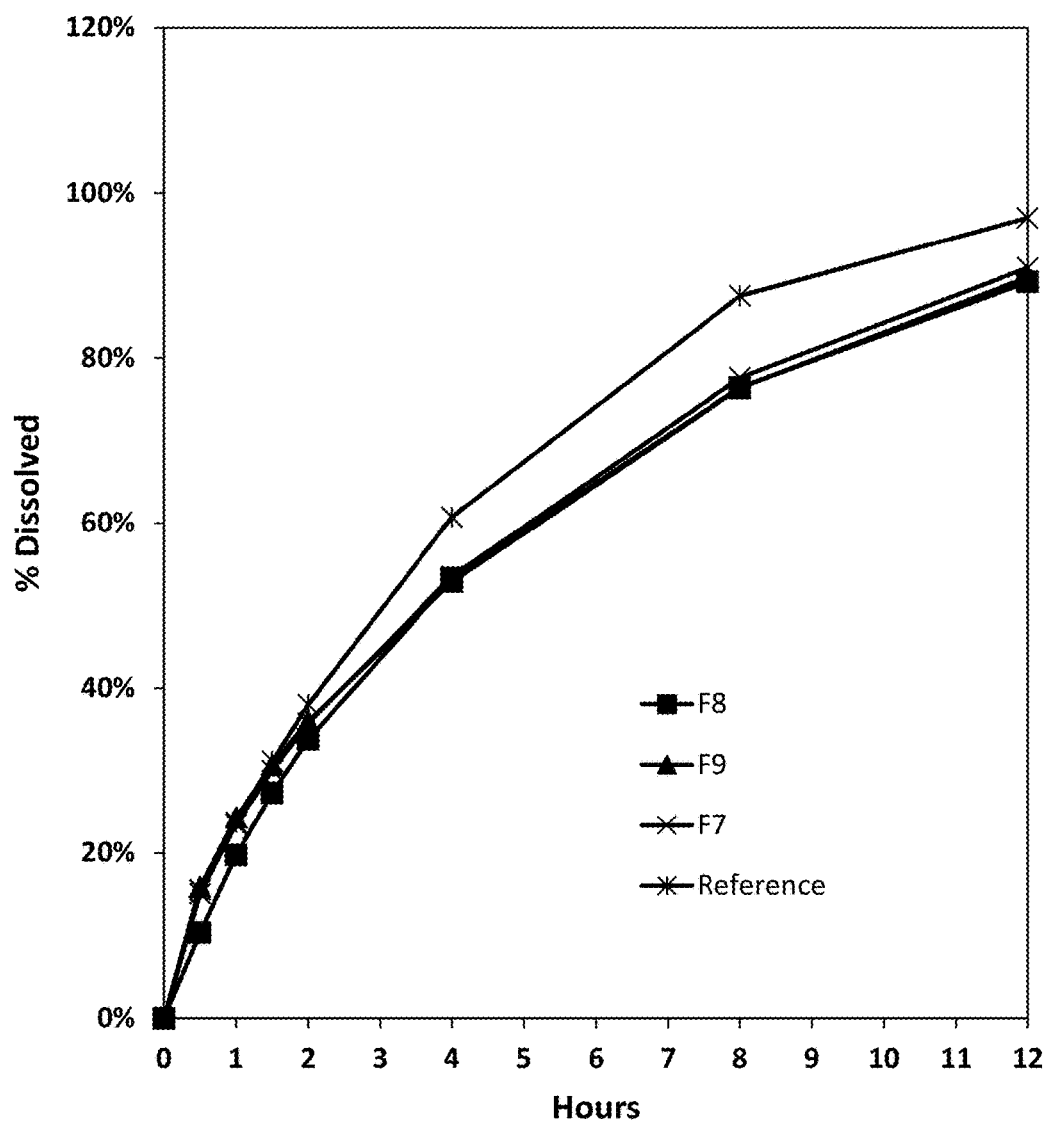
FIG. 13. Percent release of oxycodone from annealed test abuse deterrent pharmaceutical compositions (F7-F9) compared to the percent release of oxycodone from a reference abuse deterrent pharmaceutical composition in simulated gastric fluid containing 20% ethanol.
Figure 14:
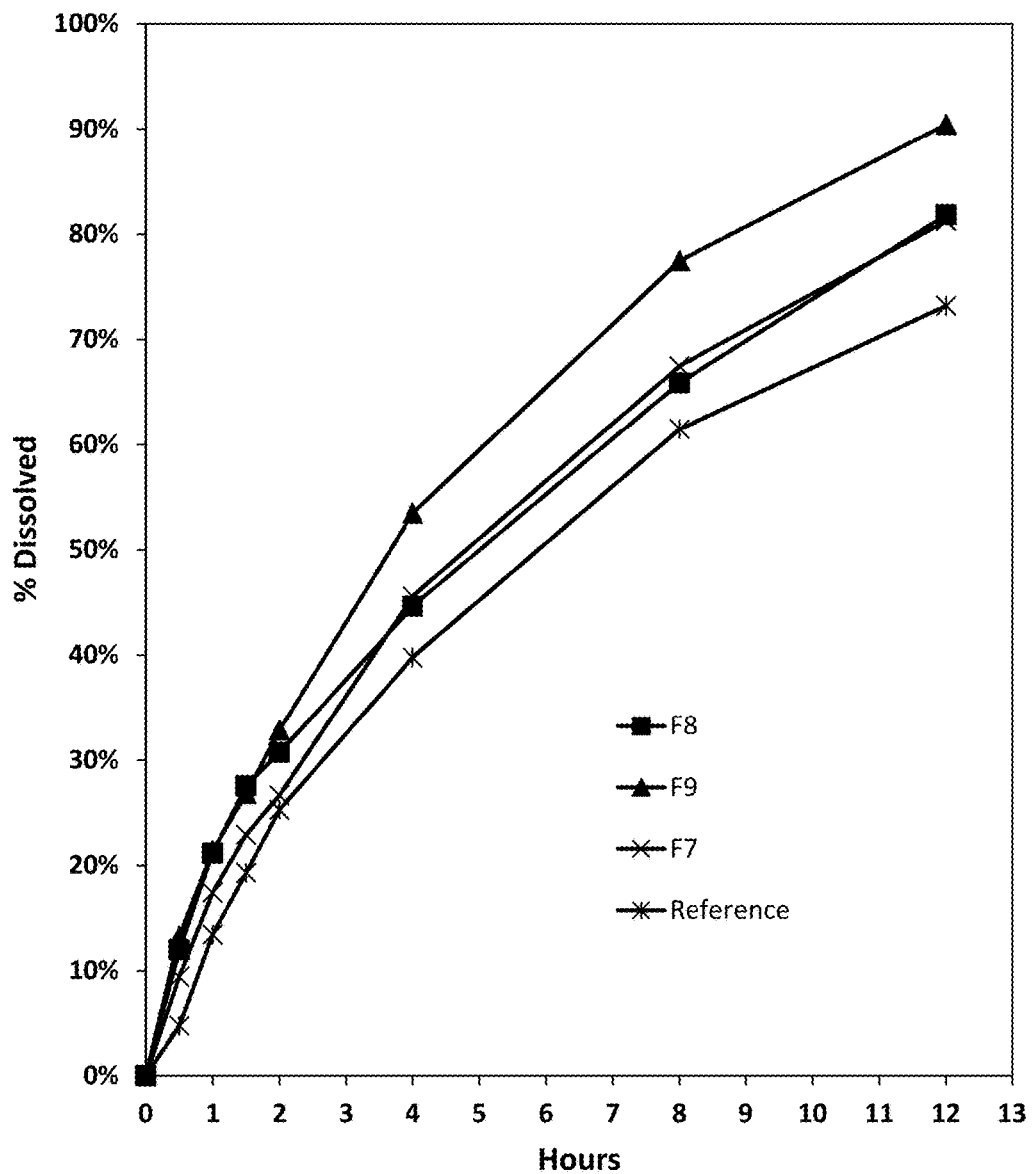
FIG. 14. Percent release of oxycodone from annealed test abuse deterrent pharmaceutical compositions (F7-F9) compared to the percent release of oxycodone from a reference abuse deterrent pharmaceutical composition in simulated gastric fluid containing 40% ethanol.

Next, the abuse deterrent properties of a pharmaceutical composition comprising the different abuse deterrent matrix formulations (F7-F10) of Tables 8-11 were tested. These compositions were subjected to a variety of common physical manipulations, including crushing, grating, grinding and cutting and compared to a similarly manipulated commercially available reference abuse deterrent formulations. The test formulations were highly resistant to crushing with a hammer due to the matrix having rubbery, semi-solid, slippery characteristics (FIG. 10B). By comparison, a reference abuse deterrent formulation was easily crushed into powder like smaller pieces by a hammer or a mortar and pestle (FIG. 10A). The smaller pieces of the reference formulation were then easily converted to a powder using a mortar and pestle, which likely could be snorted. In contrast, the test formulations could be cut into smaller pieces with a cheese grater, coffee grinder, or other sharp cutting tools, but these smaller pieces would not form a powder suitable for insufflation.

The dose dumping of oxycodone from the test abuse deterrent formulations (F7-F9) of Tables 8-10 using increasing concentrations of ethanol were next tested and compared to a commercially available reference abuse deterrent formulation containing oxycodone. These dissolution experiments were carried out in simulated gastric fluid (no enzymes) with 0%, 5%, 20%, and 40% ethanol using an Apparatus I (baskets) at 100 RPM according to USP specifications for oxycodone HCl tablets. As shown in FIGS. 11-14, both the test abuse deterrent formulations and the reference abuse deterrent formulation demonstrated resistence to alcohol extraction or alcohol dose dumping.

Figure 15:
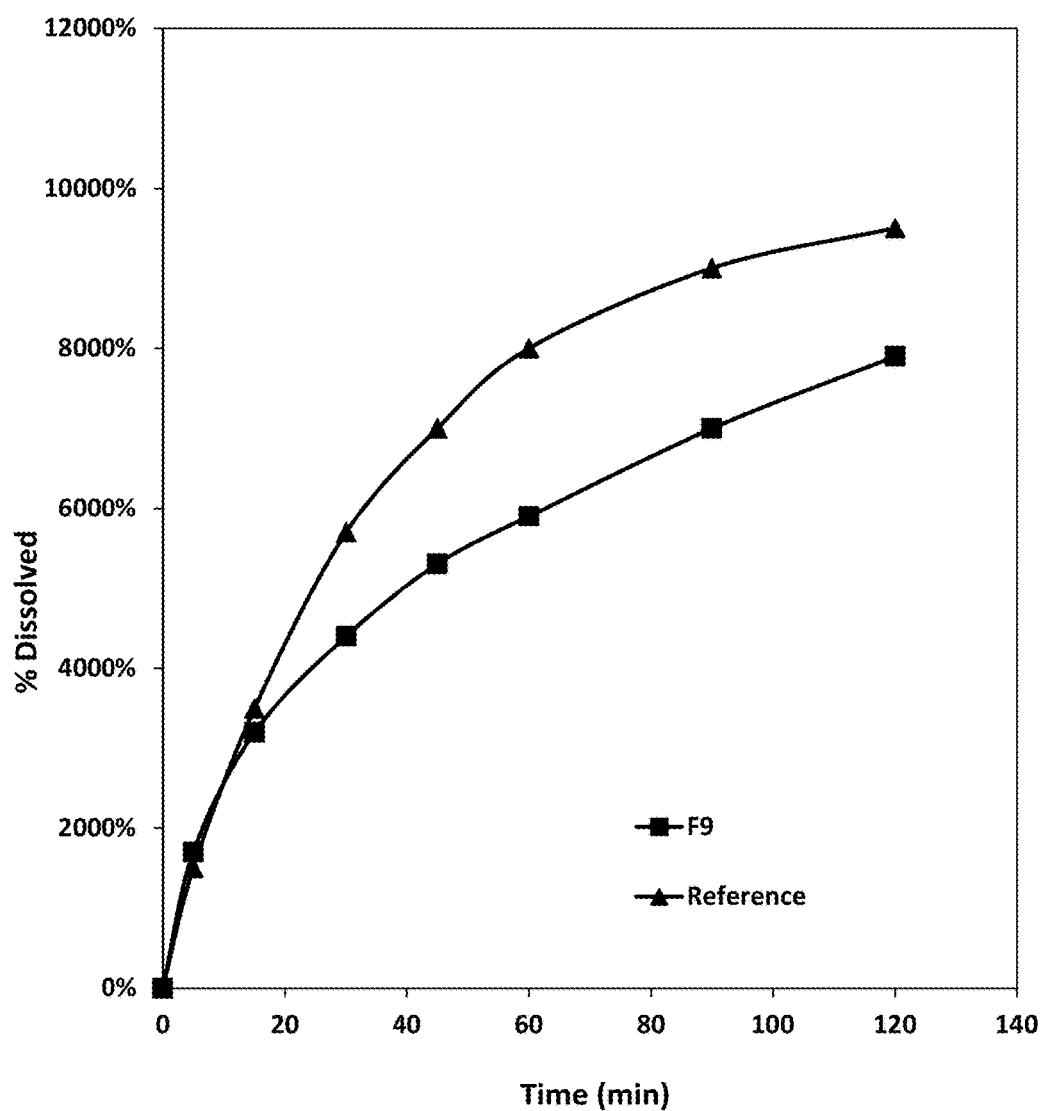
FIG. 15. Percent release of oxycodone from an annealed intact test abuse deterrent pharmaceutical composition (F9) compared to the percent release of oxycodone from an intact reference abuse deterrent pharmaceutical composition under aqueous boiling conditions.
Figure 16:
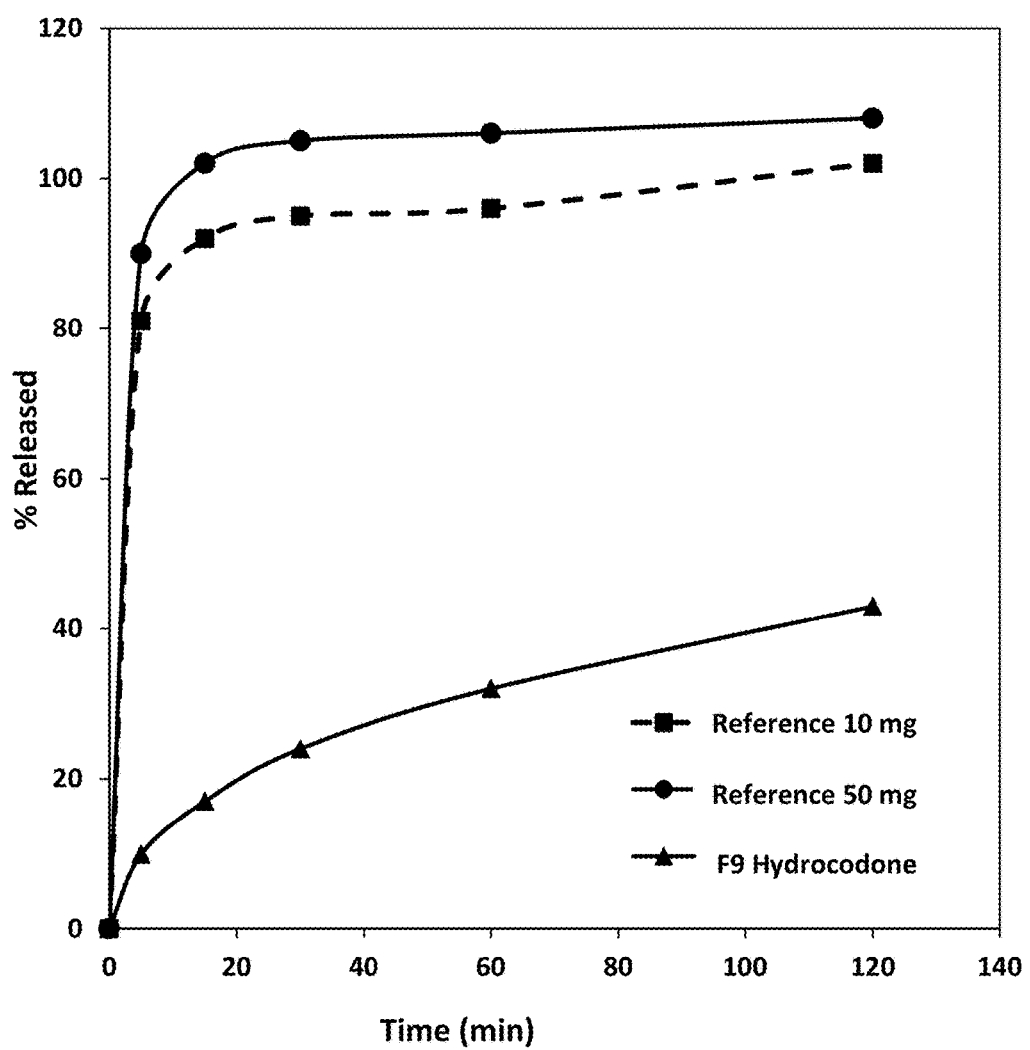
FIG. 16. Percent release of hydrocodone from an intact annealed test abuse deterrent pharmaceutical composition (F10) compared to the percent release of hydrocodone from 10 mg and 50 mg intact reference abuse deterrent pharmaceutical compositions under aqueous boiling conditions.
Figure 17:
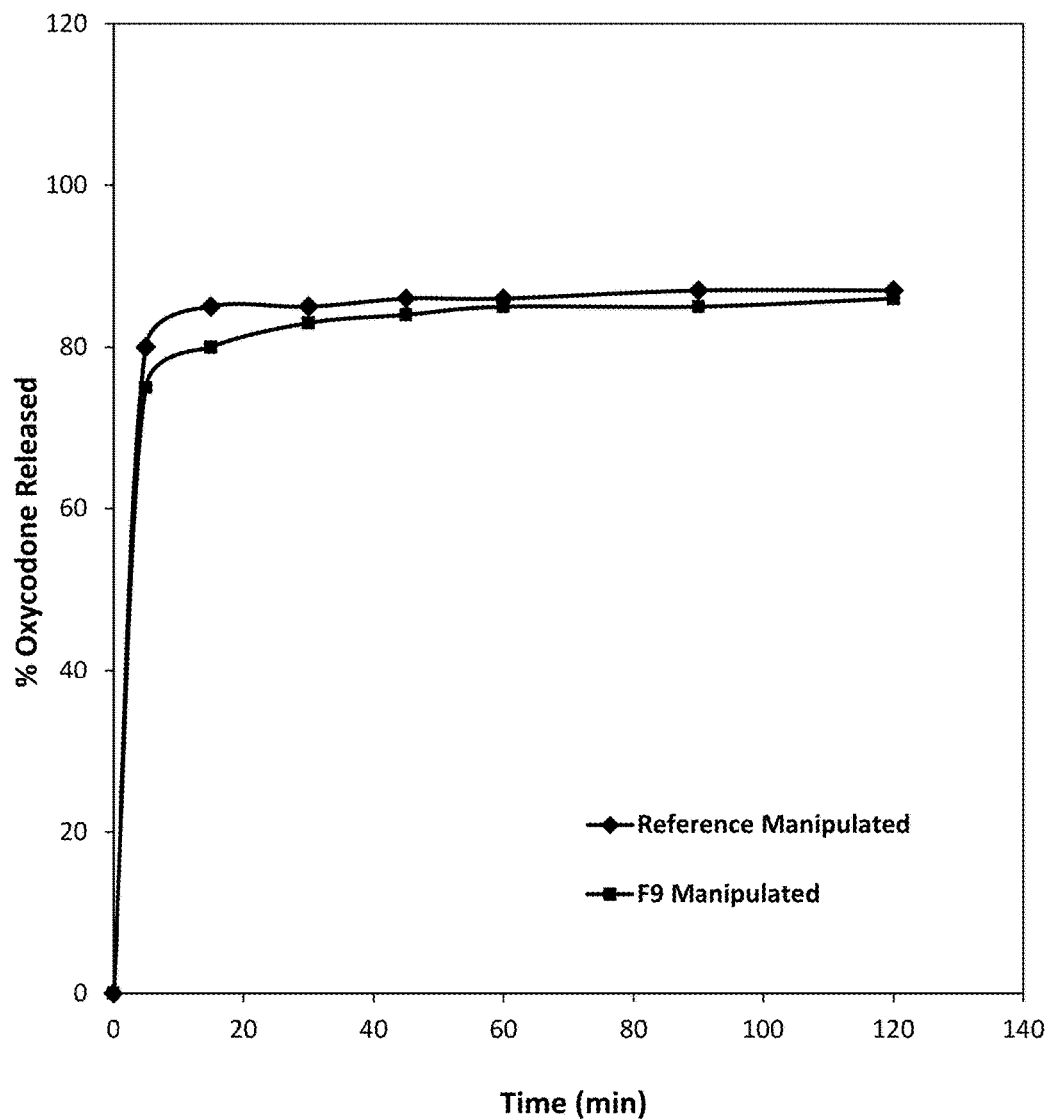
FIG. 17. Percent release of oxycodone from a physically manipulated (ground with a coffee grinder) annealed test abuse deterrent pharmaceutical composition (F9) compared to the percent release of oxycodone from a physically manipulated (crushed with a mortar and pestle) reference abuse deterrent pharmaceutical composition under aqueous boiling conditions.
Figure 18:
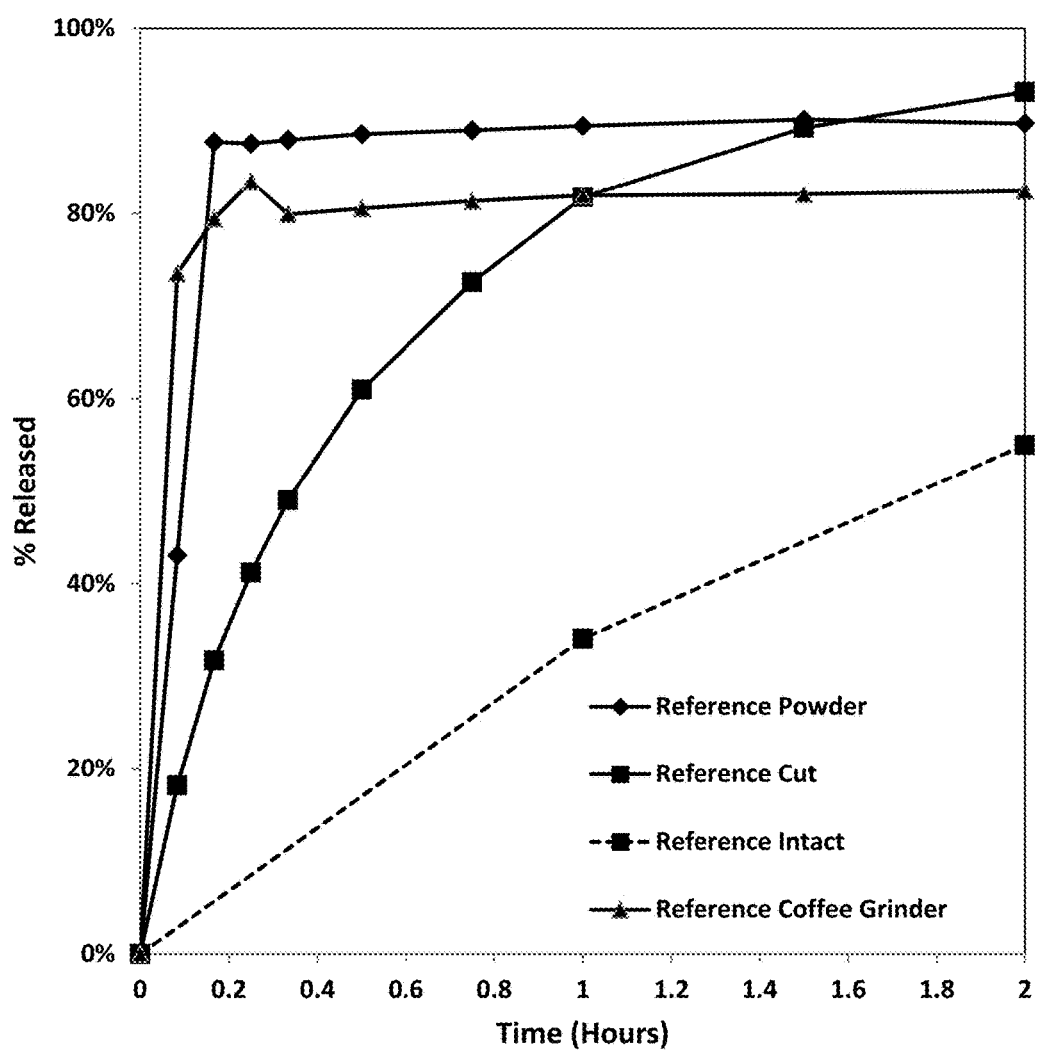
FIG. 18. Percent release of oxycodone from a reference abuse deterrent pharmaceutical composition intact or manipulated by crushing with a mortar and pestle, grinding with a coffee grinder, or cutting under dissolution conditions in FaSSGF using Apparatus III at 30 dips per minute.
Figure 19:
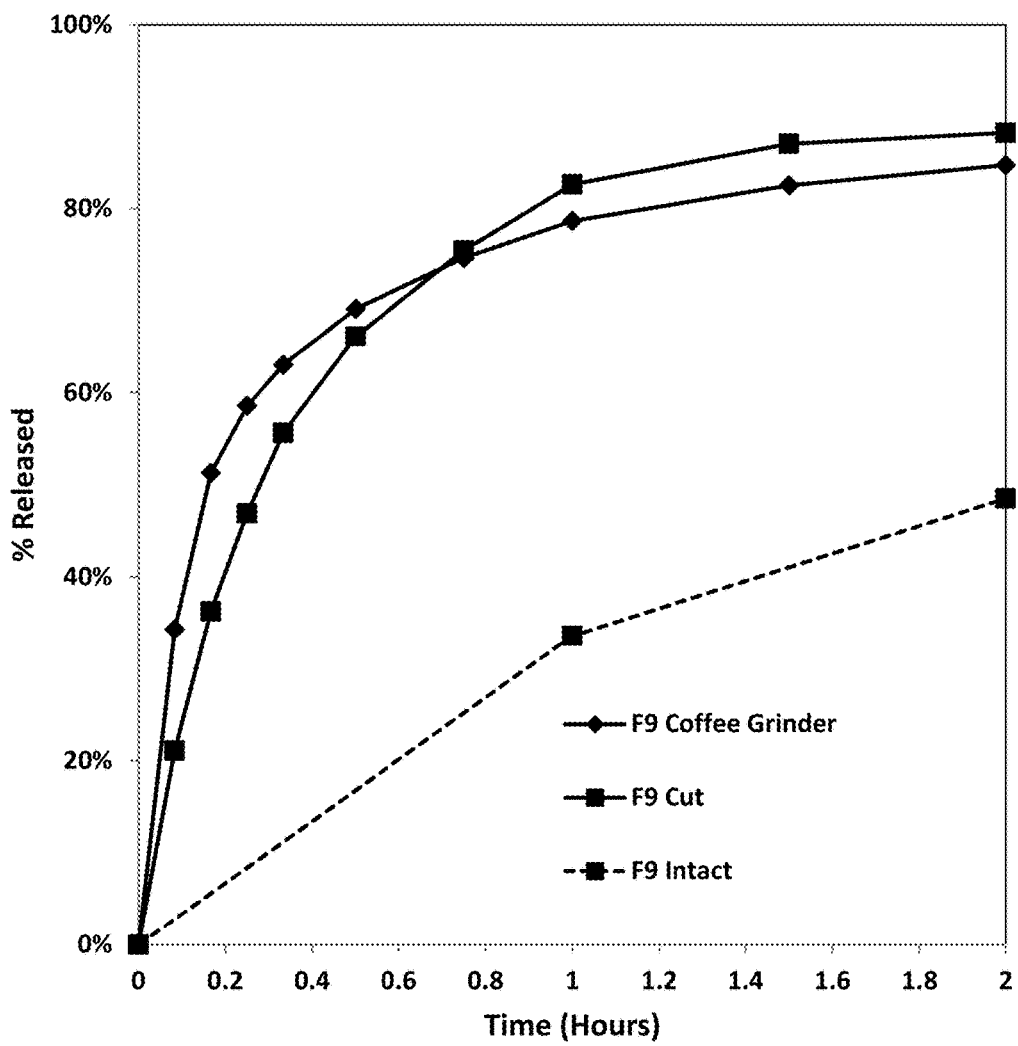
FIG. 19. Percent release of oxycodone from a test abuse deterrent pharmaceutical composition (F9) intact or manipulated by grinding with a coffee grinder or cutting under dissolution conditions in fasted simulated gastric fluid using Apparatus III at 30 dips per minute.
Figure 20:
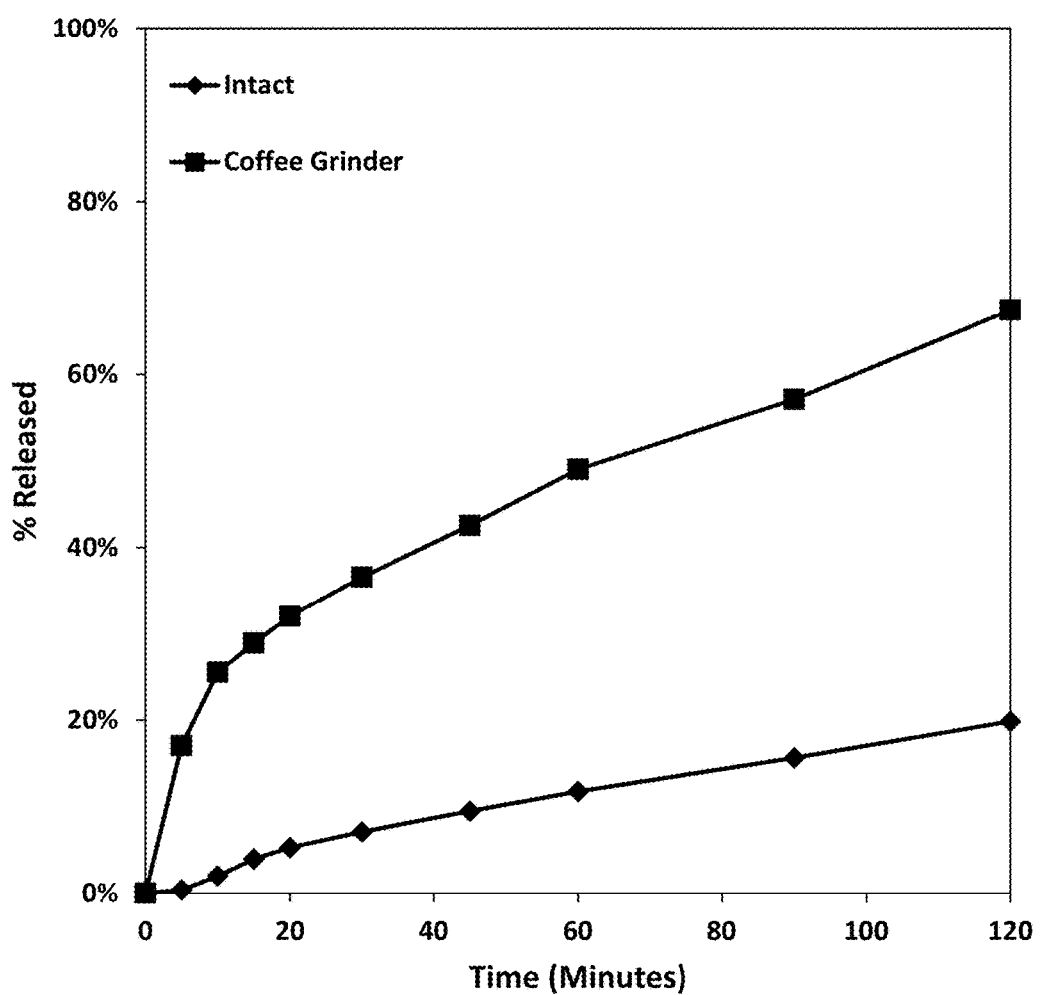
FIG. 20. Percent release of hydrocodone from a test abuse deterrent pharmaceutical composition (F10) intact or manipulated by grinding with a coffee grinder under dissolution conditions in FaSSGF using Apparatus III at 30 dips per minute.
Figure 21:
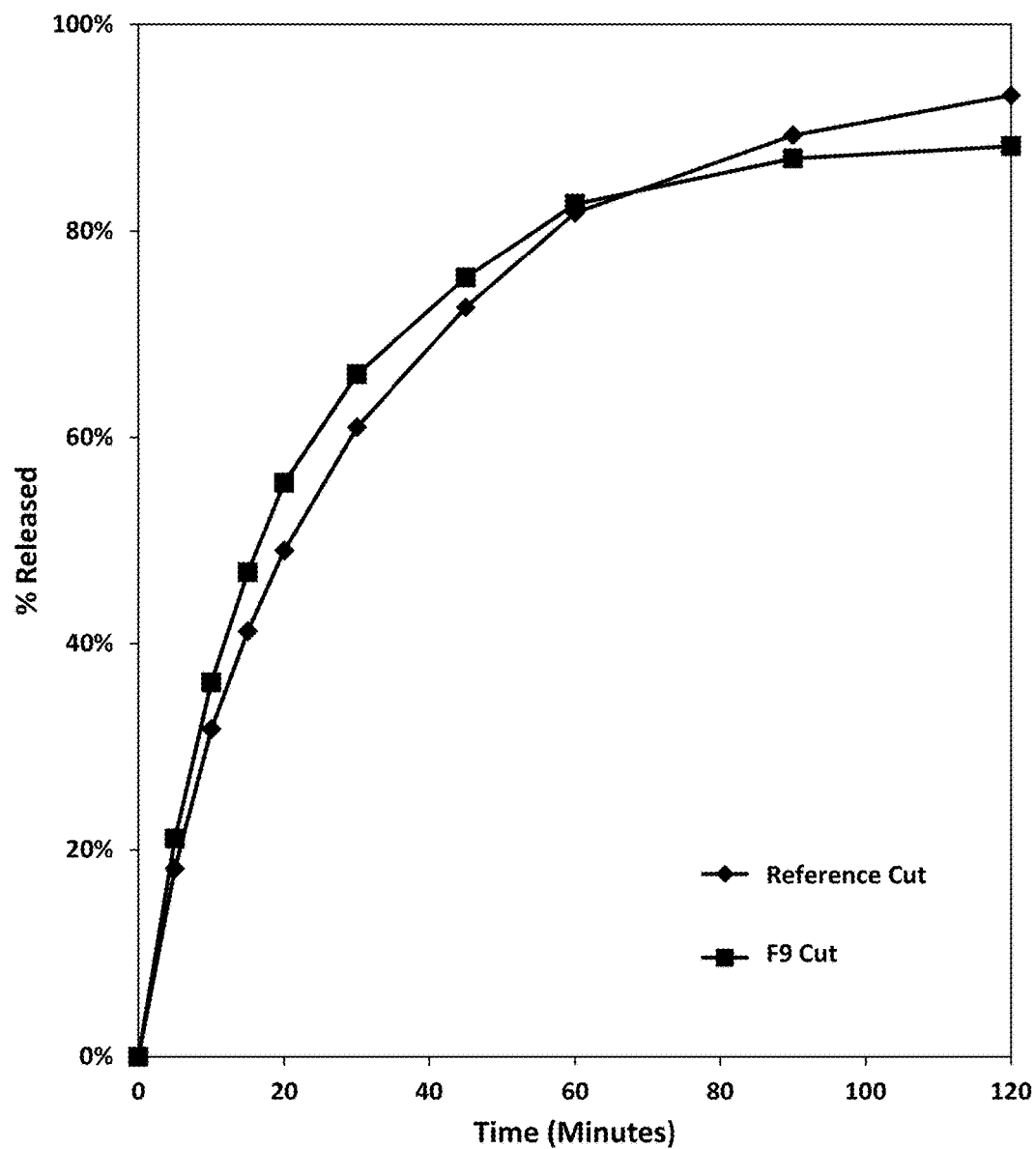
FIG. 21. Percent release of oxycodone from a test abuse deterrent pharmaceutical composition (F9) compared to a reference abuse deterrent pharmaceutical composition manipulated by cutting under dissolution conditions in FaSSGF using Apparatus III at 30 dips per minute.
Figure 22:
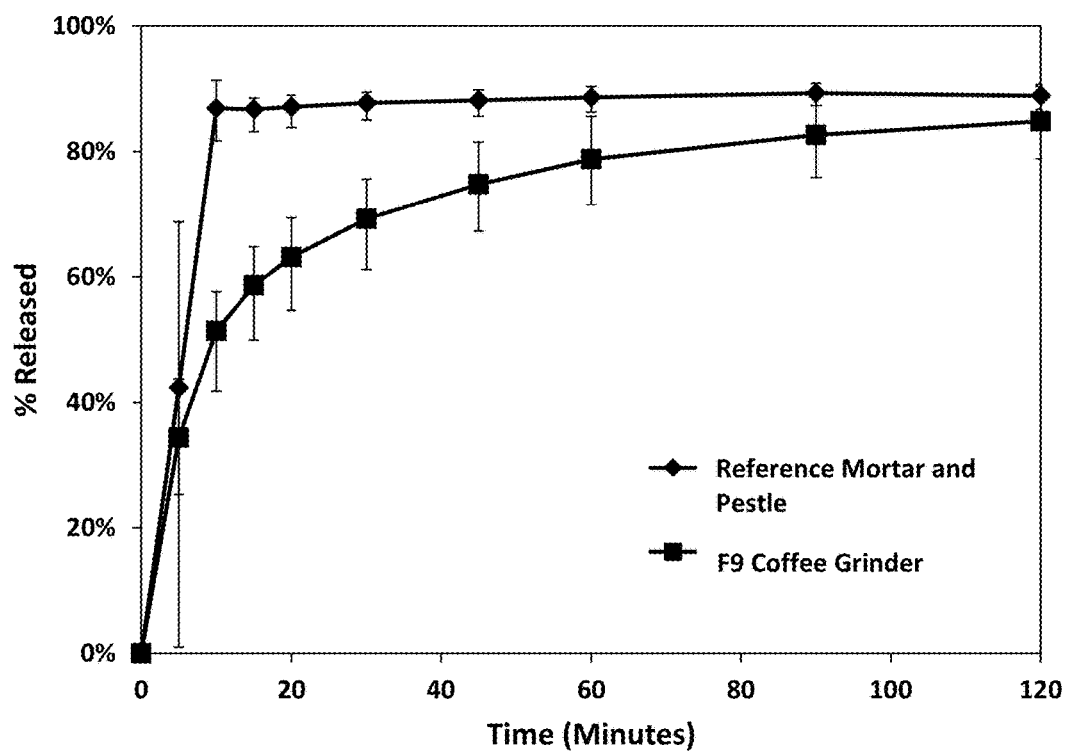
FIG. 22. Percent release of oxycodone from a test abuse deterrent pharmaceutical composition (F9) manipulated by cutting compared to a reference abuse deterrent pharmaceutical composition manipulated by crushing with a mortar and pestle under dissolution conditions in FaSSGF using Apparatus III at 30 dips per minute.

Next, the extraction of oxycodone or other opioid analgesic from a test abuse deterrent formulation (F9) of Table 10 under boiling conditions was tested and compared to commercially available reference abuse deterrent formulations containing either oxycodone or other opioid analgesic. While intact, formulation F9 and F10 demonstrated significantly better boiling resistence for the extraction of oxycodone compared to the reference formulations as shown in FIGS. 15 and 16, respectively. The test abuse deterrent formulation (F9) and the reference abuse deterrent formulation containing oxycodone were then physically manipulated using a mortar and pestle or a coffee grinder, respectively. An amount of each formulation corresponding to the approximate weight of each of the intact compositions was used in an aqueous boiling extraction study. Accordingly, each formulation demonstrated similar release kinetics (FIG. 17).

The effects of physical manipulation on the dissolution of the test abuse deterrent formulation F9 of Table 10 and formulation F10 of Table 11 and a commercially available reference abuse deterrent formulation containing oxycodone or hydrocodone were tested. The reference formulation was manipulated by cutting, grinding, and crushing with a mortar and pestle and the test formulations (F9 and F10) were manipulated by cutting and/or grinding with a coffee grinder. The manipulated formulations were dissolved in an Apparatus III (reciprocating cylinder) at 30 dips per minute (most aggressive setting) in FaSSGF media and evaluated for 2 hours (FIGS. 18-22).

Figure 23:
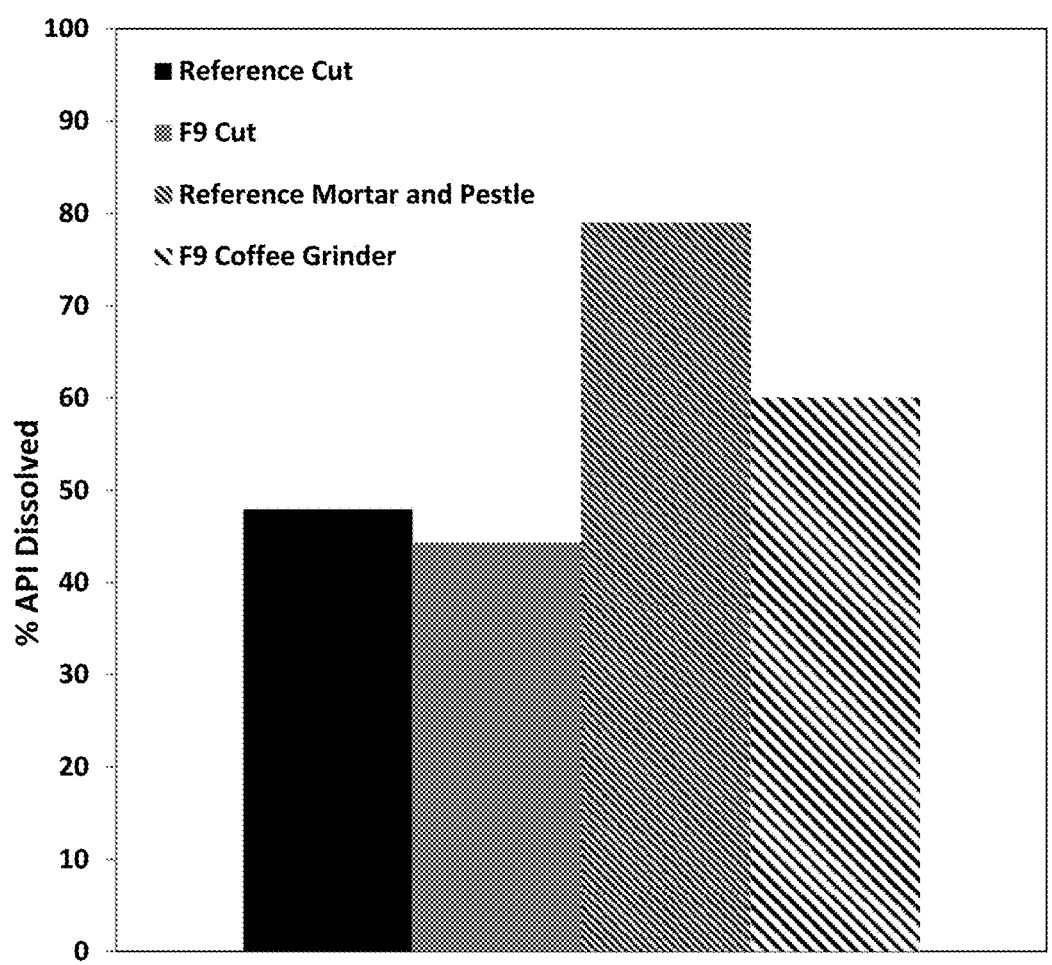
FIG. 23. Test for syringability of a reference abuse deterrent pharmaceutical composition manipulated by crushing with a mortar and pestle or cutting compared to a test abuse deterrent pharmaceutical composition (F9) manipulated by cutting or grinding with a coffee grinder followed by shaking agitation for 30 minutes in container having 10 mL of water FIG. 24. Test for syringability of a reference abuse deterrent pharmaceutical composition manipulated by crushing with a mortar and pestle or cutting compared to a test abuse deterrent pharmaceutical composition (F9) manipulated by cutting or grinding with a coffee grinder followed by agitation for 30 minutes in container having 10 mL of water in a water bath at 200 RPM at 90-95° C.
Figure 24:
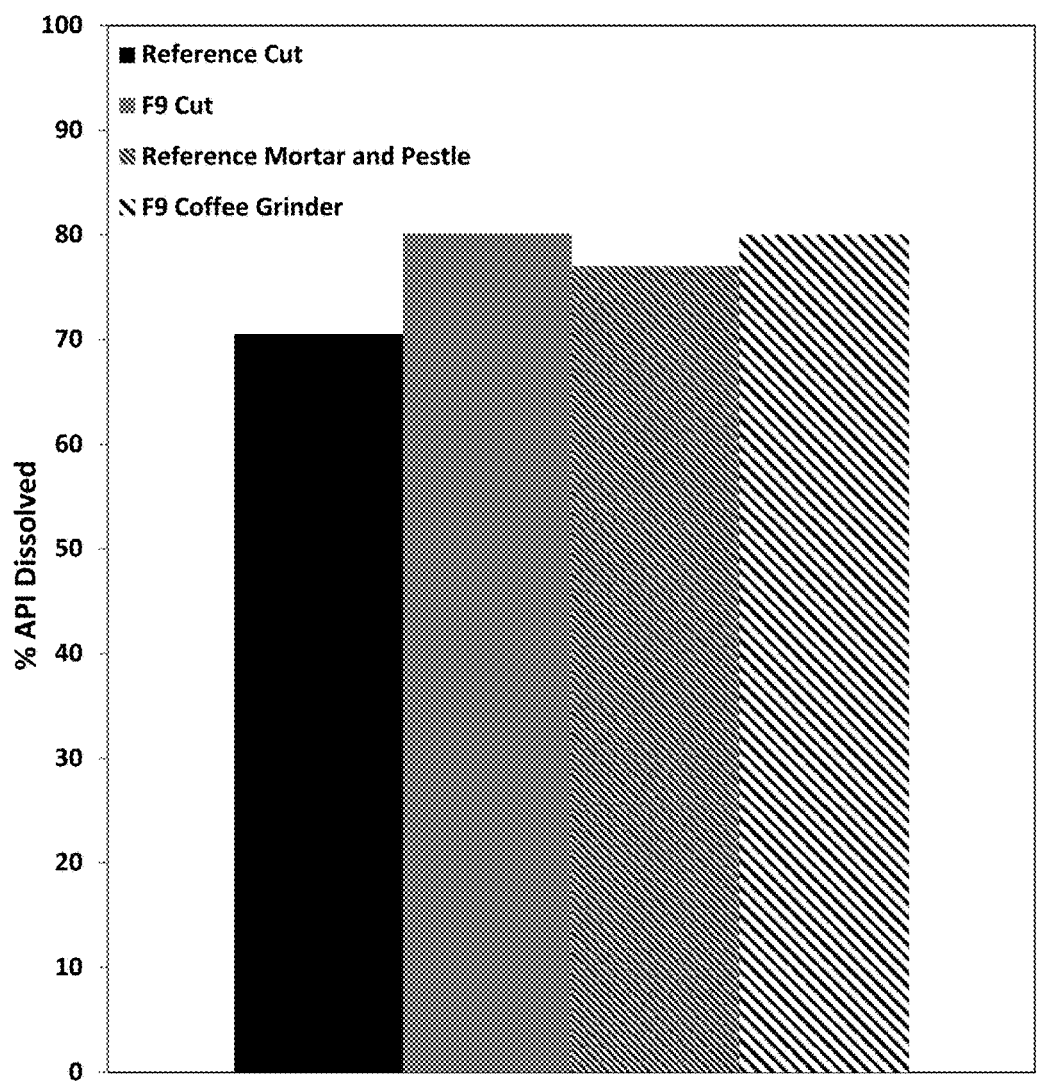

Next, the ability to extract and inject oxycodone from a physically manipulated test abuse deterrent formulation F9 of Table 10 and a physically manipulated commercially available reference abuse deterrent formulation was assessed. The injectability/syringability of the compositions was determined by grinding the test abuse deterrent formulation F9 of Table 10 in a coffee grinder or cutting it using a sharpened edge. The reference abuse deterrent formulation was manipulated by crushing it with a mortar and pestle or cutting it with a sharpened edge. The manipulated products were then agitated for 30 minutes with a wrist action shaker at room temperature or in a water bath shaker at 95° C. at 200 RPM. The extraction results of oxycodone from the various physical manipulations are shown in FIGS. 23 and 24. It was found that neither the test nor the reference abuse deterrent formulations were able to be drawn through a syringe connected to a 29.5 gauge needle due to the high viscosity of the manipulated matrices, limiting the potential for injection (data not shown).

The test abuse deterrent formulation F9 of Table 10 was tested in an additional injectability test, which assays whether a physically manipulated pharmaceutical composition can pass through a cigarette filter and into a syringe for injection. Like the needle study, the manipulated test formulation F9 was to viscous and could not be drawn into the syringe, and thus, also passed this additional injectability test (data not shown).

Example 6

Additional exemplary abuse deterrent matrix compositions useful for producing abuse deterrent pharmaceutical compositions as described herein are shown in Tables 14-15. Composition components are set forth by weight percentage of the total weight of the matrix mass composition. Such compositions may be encapsulated in soft capsules, enteric soft capsules, hard capsules or enteric hard capsules.

Example 7

A clinical study was performed with a single-dose, five-period, five-treatment, five-way crossover relative bioavailability study comparing four test abuse deterrent formulations (F7-F9 and F11) of a 40 mg oxycodone hydrochloride capsule and compared with a commercial abuse deterrent 40 mg oxycodone tablet reference under fasted conditions This study was a pilot, single-dose, open-label, randomized, five-period, five-treatment, five-sequence, five-way crossover study. Twenty-five healthy subjects were enrolled. Subjects who successfully completed the screening process checked into the research center the evening before first dose. Subjects who continued to meet inclusion/exclusion criteria the morning of dose were assigned a subject number, based on the order in which they successfully completed the screening process and procedures as outlined in the study protocol. Subjects were randomly assigned to a treatment sequence and received five separate single-dose administrations of study medication, one treatment per period, according to the randomization schedule. Dosing days were separated by a washout period of at least 7-days. Subjects

TABLE 14

Exemplary Abuse Deterrent Controlled Release Matrix Compositions

| Components | Weight Percentage (%) | | | | | |
|---|---|---|---|---|---|---|
| | EX 1 | EX 2 | EX 3 | EX 4 | EX 5 | EX 6 |
| Flowability Enhancer (e.g., Capmul ® MCM; Oleic Acid; and/or Maisine 35-1) | 68 | 65 | 56 | 50 | 52 | 40 |
| Release Modifier (e.g., Polyethylene oxide; PVP K90; and/or Ethocel ™ 20 cP) | 30 | 30 | 30 | 30 | 35 | 50 |
| Carboxyvinyl polymers (Carbopol 974 P) | 1 | — | 4 | — | 3 | — |
| BHT | 0.1 | 0.1 | 0.1 | 0.1 | 0.1 | 0.1 |
| BHA | 0.25 | 0.25 | 0.25 | 0.25 | 0.25 | 0.25 |
| Active Pharmaceutical Ingredient(s); (e.g., hydrocodone, oxycodone, naloxone, methylnaltrexone, naltrexone) | 1 | 5 | 10 | 20 | 10 | 10 |
| TOTAL | 100 | 100 | 100 | 100 | 100 | 100 |

TABLE 15

Exemplary Abuse Deterrent Controlled Release Matrix Compositions

| Components | Weight Percentage (%) | | | | | |
|---|---|---|---|---|---|---|
| | EX 7 | EX 8 | EX 9 | EX 10 | EX 11 | EX 12 |
| Flowability Enhancer (e.g., Capmul ® MCM; Oleic Acid; and/or Maisine ™ 35-1) | 60 | 70 | 68 | 63 | 75 | 40 |
| Release Modifier (e.g., Polyethylene oxide; PVP K90; and/or Ethocel ™ 20 cP) | 25 | 15 | 22.5 | 27.5 | 23.4 | 40 |
| Carboxyvinyl polymers (Carbopol ® 974 P) | 5 | 5 | — | — | — | — |
| BHT | 0.1 | 0.1 | 0.1 | 0.1 | 0.1 | 0.1 |
| BHA | 0.25 | 0.25 | 0.25 | 0.25 | 0.25 | 0.25 |
| Active Pharmaceutical Ingredient(s); (e.g., oxycodone, hydrocodone, naloxone, methylnaltrexone, naltrexone) | 10 | 10 | 10 | 10 | 1 | 20 |
| TOTAL | 100 | 100 | 100 | 100 | 100 | 100 | received each of the treatments listed below during the five treatment periods as shown in Table 16.

TABLE 16

Study Treatment Protocol

| | |
|---|---|
| Treatment A: | FORMULATION F11<br>Oxycodone hydrochloride extended-release capsule, 40 mg<br>Dose = 1 × 40 mg capsule |
| Treatment B: | FORMULATION F8<br>Oxycodone hydrochloride extended-release capsule, 40 mg<br>Dose = 1 × 40 mg capsule |
| Treatment C: | FORMULATION F9<br>Oxycodone hydrochloride extended-release capsule, 40 mg<br>Dose = 1 × 40 mg capsule |
| Treatment D: | FORMULATION F7<br>Oxycodone hydrochloride extended-release capsule, 40 mg<br>Dose = 1 × 40 mg capsule |
| Treatment E: | Reference Product<br>Commercial (oxycodone hydrochloride) extended-release tablet, 40 mg<br>Dose = 1 × 40 mg tablet |

Clinical Procedures Summary

During each study period, 4 mL blood samples were obtained prior to each dosing and following each dose at selected times through 36-hours post-dose. A total of 95 pharmacokinetic blood samples were to be collected from each subject, 19 samples in each study period. In addition, blood was drawn and urine was collected for clinical laboratory testing at screening and study exit.

In each study period, subjects were admitted to the study unit in the evening prior to the scheduled dose. Subjects were confined to the research center during each study period until completion of the 36-hour blood collection and other study procedures.

Procedures for Collecting Samples for Pharmacokinetic Analysis

Blood samples (1×4 mL) were collected in vacutainer tubes containing K2-EDTA as a preservative at pre-dose (0) and at 0.5, 1, 1.5, 2, 2.5, 3, 3.5, 4, 4.5, 5, 5.5, 6, 7, 8, 12, 18, 24, and 36-hours after dosing.

Bioanalytical Summary

Plasma samples were analyzed for oxycodone by Worldwide Clinical Trials Early Phase Services/Bioanalytical Sciences, Inc. (WCT) using a validated LC-MS mass spectrometry procedure. The method was validated for a range of 0.250 to 125 ng/mL for oxycodone, based on the analysis of 0.250 mL of human EDTA plasma. Data were stored in Watson Laboratory Information Management System (LIMS; Version 7.2.0.03, Thermo Fisher Scientific).

Pharmacokinetic Analysis

Concentration time data were transferred from Watson Laboratory Information Management System directly to Phoenix™ WinNonlin® (Version 6.3, Pharsight Corporation) using the Custom Query Builder option for analysis. Data were analyzed by noncompartmental methods in WinNonlin. Concentration time data that were below the limit of quantification (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Full precision concentration data (not rounded to three significant figures) and actual sample times were used for all pharmacokinetic and statistical analyses.

The following pharmacokinetic parameters were calculated: peak concentration in plasma ($C_{max}$), time to peak concentration ($T_{max}$), elimination rate constant ($\lambda_z$), terminal half-life ($t\frac{1}{2}$), area under the concentration-time curve from time-zero to the time of the last quantifiable concentration ($AUC_{last}$), and area under the plasma concentration time curve from time-zero extrapolated to infinity ($AUC_{0 \to \infty}$).

Analysis of variance (ANOVA) and the Schuirmann's two one sided t-test procedures at the 5% significance level were applied to the log-transformed pharmacokinetic exposure parameters, $C_{max}$, $AUC_{last}$, and $AUC_{0 \to \infty}$. The 90% confidence interval for the ratio of the geometric means (Test/Reference) was calculated. Bioequivalence was declared if the lower and upper confidence intervals of the log-transformed parameters were within 80% to 125%.

Example 8

Figure 25:
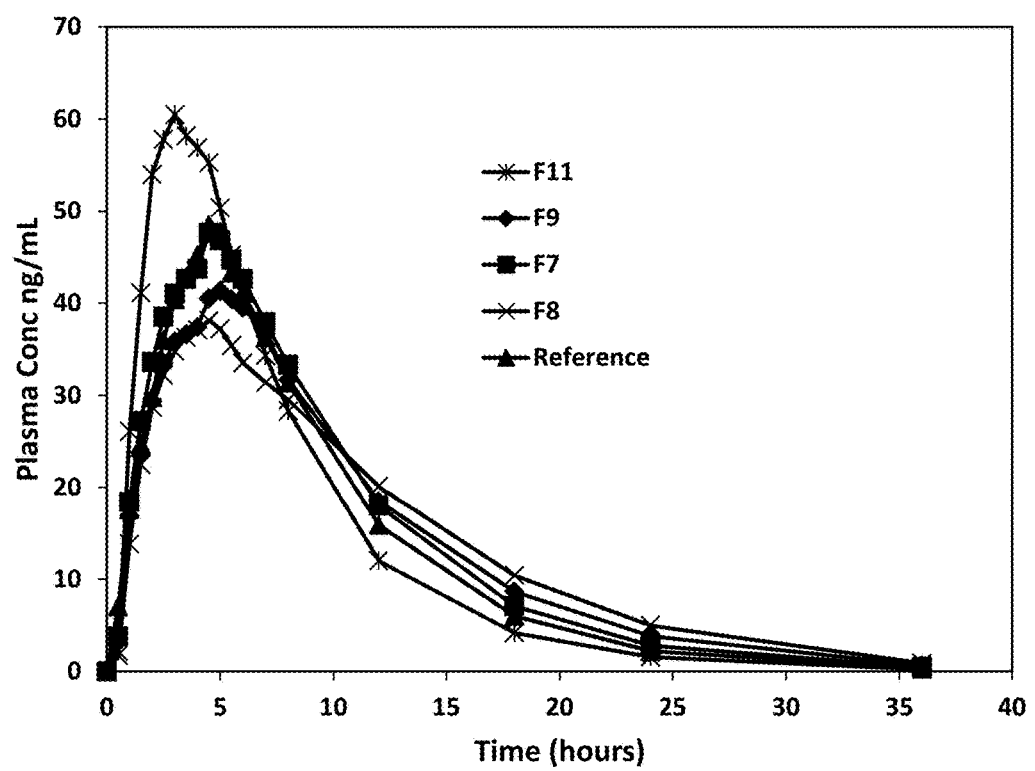
FIG. 25. Mean oxycodone concentration-time profiles after administration of formulation F11 (treatment a), formulation F8 (treatment b), formulation F9 (treatment c), formulation F7 (treatment d), and the reference product (treatment e).
Figure 26:
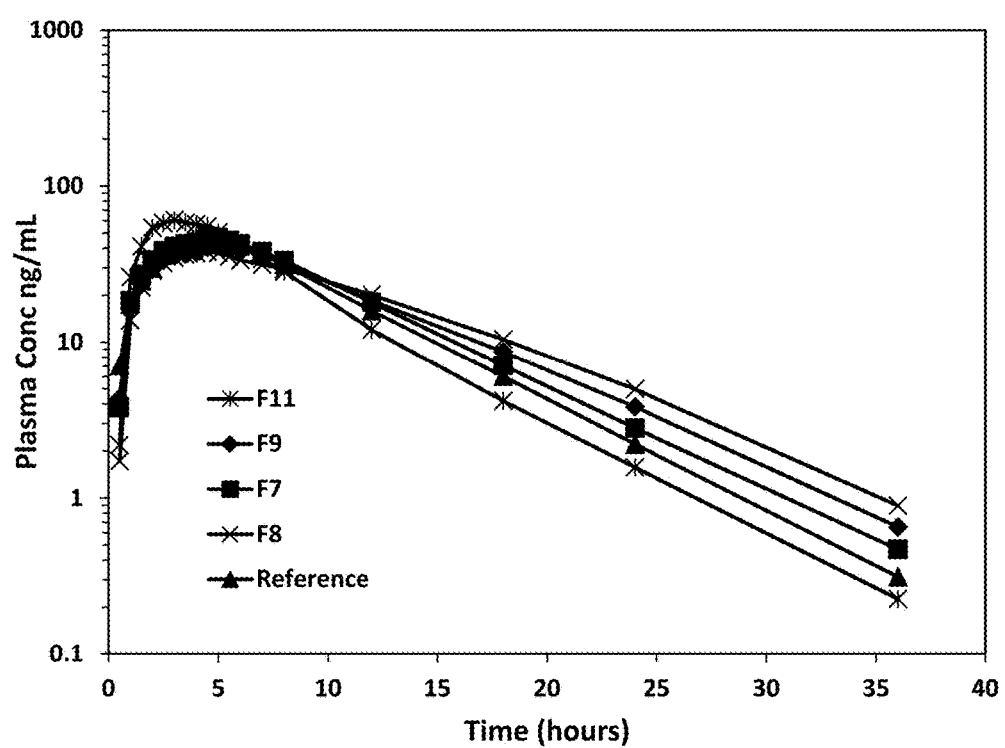
FIG. 26. Mean log-transformed oxycodone concentration-time profiles after administration of formulation F11 (treatment a), formulation F8 (treatment b), formulation F9 (treatment c), formulation F7 (treatment d), and the reference product (treatment e).
Figure 27:
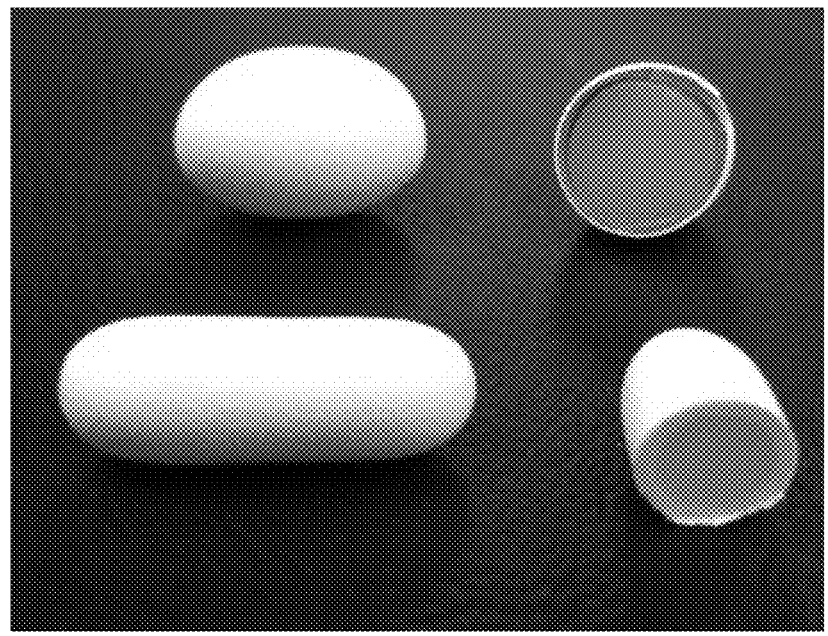
FIG. 27. A. Oval and oblong oxycodone dosage forms and representative cross-sections. B. Micrograph of a dosage form cross section showing the abuse deterrent matrix, gelatin shell, and polyvinyl alcohol (PVA) coating. The PVA coating layer is about 185 μm and the gelatin shell layer is about 650 μm, for a total encapsulation layer of about 810-840 μm.
Figure 27:
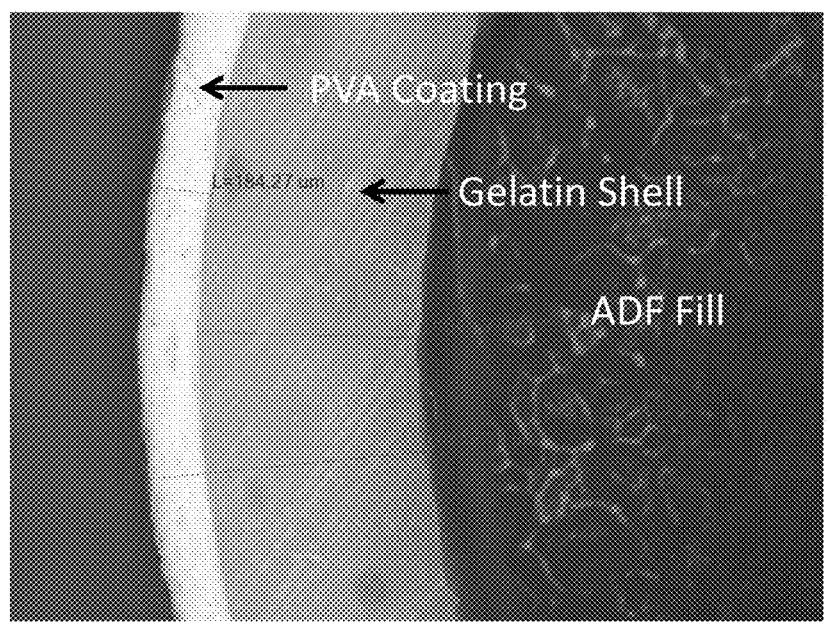
Figure 28:
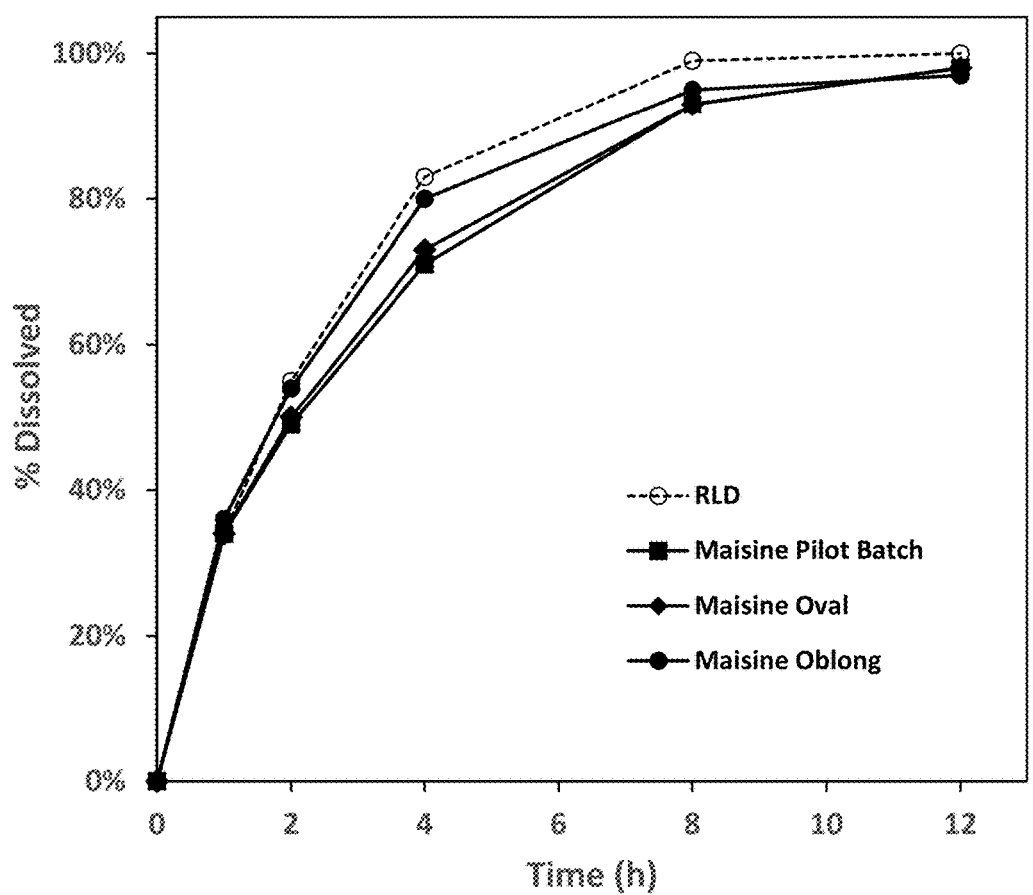
FIG. 28. Dissolution of various oxycodone dosage forms compared with a commercial reference.

The test abuse-deterrent formulations F7-F9 described herein were tested for in vivo bioequivalence to a commercially available reference product and a comparative formulation F11. Data from 25 subjects who completed at least one study period were included in the pharmacokinetic and statistical analyses. Mean concentration-time data are shown in Table 17 and FIGS. 25-26. Results of the pharmacokinetic and statistical analyses are shown below in Tables 18-22.

The 90% confidence interval for comparing the maximum exposure, based on $\ln(C_{max})$, is within the accepted 80% to 125% limits for Treatments FORMULATION F9 and FORMULATION F7.

The 90% confidence intervals for comparing total systemic exposure, based on $\ln(AUC_{last})$ and $\ln(AUC_{0 \to \infty})$, are within the accepted 80% to 125% limits for all test formulations. Therefore, test formulations FORMULATION F9 and FORMULATION F7 of oxycodone hydrochloride extended-release capsule are bioequivalent to a commercial oxycodone product under fasted conditions.

TABLE 17

Oxycodone Concentration-Time Data after Administration of FORMULATION F11 (Treatment A), FORMULATION F8 (Treatment B), FORMULATION F9 (Treatment C), FORMULATION F7 (Treatment D), and the Commercially Available Reference Product (Treatment E)

| | Treatment A: FORMULATION F11 | | | |
|---|---|---|---|---|
| Time (h) | n | Mean (ng/mL) | SD (ng/mL) | CV (%) |
| 0.00 | 23 | 0.00 | 0.00 | NC |
| 0.50 | 23 | 2.18 | 4.24 | 193.98 |
| 1.00 | 23 | 26.1 | 17.5 | 66.89 |
| 1.50 | 23 | 41.1 | 17.8 | 43.28 |
| 2.00 | 23 | 54.0 | 26.0 | 48.18 |
| 2.50 | 23 | 57.8 | 23.0 | 39.86 |
| 3.00 | 23 | 60.5 | 18.7 | 30.91 |
| 3.50 | 23 | 58.2 | 16.9 | 29.10 |
| 4.00 | 23 | 56.9 | 13.3 | 23.31 |
| 4.50 | 23 | 55.3 | 15.5 | 28.00 |
| 5.00 | 23 | 50.4 | 15.0 | 29.69 |
| 5.50 | 23 | 45.2 | 15.2 | 33.57 |
| 6.00 | 23 | 41.0 | 13.6 | 33.07 |
| 7.00 | 23 | 34.3 | 12.9 | 37.59 |
| 8.00 | 23 | 28.3 | 11.5 | 40.67 |
| 12.00 | 23 | 12.0 | 6.45 | 53.76 |

TABLE 17-continued

Oxycodone Concentration-Time Data after Administration of FORMULATION F11 (Treatment A), FORMULATION F8 (Treatment B), FORMULATION F9 (Treatment C), FORMULATION F7 (Treatment D), and the Commercially Available Reference Product (Treatment E)

| Time (h) | n | Mean (ng/mL) | SD (ng/mL) | CV (%) |
|---|---|---|---|---|
| 18.00 | 23 | 4.18 | 2.86 | 68.40 |
| 24.00 | 23 | 1.57 | 1.28 | 81.99 |
| 36.00 | 23 | 0.226 | 0.333 | 147.23 |

Treatment B: FORMULATION F8

| Time (h) | n | Mean (ng/mL) | SD (ng/mL) | CV (%) |
|---|---|---|---|---|
| 0.00 | 23 | 0.00 | 0.00 | NC |
| 0.50 | 23 | 1.72 | 1.80 | 104.64 |
| 1.00 | 23 | 13.8 | 8.76 | 63.69 |
| 1.50 | 23 | 22.5 | 12.4 | 54.92 |
| 2.00 | 23 | 28.7 | 13.3 | 46.50 |
| 2.50 | 23 | 32.2 | 13.3 | 41.29 |
| 3.00 | 23 | 34.8 | 12.2 | 35.03 |
| 3.50 | 23 | 36.3 | 11.6 | 31.95 |
| 4.00 | 23 | 37.1 | 11.9 | 32.04 |
| 4.50 | 23 | 38.1 | 13.6 | 35.60 |
| 5.00 | 23 | 37.2 | 13.4 | 36.11 |
| 5.50 | 23 | 35.4 | 11.6 | 32.75 |
| 6.00 | 23 | 33.5 | 10.8 | 32.31 |
| 7.00 | 23 | 31.4 | 9.51 | 30.33 |
| 8.00 | 23 | 29.5 | 8.92 | 30.24 |
| 12.00 | 23 | 20.1 | 6.65 | 33.09 |
| 18.00 | 23 | 10.4 | 5.32 | 51.34 |
| 24.00 | 23 | 4.98 | 3.62 | 72.61 |
| 36.00 | 23 | 0.893 | 0.734 | 82.20 |

Treatment C: FORMULATION F9

| Time (h) | n | Mean (ng/mL) | SD (ng/mL) | CV (%) |
|---|---|---|---|---|
| 0.00 | 25 | 0.00 | 0.00 | NC |
| 0.50 | 25 | 4.33 | 7.96 | 183.53 |
| 1.00 | 25 | 16.9 | 11.4 | 67.30 |
| 1.50 | 25 | 23.5 | 10.3 | 43.94 |
| 2.00 | 25 | 29.3 | 8.40 | 28.64 |
| 2.50 | 25 | 33.5 | 8.16 | 24.34 |
| 3.00 | 25 | 35.8 | 8.15 | 22.76 |
| 3.50 | 25 | 36.6 | 8.50 | 23.23 |
| 4.00 | 25 | 37.4 | 9.21 | 24.66 |
| 4.50 | 25 | 40.5 | 10.2 | 25.28 |
| 5.00 | 25 | 41.3 | 11.5 | 27.87 |
| 5.50 | 25 | 40.4 | 10.5 | 26.09 |
| 6.00 | 25 | 39.5 | 11.1 | 28.15 |
| 7.00 | 25 | 36.7 | 10.2 | 27.73 |
| 8.00 | 25 | 31.7 | 9.04 | 28.49 |
| 12.00 | 25 | 18.5 | 6.15 | 33.22 |
| 18.00 | 25 | 8.65 | 4.76 | 55.07 |
| 24.00 | 25 | 3.83 | 2.54 | 66.39 |
| 36.00 | 25 | 0.653 | 0.562 | 86.17 |

Treatment D: FORMULATION F7

| Time (h) | n | Mean (ng/mL) | SD (ng/mL) | CV (%) |
|---|---|---|---|---|
| 0.00 | 23 | 0.00 | 0.00 | NC |
| 0.50 | 23 | 3.77 | 4.19 | 111.10 |
| 1.00 | 23 | 18.4 | 8.21 | 44.66 |
| 1.50 | 23 | 27.2 | 8.95 | 32.92 |
| 2.00 | 23 | 33.6 | 9.79 | 29.11 |
| 2.50 | 23 | 38.5 | 11.3 | 29.32 |
| 3.00 | 23 | 41.0 | 10.7 | 26.07 |
| 3.50 | 23 | 42.6 | 11.7 | 27.50 |
| 4.00 | 23 | 43.7 | 12.0 | 27.57 |
| 4.50 | 23 | 47.6 | 13.4 | 28.21 |
| 5.00 | 23 | 46.8 | 12.9 | 27.68 |
| 5.50 | 23 | 44.7 | 12.3 | 27.49 |
| 6.00 | 23 | 42.6 | 12.6 | 29.62 |
| 7.00 | 23 | 37.9 | 11.2 | 29.47 |
| 8.00 | 23 | 33.3 | 9.73 | 29.22 |
| 12.00 | 23 | 18.0 | 4.41 | 24.47 |
| 18.00 | 23 | 7.07 | 2.21 | 31.28 |
| 24.00 | 23 | 2.80 | 0.963 | 34.40 |
| 36.00 | 23 | 0.469 | 0.291 | 62.14 |

Treatment E: Commercially Available Reference Product

| Time (h) | n | Mean (ng/mL) | SD (ng/mL) | CV (%) |
|---|---|---|---|---|
| 0.00 | 23 | 0.00 | 0.00 | NC |
| 0.50 | 23 | 7.04 | 5.73 | 81.40 |
| 1.00 | 23 | 17.6 | 7.06 | 40.20 |
| 1.50 | 23 | 24.7 | 10.5 | 42.39 |
| 2.00 | 23 | 29.8 | 11.6 | 38.91 |
| 2.50 | 23 | 36.0 | 11.3 | 31.30 |
| 3.00 | 23 | 40.4 | 13.0 | 32.11 |
| 3.50 | 23 | 42.8 | 10.0 | 23.36 |
| 4.00 | 23 | 45.2 | 8.91 | 19.72 |
| 4.50 | 23 | 48.5 | 10.7 | 22.06 |
| 5.00 | 23 | 47.7 | 10.9 | 22.83 |
| 5.50 | 23 | 43.3 | 9.96 | 23.00 |
| 6.00 | 23 | 41.2 | 9.30 | 22.60 |
| 7.00 | 23 | 36.3 | 8.49 | 23.39 |
| 8.00 | 23 | 31.4 | 7.76 | 24.74 |
| 12.00 | 23 | 15.9 | 5.97 | 37.62 |
| 18.00 | 23 | 6.01 | 3.09 | 51.34 |
| 24.00 | 23 | 2.21 | 1.43 | 64.48 |
| 36.00 | 23 | 0.313 | 0.346 | 110.42 |

*Plasma samples analyzed using a bioanalytical method with a validated range 0.250 to 125 ng/mL; concentrations reported in ng/mL to 3 significant figures; concentrations below limit of quantification set to zero (0.00 ng/mL) in the data summarization
**NC = Not calculated

TABLE 18

Pharmacokinetic Parameters of Oxycodone

| Parameter | Treatment A: FORMULATION F11 | | | | Treatment B: FORMULATION F8 | | | |
|---|---|---|---|---|---|---|---|---|
| | n | Mean | SD | CV % | n | Mean | SD | CV % |
| $T_{max}$ (h) | 23 | 2.90 | 0.84 | 28.99 | 23 | 4.17 | 1.56 | 37.29 |
| $C_{max}$ (ng/mL) | 23 | 69.3 | 19.0 | 27.40 | 23 | 41.2 | 14.3 | 34.67 |
| $AUC_{last}$ (h * ng/mL) | 23 | 487.1 | 161.1 | 33.08 | 23 | 501.7 | 135.4 | 26.99 |
| $AUC_{0 \to \infty}$ (h * ng/mL) | 23 | 491.3 | 162.2 | 33.01 | 23 | 509.1 | 139.3 | 27.36 |
| $AUC_{Extrap}$ (%) | 23 | 0.90 | 0.37 | 40.85 | 23 | 1.37 | 1.06 | 77.24 |
| $\lambda_z$ (h$^{-1}$) | 23 | 0.1720 | 0.0303 | 17.60 | 23 | 0.1469 | 0.0258 | 17.56 |

TABLE 18-continued

Pharmacokinetic Parameters of Oxycodone

| | | | | | | | | |
|---|---|---|---|---|---|---|---|---|
| $t_{1/2}$ (h) | | 23 | 4.16 | 0.78 | 18.69 | 23 | 4.87 | 0.96 | 19.73 |
| $T_{last}$ (h) | | 23 | 29.22 | 6.08 | 20.82 | 23 | 35.48 | 2.50 | 7.05 |
| $C_{last}$ (ng/mL) | | 23 | 0.731 | 0.338 | 46.16 | 23 | 0.968 | 0.726 | 75.08 |

| | Treatment C: FORMULATION F9 | | | | Treatment D: FORMULATION F7 | | | |
|---|---|---|---|---|---|---|---|---|
| Parameter | n | Mean | SD | CV % | n | Mean | SD | CV % |
| $T_{max}$ (h) | 25 | 4.88 | 1.10 | 22.55 | 23 | 4.46 | 0.94 | 21.10 |
| $C_{max}$ (ng/mL) | 25 | 43.6 | 11.0 | 25.33 | 23 | 50.0 | 13.4 | 26.85 |
| $AUC_{last}$ (h * ng/mL) | 25 | 496.6 | 141.4 | 28.47 | 23 | 506.3 | 116.4 | 22.99 |
| $AUC_{0\to\infty}$ (h * ng/mL) | 25 | 503.2 | 143.7 | 28.56 | 23 | 510.6 | 116.8 | 22.88 |
| $AUC_{Extrap}$ (%) | 25 | 1.28 | 0.80 | 62.95 | 23 | 0.86 | 0.53 | 61.71 |
| $\lambda_z$ ($h^{-1}$) | 25 | 0.1534 | 0.0296 | 19.30 | 23 | 0.1566 | 0.0200 | 12.80 |
| $t_{1/2}$ (h) | 25 | 4.71 | 1.05 | 22.35 | 23 | 4.49 | 0.56 | 12.36 |
| $T_{last}$ (h) | 25 | 33.61 | 4.90 | 14.59 | 23 | 34.43 | 4.13 | 12.00 |
| $C_{last}$ (ng/mL) | 25 | 0.940 | 0.559 | 59.45 | 23 | 0.665 | 0.410 | 61.57 |

| | Treatment E: Reference Product | | | |
|---|---|---|---|---|
| Parameter | n | Mean | SD | CV % |
| $T_{max}$ (h) | 23 | 4.37 | 0.72 | 16.59 |
| $C_{max}$ (ng/mL) | 23 | 50.6 | 11.3 | 22.40 |
| $AUC_{last}$ (h * ng/mL) | 23 | 471.0 | 125.0 | 26.55 |
| $AUC_{0\to\infty}$ (h * ng/mL) | 23 | 475.9 | 125.8 | 26.44 |
| $AUC_{Extrap}$ (%) | 23 | 1.04 | 0.53 | 50.51 |
| $\lambda_z$ ($h^{-1}$) | 23 | 0.1723 | 0.0272 | 15.76 |
| $t_{1/2}$ (h) | 23 | 4.12 | 0.63 | 15.26 |
| $T_{last}$ (h) | 23 | 30.79 | 6.08 | 19.75 |
| $C_{last}$ (ng/mL) | 23 | 0.850 | 0.453 | 53.34 |

TABLE 19

Statistical Analysis of the Log-Transformed Systemic Exposure Parameters of Oxycodone Comparing FORMULATION F11 (Treatment A) to the Reference Product (Treatment E)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 66.3159 | 49.0244 | 135.27 | 126.68 | 144.44 | 0.9999 | 13.38 |
| $\ln(AUC_{last})$ | 465.1938 | 457.8338 | 101.61 | 97.31 | 106.09 | 1.0000 | 8.79 |
| $\ln(AUC_{0\to\infty})$ | 469.4403 | 462.6757 | 101.46 | 97.20 | 105.91 | 1.0000 | 8.73 |

[a]Geometric Mean for FORMULATION F11 (Test) and Reference Product (Ref) based on Least Squares Mean of log-transformed parameter values
[b]Ratio (%) = Geometric Mean (Test)/Geometric Mean (Ref)
[c]90% Confidence Interval

TABLE 20

Statistical Analysis of the Log-Transformed Systemic Exposure Parameters of Oxycodone Comparing FORMULATION F8 (Treatment B) to the Reference Product (Treatment E)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 38.9240 | 49.0244 | 79.40 | 74.36 | 84.78 | 0.9999 | 13.38 |
| $\ln(AUC_{last})$ | 488.7861 | 457.8338 | 106.76 | 102.25 | 111.47 | 1.0000 | 8.79 |
| $\ln(AUC_{0\to\infty})$ | 495.7325 | 462.6757 | 107.14 | 102.65 | 111.84 | 1.0000 | 8.73 |

[a]Geometric Mean for FORMULATION F11 (Test) and Reference Product (Ref) based on Least Squares Mean of log-transformed parameter values
[b]Ratio (%) = Geometric Mean (Test)/Geometric Mean (Ref)
[c]90% Confidence Interval

TABLE 21

Statistical Analysis of the Log-Transformed Systemic Exposure
Parameters of Oxycodone Comparing FORMULATION F9
(Treatment C) to the Reference Product (Treatment E)

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| ln($C_{max}$) | 42.2828 | 49.0244 | 86.25 | 80.79 | 92.07 | 0.9999 | 13.38 |
| ln($AUC_{last}$) | 479.8001 | 457.8338 | 104.80 | 100.38 | 109.41 | 1.0000 | 8.79 |
| ln($AUC_{0\to\infty}$) | 486.0219 | 462.6757 | 105.05 | 100.64 | 109.64 | 1.0000 | 8.73 |

[a]Geometric Mean for FORMULATION F11 (Test) and Reference Product (Ref) based on Least Squares Mean of log-transformed parameter values
[b]Ratio (%) = Geometric Mean (Test)/Geometric Mean (Ref)
[c]90% Confidence Interval

TABLE 22

Statistical Analysis of the Log-Transformed Systemic Exposure
Parameters of Oxycodone Comparing FORMULATION F7
(Treatment D) to the Reference Product (Treatment E)

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| ln($C_{max}$) | 48.0481 | 49.0244 | 98.01 | 91.79 | 104.65 | 0.9999 | 13.38 |
| ln($AUC_{last}$) | 493.6964 | 457.8338 | 107.83 | 103.27 | 112.59 | 1.0000 | 8.79 |
| ln($AUC_{0\to\infty}$) | 497.9574 | 462.6757 | 107.63 | 103.11 | 112.34 | 1.0000 | 8.73 |

[a]Geometric Mean for FORMULATION F11 (Test) and Reference Product (Ref) based on Least Squares Mean of log-transformed parameter values
[b]Ratio (%) = Geometric Mean (Test)/Geometric Mean (Ref)
[c]90% Confidence Interval Example 9

Based on the results of the pilot study, the formulation shown in Table 23 was prepared for pivotal bioequivalence studies. The formulation was encapsulated in a soft gelatin capsule, coated with a polyvinyl alcohol coating (e.g., Opadry® amb II, Colorcon) to provide a 10-12% weight gain, and then annealed in the coating pan by heating the capsules to 65-70° C. for about 30 min to about 90 min, then slowly cooling the capsules to room temperature by reducing the temperature 5° C. over a 5 min to 15 min period (e.g., a 0.3-1° C. decrease per min).

TABLE 23

Oxycodone Hydrochloride Clinical Formulation

| | Dosage 40 mg oxycodone hydrochloride | |
|---|---|---|
| Component | Mass (mg) | % weight |
| Glyceryl monolinoleate (Maisine ™) | 201.1 | 57.5 |
| PEO 301 FP | 105.0 | 30.0 |
| BHA | 1.1 | 0.31 |
| BHT | 0.4 | 0.13 |
| Oxycodone HCl | 42.4 | 12.1 |
| TOTAL | 350.0 | 100.0% |
| Ratio PEO:Maisine ™ 35-1 | 1:1.9 | |
| Ratio API:PEO | 1:2.5 | |

Example 10

Based on the results of the pilot study, a single-dose, open-label, three-way crossover bioequivalence study involving three-period, two-sequence, three-treatment was conducted with the dosage form described in Table 23.

In the first two periods, the subjects received a single dose of oxycodone 40 mg extended-release capsules (Banner Life Sciences; Table 23) or OXYCONTIN® (oxycodone hydrochloride) 40 mg extended-release tablets (Purdue Pharma L.P.) under fasting conditions in a randomized, crossover fashion with balanced sequence. In the third period, all subjects received a single dose of oxycodone 40 mg extended-release capsules (Banner Life Sciences) with a high-fat meal according to the FDA Guidance on food effect evaluation. Twenty-six subjects were enrolled.

Healthy, non-smoking (for at least 6 months prior to first study drug administration), male and non-pregnant female volunteers, 18-55 years of age, inclusive, with a body mass index (BMI) within 18-33 kg/m², inclusive. Six (6) additional subjects were on stand-by. All eligible subjects took naltrexone hydrochloride (Accord Healthcare, Inc., U.S), both at −13 hours and at −1 hour prior to Period 1 study drug administration to ensure that at least 26 qualified subjects would continue study participation, who in the opinion of the PI/Sub-Investigator, did not experience side effects that would preclude them from advancing in the study based on safety concerns. Once 26 subjects have received the study drug in Period 1, the remaining subjects were released from the study.

The assignment of treatment groups (randomization scheme) was be generated by a computer program designed and run in SAS® Version 9.4 at BPSI. This was an open-label study and subjects as well as clinic staff were not be blinded to the randomization. The bioanalytical laboratory staff was blinded and did not have access to the randomization scheme until the bioanalytical analysis is complete.

Subjects who met the eligibility criteria were be assigned equally into one of the following two sequence groups:

|  | Period 1 | Period 2 | Period 3 |
|---|---|---|---|
| Sequence 1 | A | B | C |
| Sequence 2 | B | A | C |

Each subject received a total of three treatments by the end of the study.

| | Treatment Code | | |
|---|---|---|---|
| | A (Test) | B (Reference) | C (Test) |
| Drug Name: | Oxycodone hydrochloride | OXYCONTIN® (oxycodone hydrochloride) | Oxycodone hydrochloride |
| Strength: | 40 mg | 40 mg | 40 mg |
| Dosage Form: | Extended-release capsules | Extended-release tablets | Extended-release capsules |
| Manufactured by/for: | Banner Life Sciences | Purdue Pharma L.P. | Banner Life Sciences |
| Dose: | 1 × 40 mg under fasting conditions | 1 × 40 mg under fasting conditions | 1 × 40 mg under fed conditions |

| Treatment | Opioid Antagonist |
|---|---|
| Drug Name: | Naltrexone hydrochloride |
| Strength: | 50 mg |
| Dosage Form: | Film-coated tablets |
| Manufactured by/for: | AccordHealthcare, Inc., U.S. |
| Dose: | 1 × 50 mg |

Fasting Conditions

Following at least a 10-hour overnight fasting period, subjects were dosed and were required to continue to fast for at least 4 hours after dosing.

Following the fasting period of at least 4-hours after dosing, subjects were given standardized meals and caffeine/methylxanthine-free beverages at scheduled times. In this study, meals were served at approximately −14.5 and −11 hours prior to study drug administration and at approximately 4.5, 9.5, 13.5, 24, 28.5, 33.5 (Only for Period 3) and 37.5 hours after dosing. Meals and beverages during confinement were identical between each study period. Except for water given with study medication, no fluid was allowed from 1 hour before dosing until 1-hour post-dose. Water was allowed/provided ad libitum at all other times.

Fed Conditions

Following at least a 10-hour overnight fasting period, subjects will start an FDA-recommended high-fat, high-calorie breakfast 30 minutes prior to dosing. Study subjects completely consumed this high fat meal within 30 minutes or less. The drug products were administered 30 minutes after the start of the high fat/high calorie breakfast.

Following a fasting period of at least 4-hours after dosing, subjects were given standardized meals and caffeine/methylxanthine-free beverages at scheduled times. Meals were served at approximately −14.5 and −11 hours prior to study drug administration and at approximately 4.5, 9.5, 13.5, 24, 28.5, 33.5 (Only for Period 3) and 37.5 after dosing. Meals and beverages during confinement were identical between each study period.

No food was allowed from at least 10 hours before the FDA-recommended high-fat, high-calorie breakfast. Except for the fluids served with breakfast and the water given with study medication, no fluid was allowed from 1 hour before dosing until 1-hour post-dose. Water was allowed/provided ad libitum at all other times.

Procedures for Collecting Samples for Pharmacokinetic Analysis

Blood were obtained by direct venipuncture in the arm. Blood samples (1×4 mL) were collected in vacutainer tubes containing K2-EDTA as a preservative at pre-dose (0; within 2-hours pre-dosing) and at 0.5, 1, 1.5, 2, 2.5, 3, 3.5, 4, 4.5, 5, 5.5, 6, 7, 8, 12, 18, 24, and 36-hours after dosing.

Plasma samples were assayed for oxycodone using a validated analytical method according to the principles of Good Laboratory Practice.

Data from the following subjects were included in the final pharmacokinetics and statistical analyses:
1. Subjects who completed at least two study periods with test formulation and reference formulation under same gastrointestinal condition or test formulation under different gastrointestinal condition.
2. Subjects who missed samples that have been pre-determined prior to the start of bioanalytical analysis to not significantly impact the overall outcome of the study.

Data from subjects who were dismissed or withdrew due to AE(s) were not be included in the PK and statistical analysis.

Pharmacokinetic parameters were calculated using non-compartmental analysis (NCA) method using SAS® Version 9.4. The following pharmacokinetic parameters were estimated for oxycodone and included in the pharmacokinetic and statistical analysis for the subjects in the final data set:

| | |
|---|---|
| $C_{max}$: | The maximal observed plasma concentration. |
| $T_{max}$: | Time when the maximal plasma concentration is observed. |
| $AUC_{0 \to \tau}$: | Area under the concentration-time curve from time zero until the last measurable concentration or last sampling time τ, whichever occurs first. $AUC_{0 \to \tau}$ is estimated using the trapezoidal method. |
| $AUC_{0 \to \infty}$: | Area under the concentration-time curve from time zero to infinity, calculated as $AUC_{0 \to \tau} + C_{last}/\lambda$, where $C_{last}$ is the last measurable concentration. |
| λ: | Terminal elimination rate constant, estimated by linear regression analysis of the terminal portion of the natrual log of concentration (ln-concentration) vs. time plot. |
| $t_{1/2}$: | Terminal elimination half-life, estimated as $\ln(2)/\lambda$. |

During pharmacokinetic and statistical analyses, drug concentrations below the lower limit of quantitation of the assay were considered as zero prior to the first measurable concentration. Drug concentrations that were below the limit of quantitation following a measurable result were considered as missing during pharmacokinetic calculations and estimations.

Missed samples and non-reportable concentrations (e.g. quantity not sufficient) from the analytical laboratory were treated in the pharmacokinetic analysis as if they had not been scheduled for collection.

The $\lambda$, t½, and $AUC_{0\to\infty}$ parameters were not estimated for plasma concentration-time profiles where the terminal linear phase was not clearly defined (R<0.8).

Descriptive statistics (min., max., median, mean, standard deviation, and coefficient of variability) of all pharmacokinetic parameters were calculated for monomethyl fumarate for the Test and Reference products.

ANOVA including sequence, subjects nested within sequence, period and treatment were performed on the ln-transformed data for $AUC_{0\to\tau}$, $AUC_{0\to\infty}$, and $C_{max}$ and on the untransformed data for $T_{max}$, $\lambda$, and t½. $T_{max}$ was analyzed using the non-parametric Wilcoxon test.

The 90% Confidence Interval of the Test/Reference ratios of geometric means for $AUC_{0\to\tau}$, $AUC_{0\to\infty}$, and $C_{max}$ was calculated based on the LSMEANS and ESTIMATE of the ANOVA. Additional statistical and alternate tests were performed as necessary.

Bioequivalence between Test (A) and Reference (B) products is demonstrated under fasting conditions when the 90% CI for the AB ratios of geometric least-squares means for $AUC_{0\to\tau}$, $AUC_{0\to\infty}$, and $C_{max}$ are completely contained within the U.S. FDA defined acceptance range of 80.00%-125.00% for oxycodone.

Example 11

Comparative Bioavailability Study Results

Figure 29:
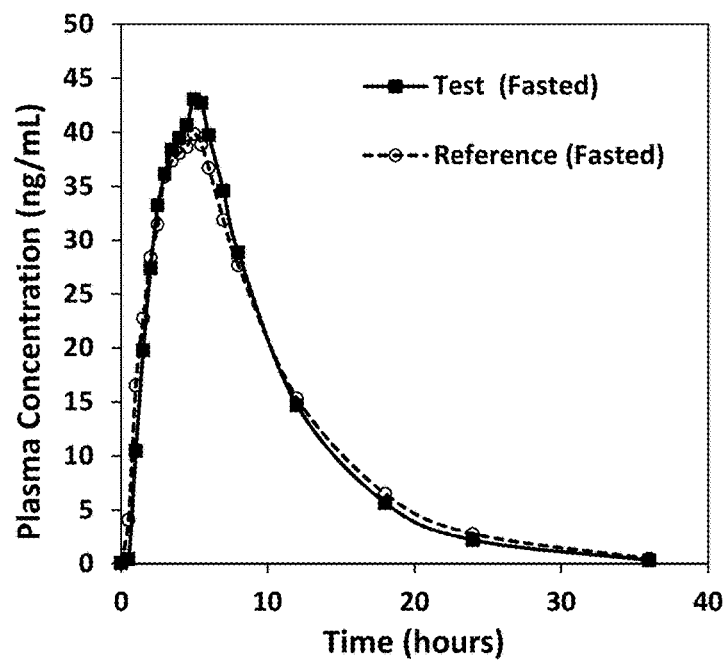
FIG. 29. Mean plasma oxycodone concentrations as a function of time after dosing a 40 mg oxycodone formulation (Table 23) compared with a commercial reference. Panels A and B show the same data, with B having a logarithmic y-axis.
Figure 29:
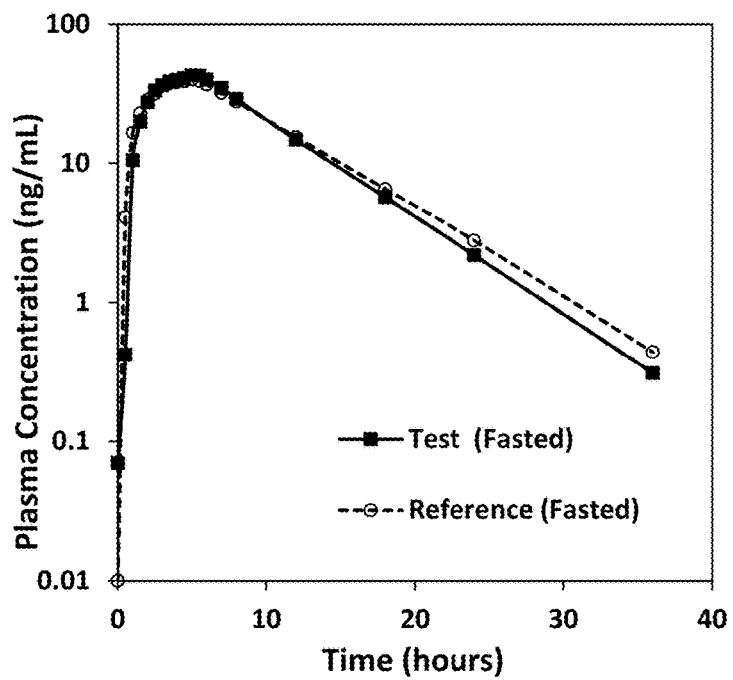
Figure 30:
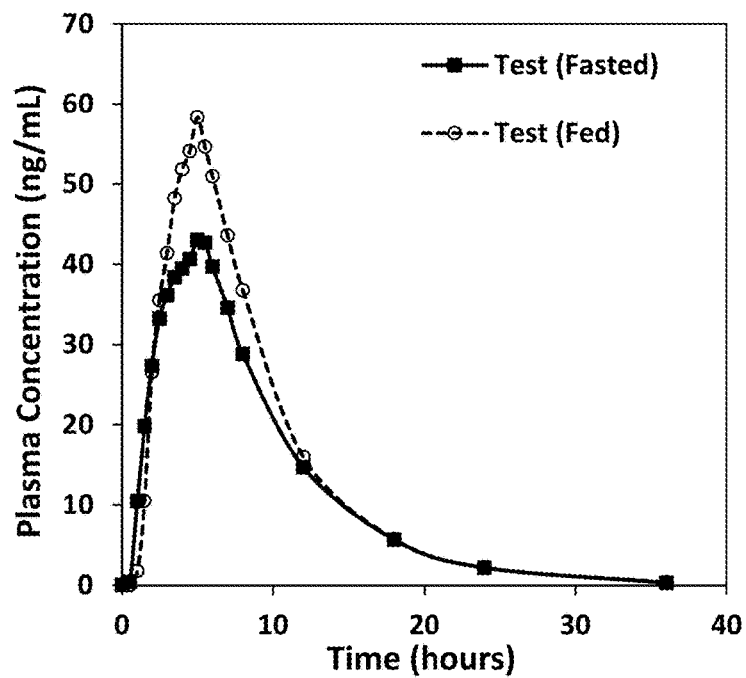
FIG. 30. Mean plasma oxycodone concentrations as a function of time after dosing a 40 mg oxycodone formulation (Table 23) under fasted and fed conditions. Panels A and B show the same data, with B having a logarithmic y-axis.
Figure 30:
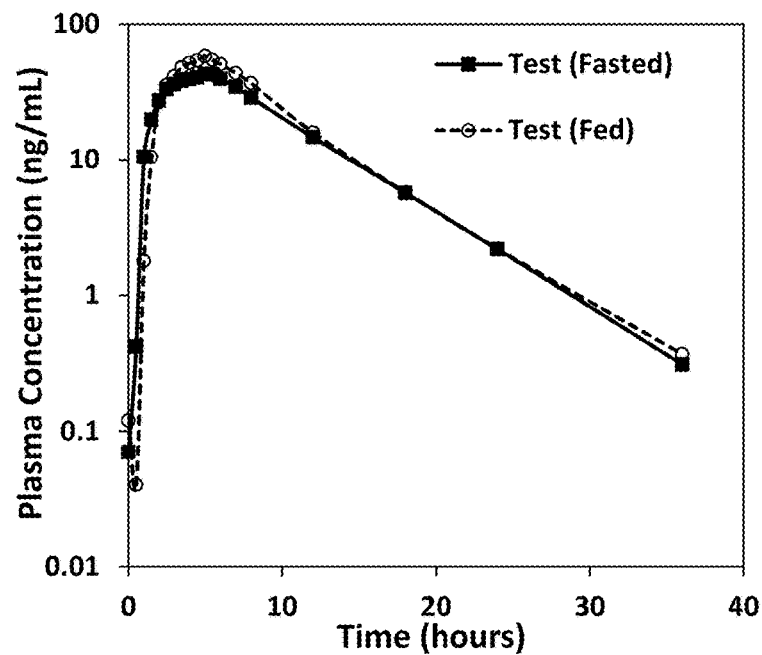

Mean plasma oxycodone concentrations from the bioavailability study described in Example 10 are shown in Tables 24-26. The mean plasma oxycodone concentration data are plotted in FIGS. 29 and 30, respectively. The reference drug (B, Reference) in both studies is OXYCONTIN® (oxycodone hydrochloride) 40 mg extended-release tablets, CII (Purdue Pharma L.P.). Pharmacokinetic parameters are shown in Tables 27-28 for the Tests and Reference.

TABLE 24

Mean Plasma Oxycodone Concentration as a Function of Time after Dosing A Test (Fasted)

| Variable | Time (h) | N | Minimum | Maximum | Mean | Std. Dev. | Coeff. of Variation |
|---|---|---|---|---|---|---|---|
| C1 | Pre-dose | 26 | 0 | 0.81 | 0.07 | 0.19 | 269.58 |
| C2 | 0.5 | 26 | 0 | 4.41 | 0.42 | 0.94 | 221.67 |
| C3 | 1.0 | 26 | 0 | 28.81 | 10.48 | 8.66 | 82.69 |
| C4 | 1.5 | 26 | 0 | 43.33 | 19.79 | 11.9 | 60.11 |
| C5 | 2.0 | 26 | 0 | 51.84 | 27.37 | 13.08 | 47.78 |
| C6 | 2.5 | 26 | 0 | 61.85 | 33.26 | 14.92 | 44.85 |
| C7 | 3.0 | 26 | 3.4 | 67.69 | 36.15 | 13.78 | 38.11 |
| C8 | 3.5 | 26 | 19.15 | 65.51 | 38.38 | 11.7 | 30.48 |
| C9 | 4.0 | 26 | 23.93 | 67.01 | 39.48 | 11.39 | 28.85 |
| C10 | 4.5 | 26 | 23.63 | 66.32 | 40.66 | 11.27 | 27.72 |
| C11 | 5.0 | 26 | 24.44 | 74.2 | 43.05 | 12.07 | 28.04 |
| C12 | 5.5 | 26 | 24.71 | 73.04 | 42.71 | 12.02 | 28.14 |
| C13 | 6.0 | 26 | 22.36 | 67.57 | 39.73 | 11.27 | 28.35 |
| C14 | 7.0 | 26 | 21.07 | 56.38 | 34.6 | 9.77 | 28.24 |
| C15 | 8.0 | 26 | 18 | 41.41 | 28.86 | 6.94 | 24.04 |
| C16 | 12.0 | 26 | 6.7 | 23.53 | 14.7 | 4.71 | 32.06 |
| C17 | 18.0 | 26 | 1.97 | 9.67 | 5.68 | 2.42 | 42.55 |
| C18 | 24.0 | 26 | 0.72 | 4.44 | 2.19 | 1.1 | 50.42 |
| C19 | 36.0 | 26 | 0 | 0.78 | 0.31 | 0.28 | 89.76 |

TABLE 25

Mean Plasma Oxycodone Concentration as a Function of Time after Dosing B Reference (Fasted)

| Variable | Time (h) | N | Minimum | Maximum | Mean | Std. Dev. | Coeff. of Variation |
|---|---|---|---|---|---|---|---|
| C1 | Pre-dose | 26 | 0 | 0.28 | 0.01 | 0.05 | 509.9 |
| C2 | 0.5 | 26 | 0.66 | 14.45 | 4.09 | 3.51 | 85.81 |
| C3 | 1.0 | 26 | 4.86 | 38.35 | 16.52 | 8.8 | 53.27 |
| C4 | 1.5 | 26 | 11.23 | 46.21 | 22.73 | 9.75 | 42.91 |
| C5 | 2.0 | 26 | 11.2 | 60.27 | 28.38 | 11.13 | 39.22 |
| C6 | 2.5 | 26 | 13.04 | 67.82 | 31.46 | 10.62 | 33.77 |
| C7 | 3.0 | 26 | 17.98 | 70.57 | 35.92 | 9.64 | 26.83 |
| C8 | 3.5 | 26 | 21.51 | 69.79 | 37.36 | 9.02 | 24.15 |
| C9 | 4.0 | 26 | 21.92 | 75.07 | 38.07 | 10.22 | 26.85 |
| C10 | 4.5 | 26 | 25.71 | 70.87 | 38.65 | 9.38 | 24.27 |
| C11 | 5.0 | 26 | 25.19 | 68.07 | 39.84 | 10.35 | 25.97 |
| C12 | 5.5 | 26 | 22.1 | 63.53 | 38.86 | 10.38 | 26.71 |
| C13 | 6.0 | 26 | 20.91 | 61.07 | 36.7 | 9.96 | 27.15 |
| C14 | 7.0 | 26 | 18.65 | 51.79 | 31.88 | 8.08 | 25.34 |
| C15 | 8.0 | 26 | 17.89 | 45.48 | 27.65 | 7.38 | 26.69 |
| C16 | 12.0 | 26 | 7.57 | 27.21 | 15.34 | 5.11 | 33.3 |
| C17 | 18.0 | 26 | 2.56 | 12.88 | 6.51 | 2.47 | 37.88 |
| C18 | 24.0 | 26 | 0.93 | 5.65 | 2.79 | 1.25 | 44.67 |
| C19 | 36.0 | 26 | 0 | 1.78 | 0.44 | 0.39 | 88.04 |

TABLE 26

Mean Plasma Oxycodone Concentration as a Function of Time after Dosing C Test (Fed)

| Variable | Time (h) | N | Minimum | Maximum | Mean | Std. Dev. | Coeff. of Variation |
|---|---|---|---|---|---|---|---|
| C1 | Pre-dose | 26 | 0 | 0.53 | 0.12 | 0.17 | 135.68 |
| C2 | 0.5 | 26 | 0 | 0.58 | 0.04 | 0.13 | 303.47 |
| C3 | 1.0 | 26 | 0 | 15.76 | 1.79 | 3.68 | 206.37 |
| C4 | 1.5 | 26 | 0 | 39.67 | 10.5 | 10.56 | 100.53 |
| C5 | 2.0 | 26 | 0 | 110.66 | 26.62 | 24.12 | 90.61 |
| C6 | 2.5 | 26 | 0.36 | 93.17 | 35.57 | 23.99 | 67.46 |
| C7 | 3.0 | 26 | 1.48 | 87.06 | 41.37 | 21.71 | 52.48 |
| C8 | 3.5 | 26 | 7.6 | 89.26 | 48.22 | 19.34 | 40.1 |
| C9 | 4.0 | 26 | 25.29 | 85.98 | 51.82 | 14.76 | 28.49 |
| C10 | 4.5 | 26 | 36.81 | 81.69 | 54.08 | 12.25 | 22.66 |
| C11 | 5.0 | 26 | 36.85 | 82.93 | 58.32 | 11.39 | 19.53 |
| C12 | 5.5 | 26 | 35.1 | 76.76 | 54.63 | 11.03 | 20.2 |
| C13 | 6.0 | 26 | 32.16 | 70.05 | 50.95 | 10.99 | 21.56 |
| C14 | 7.0 | 26 | 25.72 | 63.73 | 43.61 | 10.75 | 24.66 |
| C15 | 8.0 | 26 | 20.57 | 56.5 | 36.79 | 9.6 | 26.09 |
| C16 | 12.0 | 26 | 7.75 | 27.82 | 15.96 | 5.45 | 34.14 |
| C17 | 18.0 | 26 | 2.63 | 10.51 | 5.73 | 2.29 | 40.06 |
| C18 | 24.0 | 26 | 0.74 | 4.51 | 2.2 | 0.96 | 43.66 |
| C19 | 36.0 | 26 | 0 | 1.05 | 0.37 | 0.28 | 75.25 |

TABLE 27

Pharmacokinetic Parameters for Plasma Oxycodone

| | $AUC_\tau$ (h·ng/mL) | $AUC_\infty$ (h·ng/mL) | $C_{max}$ (ng/mL) | $T_{max}$ (h)* | $AUC_\tau$ (h·ng/mL) | $\lambda_z$ (1/h)* | $t_{1/2}$ (h)* | ln ($AUC_\tau$) | ln ($AUC_\infty$) | ln ($C_{max}$) |
|---|---|---|---|---|---|---|---|---|---|---|
| A Test (Fasted) | | | | | | | | | | |
| N | 26 | 26 | 26 | 26 | 26 | 26 | 26 | 26 | 26 | 26 |
| Max | 658.33 | 662.43 | 0.9968 | 74.2 | 7 | 0.2371 | 5.42 | 6.4897 | 6.4959 | 4.3068 |
| Min | 248.62 | 257.8 | 0.9644 | 25.96 | 2.5 | 0.1278 | 2.92 | 5.5159 | 5.5522 | 3.2566 |
| Median | 436.66 | 442.63 | 0.9905 | 43.94 | 5 | 0.1574 | 4.4 | 6.0791 | 6.0927 | 3.7827 |
| Mean | 428.81 | 433.53 | 0.988 | 45.99 | 4.63 | 0.1625 | 4.36 | 6.0253 | 6.0374 | 3.7974 |
| Std. Dev. | 114.63 | 114.13 | 0.0078 | 11.94 | 1.12 | 0.026 | 0.62 | 0.2762 | 0.2713 | 0.2531 |
| CV % | 26.73 | 26.33 | 0.79 | 25.96 | 24.17 | 16.03 | 14.33 | 4.58 | 4.49 | 6.67 |
| B Reference (Fasted) | | | | | | | | | | |
| N | 26 | 26 | 26 | 26 | 26 | 26 | 26 | 26 | 26 | 26 |
| Max | 760.14 | 764.18 | 0.996 | 75.07 | 5.53 | 0.1945 | 7.59 | 6.6335 | 6.6388 | 4.3184 |
| Min | 259.4 | 267.95 | 0.9493 | 28.49 | 2 | 0.0913 | 3.56 | 5.5584 | 5.5908 | 3.3496 |
| Median | 428.28 | 430.29 | 0.9922 | 41.41 | 5 | 0.1581 | 4.38 | 6.0597 | 6.0644 | 3.7234 |
| Mean | 435.2 | 440.68 | 0.9867 | 42.03 | 4.56 | 0.1539 | 4.62 | 6.0466 | 6.0601 | 3.71 |
| Std. Dev. | 109.41 | 109.07 | 0.0117 | 10.73 | 0.92 | 0.0233 | 0.85 | 0.2456 | 0.2415 | 0.2382 |
| CV % | 25.14 | 24.75 | 1.19 | 25.52 | 20.19 | 15.11 | 18.46 | 4.06 | 3.99 | 6.42 |
| C Test (Fed) | | | | | | | | | | |
| N | 26 | 26 | 26 | 26 | 26 | 26 | 26 | 26 | 26 | 26 |
| Max | 658.33 | 662.43 | 0.9968 | 74.2 | 7 | 0.2371 | 5.42 | 6.4897 | 6.4959 | 4.3068 |
| Min | 248.62 | 257.8 | 0.9644 | 25.96 | 2.5 | 0.1278 | 2.92 | 5.5159 | 5.5522 | 3.2566 |
| Median | 436.66 | 442.63 | 0.9905 | 43.94 | 5 | 0.1574 | 4.4 | 6.0791 | 6.0927 | 3.7827 |
| Mean | 428.81 | 433.53 | 0.988 | 45.99 | 4.63 | 0.1625 | 4.36 | 6.0253 | 6.0374 | 3.7974 |
| Std. Dev. | 114.63 | 114.13 | 0.0078 | 11.94 | 1.12 | 0.026 | 0.62 | 0.2762 | 0.2713 | 0.2531 |
| CV % | 26.73 | 26.33 | 0.79 | 25.96 | 24.17 | 16.03 | 14.33 | 4.58 | 4.49 | 6.67 |

TABLE 28

Summary of Comparative Bioavailability Analysis for Oxycodone
Randomized, 4-way crossover, open-label, single-dose, fasting design

| Sample | $AUC_{0\to\tau}$ (h·ng/mL) | $AUC_{0\to\infty}$ (h·ng/mL) | $C_{max}$ (ng/mL) | $T_{max}$ (h)* | $t_{1/2}$ (h)* | $\lambda_z$ (1/h)* | $AUC_{0\to\tau}/AUC_{0\to\infty}$† |
|---|---|---|---|---|---|---|---|
| | Geometric Mean *Arithmetic Mean (% CV) | | | | | | |
| A Test (Fasted) | 413.76 / 428.81 (26.73) | 418.81 / 433.53 (26.33) | 44.58 / 45.99 (25.96) | 5.00 (2.50-7.00) | 4.36 (14.33) | 0.1625 (16.03) | 0.9880 (0.79) |
| C Test (Fed) | 486.29 / 499.59 (23.09) | 490.61 / 503.73 (22.85) | 60.57 / 62.24 (24.79) | 4.53 (2.03-6.00) | 4.56 (16.93) | 0.1569 (19.29) | 0.9912 (0.57) |
| B Reference | 422.68 / 435.2 (25.14) | 428.4 / 440.68 (24.75) | 40.85 / 42.03 (25.52) | 5.00 (2.00-5.53) | 4.62 (18.46) | 0.1539 (15.11) | 0.9867 (1.19) |

| | | Ratio of Geometric Means (Test:Ref) | 90% Confidence Interval | Intra-subject CV (%) |
|---|---|---|---|---|
| A Test/B Reference | $AUC_{0\to\tau}$ | 97.89 | 93.00-103.04 | 10.85 |
| | $AUC_{0\to\infty}$ | 97.76 | 92.98-102.79 | 10.62 |
| | $C_{max}$ | 109.13 | 102.39-116.31 | 13.51 |
| A Test/ C Test | $AUC_{0\to\tau}$ | 117.5 | 103.96-132.87 | 26.33 |
| | $AUC_{0\to\infty}$ | 117.14 | 103.81-132.19 | 25.93 |
| | $C_{max}$ | 135.87 | 121.02-152.53 | 24.79 |

Test A, C: oxycodone hydrochloride, 40 mg extended-release capsules. See Table 23.
Reference: OXYCONTIN ® (oxycodone hydrochloride) 40 mg extended-release tablets, CII (Purdue Pharma L.P.).
*Arithmetic mean (% CV) only
†Median and range only Example 9

Abuse deterrent dosage forms were prepared using the compositions shown in Table 29 and encapsulated in a soft capsule shell with a polyvinyl alcohol coating as a moisture barrier. The dosage forms were annealed in the coating pan after coating at 60-70° C. for 30 to 90 min and then slowly cooled to room temperature (dropping about 5° C. every 5 to 15 min.).

TABLE 29

Abuse Deterrent Controlled Release Oxycodone Compositions

| | Dosage | | | |
|---|---|---|---|---|
| | 10 mg | | 15 mg | |
| Component | Mass (mg) | % weight | Mass (mg) | % weight |
| Glyceryl monolinoleate (Maisine ™) | 222.0 | 63.4 | 218.5 | 62.4 |
| PEO 301 FP | 115.9 | 33.1 | 114.1 | 32.6 |
| BHA | 1.1 | 0.3 | 1.1 | 0.3 |
| BHT | 0.4 | 0.1 | 0.4 | 0.1 |
| Oxycodone HCl | 10.6 | 3.0 | 15.9 | 4.5 |
| TOTAL | 350.0 | 100.0% | 350.0 | 100.0% |
| Ratio PEO:Maisine ™ 35-1 | 1:1.9 | | 1:1.9 | |
| Ratio API:PEO | 1:10.9 | | 1:7.2 | |

| | Dosage | | | |
|---|---|---|---|---|
| | 20 mg | | 30 mg | |
| Component | Mass (mg) | % weight | Mass (mg) | % weight |
| Glyceryl monolinoleate (Maisine ™) | 215.0 | 61.4 | 208.1 | 59.4 |
| PEO 301 FP | 112.3 | 32.1 | 108.6 | 31.0 |
| BHA | 1.1 | 0.3 | 1.1 | 0.3 |
| BHT | 0.4 | 0.1 | 0.4 | 0.1 |
| Oxycodone HCl | 21.2 | 6.1 | 31.8 | 9.1 |
| TOTAL | 350.0 | 100.0% | 350.0 | 100.0% |
| Ratio PEO:Maisine ™ 35-1 | 1:1.9 | | 1:1.9 | |
| Ratio API:PEO | 1:5.3 | | 1:3.4 | |

| | Dosage 40 mg | |
|---|---|---|
| Component | Mass (mg) | % weight |
| Glyceryl monolinoleate (Maisine ™) | 201.1 | 57.5 |
| PEO 301 FP | 105.0 | 30.0 |
| BHA | 1.1 | 0.31 |
| BHT | 0.4 | 0.13 |
| Oxycodone HCl | 42.4 | 12.1 |
| TOTAL | 350.0 | 100.0% |
| Ratio PEO:Maisine ™ 35-1 | 1:1.9 | |
| Ratio API:PEO | 1:2.5 | |

What is claimed is:

1. An oral pharmaceutical composition comprising:
   (a) about 35% to about 70% by mass glyceryl monolinoleate;
   (b) about 20% to about 50% by mass polyethylene oxide having a molecular weight ($M_v$) of about 1,000,000 to about 7,000,000; and
   (c) oxycodone or a salt thereof.

2. The composition of claim 1, wherein a ratio of polyethylene oxide to glyceryl monolinoleate is about 1:2.

3. The composition of claim 1, wherein a ratio of oxycodone to polyethylene oxide comprises a range of about 1:1 to about 1:15.

4. The composition of claim 1, wherein the oxycodone comprises about 1% to about 30% of the composition by mass.

5. The composition of claim 1, wherein the composition further comprises one or more antioxidants.

6. The composition of claim 5, wherein the antioxidant comprises about 0.05% to about 0.5% of the composition by mass.

7. The composition of claim 5, wherein the antioxidant comprises butylated hydroxyanisole (BHA), butylated hydroxytoluene (BHT), or a combination thereof.

8. The composition of claim 1, wherein the polyethylene oxide comprises a polyethylene oxide having an average molecular weight ($M_v$) of about 4,000,000.

9. The composition of claim 1, wherein the oxycodone comprises oxycodone hydrochloride or oxycodone myristate.

10. The composition of claim 1, wherein the oxycodone comprises about 5 mg to about 120 mg of oxycodone hydrochloride.

11. The composition of claim 1, wherein the oxycodone comprises about 5 mg, about 10 mg, about 15 mg, about 20 mg, about 30 mg, or about 40 mg of oxycodone hydrochloride.

12. The composition of claim 1, wherein the composition comprises:
   (a) about 35% to about 70% by mass of glyceryl monolinoleate;
   (b) about 20% to about 50% by mass of polyethylene oxide; and
   (c) about 1% to about 30% by mass of oxycodone hydrochloride.

13. The composition of claim 12, further comprising:
   (d) about 0.1% to about 0.4% by mass of BHA; and
   (e) about 0.05% to about 0.1% by mass of BHT.

14. The composition of claim 1, wherein the composition comprises:
   (a) about 50% to about 70% by mass of glyceryl monolinoleate;
   (b) about 25% to about 40% by mass of polyethylene oxide;
   (c) about 0.1% to about 0.4% by mass of BHA;
   (d) about 0.05% to about 0.1% by mass of BHT; and
   (e) about 1% to about 20% of by mass of oxycodone hydrochloride.

15. An oral abuse deterrent controlled release dosage form comprising a capsule encapsulating:
   (a) about 50% to about 70% by mass glyceryl monolinoleate;
   (b) about 25% to about 40% by mass polyethylene oxide comprising an average molecular weight ($M_v$) of about 4,000,000; and
   (c) about 1% to about 20% by mass of oxycodone hydrochloride; and
   the dosage form having been heated to about 50° C. to about 80° C. for about 10 min to about 180 min, and cooled to room temperature by reducing the temperature at a rate of about 2° C. to about 10° C. per about 5 min to about 15 min.

16. The dosage form of claim 15, wherein the oxycodone hydrochloride comprises about 5 mg, about 10 mg, about 15 mg, about 20 mg, about 30 mg, or about 40 mg of oxycodone hydrochloride.

17. The dosage form of claim 15, wherein the capsule is coated with a polyvinyl alcohol coating.

18. The dosage form of claim 15, wherein the dosage form exhibits an in vitro dissolution rate at pH 1.2 of about 50% after about 90 minutes.

19. A method for treating, reducing symptoms of, or retarding an onset of pain comprising administering to a subject in need thereof the dosage form of claim 15.

20. A method for inhibiting extraction of oxycodone from a pharmaceutical composition, the method comprising: providing the dosage form of claim 15, wherein the dosage form is resistant to crushing, grating, grinding, cutting, solvation, or dissolution in water or alcohol.

21. A kit for dispensing an abuse deterrent dosage form comprising:
   (a) one or more dosage forms of claim 15;
   (b) one or more receptacles comprising a tamper evident, moisture proof packaging that reduces the ability of removing the dosage form comprising blister or strip packs, aluminum blisters, transparent or opaque polymer blisters or pouches, polypropylene tubes, colored blister materials, tubes, bottles, and bottles optionally containing a child-resistant feature, optionally comprising a desiccant, such as a molecular sieve or silica gel; and
   (c) optionally, an insert comprising instructions or prescribing information for the dosage form.

22. A method for manufacturing an abuse deterrent dosage form comprising:
   (a) combining about 35% to about 70% by mass glyceryl monolinoleate, about 20% to about 50% by mass polyethylene oxide having a molecular weight ($M_v$) of about 1,000,000 to about 7,000,000, and oxycodone;
   (b) encapsulating the combination into capsules;
   (c) incubating the capsules at an elevated temperature for a period of time; and
   (d) cooling the capsules to room temperature.

23. The method of claim 22, wherein the capsules produced in step (b) are coated with a coating prior to the incubating of step (c).

24. The method of claim 22, wherein the capsules are incubated in step (c) at about 50° C. to about 80° C. for about 10 min to about 180 min.

25. The method of claim 22, wherein the capsules are cooled in step (d) by reducing the temperature at a rate of about 2° C. to about 10° C. per about 5 to about 15 min.

26. A method for treating pain comprising administering to a subject a pharmaceutical dosage form comprising about 35% to about 70% by mass glyceryl monolinoleate, about 20% to about 50% by mass polyethylene oxide having a molecular weight ($M_v$) of about 1,000,000 to about 7,000,000, and about 40 mg oxycodone, the method capable of achieving one or more of the following pharmacokinetic parameters following ingestion by a subject:
   (a) a mean plasma oxycodone $T_{max}$ of about 4.5 hours to about 5.0 hours;
   (b) a mean plasma oxycodone $C_{max}$ of about 40 ng/mL to about 65 ng/mL;
   (c) a mean plasma oxycodone $AUC_{0 \to \tau}$ of about 400 h·ng/mL to about 500 h·ng/mL;
   (d) a mean plasma oxycodone $AUC_{0 \to \infty}$ of about 400 h·ng/mL to about 500 h·ng/mL;
   (e) a mean oxycodone half-life ($t\frac{1}{2}$) of about 4.4 hours to about 4.6 hours; or
   (f) a mean oxycodone overall elimination rate constant ($\lambda_z$) of about 0.14 $h^{-1}$ to about 0.17 $h^{-1}$.

\* \* \* \* \*